US007452664B2

(12) United States Patent
Guarente et al.

(10) Patent No.: US 7,452,664 B2
(45) Date of Patent: Nov. 18, 2008

(54) METHODS FOR IDENTIFYING AGENTS WHICH ALTER HISTONE PROTEIN ACETYLATION

(75) Inventors: Leonard Guarente, Chestnut Hill, MA (US); Shin-ichiro Imai, Somerville, MA (US); Christopher Armstrong, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/461,580

(22) Filed: Dec. 15, 1999

(65) Prior Publication Data

US 2003/0207325 A1 Nov. 6, 2003

(51) Int. Cl.
*C12Q 1/68* (2006.01)
*G01N 33/53* (2006.01)
(52) U.S. Cl. .................... 435/6; 435/4; 435/5; 435/7.6; 435/15
(58) Field of Classification Search .................. 435/5, 435/6, 4, 7.6, 15
See application file for complete search history.

(56) References Cited

U.S. PATENT DOCUMENTS

| 5,874,210 A | 2/1999 | Guarente et al. ............... 435/4 |
| 5,919,618 A | 7/1999 | Guarente et al. ............... 435/6 |

OTHER PUBLICATIONS

Bowie et al (Science, 1990, 257:1306-1310).*
Bork (Genome Research, 2000, 10:398-400).*
Gottlieb, S., et al., "A New Role for a Yeast Transcriptional Silencer Gene, SIR2, in Regulation of Recombination in Ribosomal DNA", *Cell*, 56:771-776 (1989).
Tani, T., et al., "Nucleolar Accumulation of Poly (A) +RNA in Heat-shocked Yeast Cells: Implication of Nucleolar Involvement in mRNA Transport", *Molecular Biology of the Cell*, 6:1515-1534 (1995).
Oakes, M., et al., "Structural Alterations of the Nucleolus in Mutants of *Saccharomyces cerevisiae* Defective in RNA Polymerase I", *Molecular and Cellular Biology*, 13(4):2441-2455 (1993).
Palladino, F., et al., "SIR3 and SIR4 Proteins Are Required for the Positioning and Integrity of Yeast Telomeres", *Cell*, 75:543-555 (1993).
Sweeney, R., et al., "Extrachromosomal Elements Cause a Reduced Division Potential in *nib* 1 Strains of *Saccharomyces cerevisiae*", Genetics Society of America, 122:749-757 (1989).
Jamet-Vierny, C., et al., "Senescence in Podospora anserina: Amplification of a Mitochondrial DNA Sequence", *Cell*, 21:189-194 (1980).
Sinclair, D.A., et al., "Extrachromosomal rDNA Circles- A Cause if Aging in Yeast", *Cell*, 91:1033-1042 (1997).
Kennedy, B.K., et al., "Redistribution of Silencing Proteins from Telomeres to the Nucleolus Is Asociated with Extension of Life Span in *S. cerevisiae*," *Cell*, 89:381-391 (1997).

de Beus, E., et al., "Yeast *NOP2* Encodes an Essential Nucleolar Protein with Homology to a Human Proliferation Marker," *J. Cell Biol.*, 127:1799-1812 (1994).
Kadowaki, T., et al., "Nuclear mRNA Accumulation Causes Nucleolar Fragmentation in Yeast *mtr2* Mutant," *Molecular Biology of the Cell*, 5:1253-1263 (1994).
Frye, R.A., "Characterization of Five Human cDNAs with Homology to the Yeast SIR2 Gene: Sir2-like Proteins (Sirtuins) Metabolize NAD and May Have Protein ADP-Ribosyltransferase Activity," *Biochemical and Biophysical Research Communications*, 260:273-279 (1999).
"Genetic Switch Seen Affecting Mouse Aging," *The Boston Globe* (Nov. 18, 1999).
EST AA199012.
EST AA105536.
EST AA260334.
Sinclair, D.A., "Molecular Mechanisms of Yeast Aging." *Trends in Biochemical Sciences*, 23:131-134 (1998).
Frye, R.A., "Human Sir2-like proteins (sirtuins) are NAD-metabolizing protein (ADP-ribosyl) transferases." Presented at the American Association for Cancer Research Annual Meeting, vol. 40, Philadelphia, PA (Mar. 1999).
GenBank Accession No. AI465820.
GenBank Accession No. AI465098.
GenBank Accession No. AI466061.
Kaeberlein, M., et al., "The SIR2/3/4 complex and SIR2 alone promote longevity in *Saccharomyces cerevisiae* by two different mechanisms," *Genes & Development*, 13(19):2570-2580 (1999).
Karpen, G., et al., *The case for epigenetic effects on centromere identity and function*, Trends Genet 13: 489-496 (1997).
Grunstein, M., *Yeast Heterochromatin: Regulation of Its Assembly and Inheritance by Histones*, Cell 93, 325-328 (1998)).
Sherman, J. M., et al., *An uncertain silence*, Trends Genet. 13: 308-313 (1997).
Ivy, J. M., et al., *Cloning and Characterization of Four SIR Genes of Saccharomyces cerevisia*, Mol. Cell. Biol. 6: 688-702 (1986).

(Continued)

*Primary Examiner*—Robert A Zeman
(74) *Attorney, Agent, or Firm*—Lewis, Lando & Anastasi, LLP

(57) ABSTRACT

Methods of identifying agents which alter the NAD-dependent acetylation status and mono-ADP-ribosylation of nuclear proteins are disclosed. The methods further include identifying agents which alter the life span or aging of a cell or an organism by determining the level of NAD-dependent acetylation and/or ADP ribosylation of a nuclear protein. The invention also relates to a mammalian Sir2 protein which acetylates or deacetylates nuclear proteins in a NAD-dependent manner and has mono-ADP-ribosyltransferase activity. Host cells producing the Sir2 protein and antibodies to the Sir2 protein are also provided.

49 Claims, 41 Drawing Sheets

OTHER PUBLICATIONS

Gotta, M., et al., *The Clustering of Telomeres and Colocalization with Rap1, Sir3, and Sir4 Proteins in Wild-Type Saccharomyces cerevisiae*, J. Cell Biol. 134: 1349-1363 (1996).

Rine, J., et al., *Four Genes Responsible for a Position Effect on Expression From HML and HMR in Saccharomyces cerevisiae*, Genetics 116: 9-22 (1987).

Aparicio, O. M., et al., *Modifiers of Position Effect Are Shared between Telomeric and Silent Mating-Type Loci in S. cerevisiae*, Cell 66: 1279-1287 (1991)).

Triolo, T., et al., *Role of interactions between the origin recognition in complex and SIR1 in transcriptional silencing*, Nature 381: 251-253 (1996).

Hardy, C. F. J., et al., *A RAP1-interacting protein involved in transcriptional silencing and telomere length regulation*, Genes Dev. 6: 801 (1992).

Moretti, P., et al., *Evidence that a complex of SIR proteins interacts with the silencer and telomere-binding protein RAP1*, Genes Dev. 8: 2257 (1994).

Shou, W., et al., *Exit from Mitosis Is Triggerd by Tem1-Dependent Release of the Protein Phosphatase Cdc14 from Nucleolar Rent complex*, Cell 97: 233-244 (1999).

Mills, K. D., et al., *MEC1-Dependent Redistribution of Sir3 Silencing Protein from Telomeres to DNA Double-Strand Breaks*, Cell 97: 609-620 (1999).

Martin, S. G., et al., *Relocalization of Telomeric Ku and SIR Proteins in Response to DNA Strands Breaks in Yeast*, Cell 97: 621-633 (1999).

Bryk, M., et al., *Transcriptional silencing of Ty1 elements in the RDN1 locus in yeast*, Genes Dev. 11: 255-269 (1997).

Smith, J. S., et al., *An unusual form of transcriptional silencing in yeast ribosomal DNA*, Genes Dev. 11: 241-254 (1997.

Sinclair, D. A., et al., *Accelerated Aging and Nucleolar Fragmentation in Yeast sgs1 Mutants*, Science 277: 1313-1316 (1997).

Park, P. U., et al., *Effects of Mutations in DNA Repair Genes on Formation of Ribosomal DNA Circles and Life Span in Saccharomyces cerevisiae*, Mol. Cell. Biol. 19: 3848-3856 (1999.

Braunstein, M., et al., *Efficient Transcriptional Silencing in Saccharomyces cerevisiae Requires a Heterochromatin Histone Acetylation Pattern*, Mol. Cell. Biol. 16: 4349-4356 (1996).

Braunstein, M., et al., *Transcriptional silencing in yeast is associated with reduced nucleosome acetylation*, Genes Dev 7: 592-604 (1993)).

Brachmann, C. B., et al., *The SIR2 gene family, conserved from bacteria to humans, functions in silencing, cell cycle progression, and chromosome stability*, Genes Dev. 9: 2888-2902 (1995).

Tsang, A. W., et al., *CobB, a New Member of the SIR2 Family of Eucaryotic Regulatory Proteins, Is Required to Compensate for the Lack of Nicotinate Mononucleotide:5,6-Dimethylbenzimidazole Phosphoribosyltransferase Activity in cobT Mutants during Cobalamin Biosynthesis in Salmonella typhimurium LT2*, J. Biol. Chem. 273: 31788-31794 (1998).

\* cited by examiner

```
  1  MADEVALALQAAGSPSAAAAMEAASQPADEPLRKRPRRDG
 41  PGLGRSPGEPSAAVAPAAAGCEAASAAAPAALWREAAGAA
 81  ASAEREAPATAVAGDGDNGSGLRREPRAADDFDDDEGEEE
121  DEAAAAAAAAAIGYRDNLLLTDGLLTNGFHSCESDDDDRT
161  SHASSSDWTPRPRIGPYTFVQQHLMIGTDPRTILKDLLPE
201  TIPPPELDDMTLWQIVINILSEPPKRKKRKDINTIEDAVK
241  LLQECKKIIVLTGAGVSVSCGIPDFRSRDGIYARLAVDFP
281  DLPDPQAMFDIEYFRKDPRPFFKFAKEIYPGQFQPSLCHK
321  FIALSDKEGKLLRNYTQNIDTLEQVAGIQRILQCHGSFAT
361  ASCLICKYKVDCEAVRGDIFNQVVPRCPRCPADEPLAIMK
401  PEIVFFGENLPEQFHRAMKYDKDEVDLLIVIGSSLKVRPV
441  ALIPSSIPHEVPQILINREPLPHLHFDVELLGDCDVIINE
481  LCHRLGGEYAKLCCNPVKLSEITEKPPRPQKELVHLSELP
521  PTPLHISEDSSSPERTVPQDSSVIATLVDQATNNNVNDLE
561  VSESSCVEEKPQEVQTSRNVENINVENPDFKAVGSSTADK
601  NERTSVAETVRKCWPNRLAKEQISKRLEGNQYLFVPPNRY
641  IFHGAEVYSDSEDDVLSSSSCGSNSDSGTCQSPSLEEPLE
681  DESEIEEFYNGLEDDTERPECAGGSGFGADGGDQEVVNEA
721  IATRQELTDVNYPSDKS
```

Fig. 2A

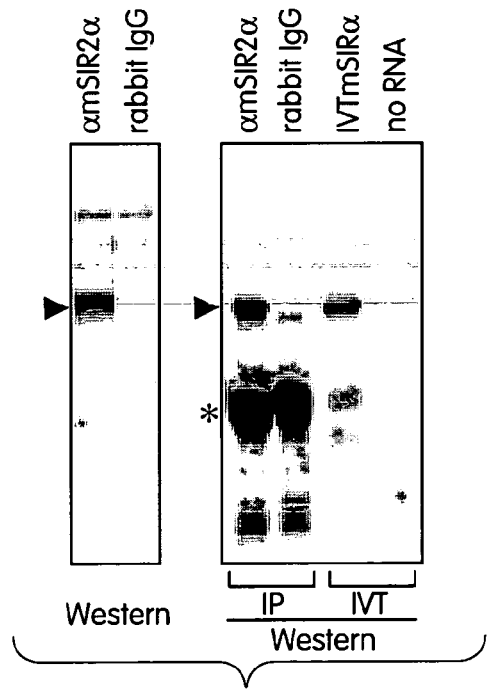

Fig. 2B

| | | | |
|---|---|---|---|
| ySIR2 | 1 | INKVLCT---RLRLSNFITIDHFIQKLHTARKI | 30 |
| yHST1 | 1 | INKVLST---RLRLPNFNTIDHFTATLRNAKKI | 30 |
| mSIR2α | 1 | VINILSEPPKRKKRKDINTIEDAVKLLQECKKI | 33 |
| CobB | 1 | ------------------------MMENPRV | 7 |

| | | | |
|---|---|---|---|
| ySIR2 | 31 | LVLTGAGVSTSLGIPDFRSSEGFYS--KIKHLG | 61 |
| yHST1 | 31 | LVLTGAGVSTSLGIPDFRSSEGFYS--KIRHLG | 61 |
| mSIR2α | 34 | IVLTGAGVSVSCGIPDFRSRDGIYARLAVDFPD | 66 |
| CobB | 8 | LVLTGAGISAESGIRTFRAADGLWE--EHRVED | 38 |

| | | | |
|---|---|---|---|
| ySIR2 | 62 | LDDPQDVFNYNIFMHDPSVFYNIANMVLP-PEK | 93 |
| yHST1 | 62 | LEDPQDVFNLDIFLQDPSVFYNIAHMVLP-PEN | 93 |
| mSIR2α | 67 | LPDPQAMFDIEYFRKDPRPFFKFAKEIYP-GQF | 98 |
| CobB | 39 | VATPEGFARNPGLVQT---FYNARRQQLQQPEI | 68 |

| | | | |
|---|---|---|---|
| ySIR2 | 94 | IYSPLHSFIKMLQM-KGKLLRNYTQNIDNLESY | 125 |
| yHST1 | 94 | MYSPLHSFIKMLQD-KGKLLRNYTQNIDNLESY | 125 |
| mSIR2α | 99 | QPSLCHKFIALSDK-EGKLLRNYTQNIDTLEQV | 130 |
| CobB | 69 | QPNAAHLALANLKKRLAIAFLLVTQNIDNLHER | 101 |

| | | | |
|---|---|---|---|
| ySIR2 | 126 | AGISTDKLVQCHGSFATATCVTCHWNLPGERIF | 158 |
| yHST1 | 126 | AGIDPDKLVQCHGSFATASCVTCHWQIPGEKIF | 158 |
| mSIR2α | 131 | AGIQ--RILQCHGSFATASCLICKYKVDCEAVR | 161 |
| CobB | 102 | AGNR--NIIQMHGELLKVRCSQSGQILEWNGDV | 132 |

| | | | |
|---|---|---|---|
| ySIR2 | 159 | NKIRNLELPLCPYCYKKRREYFPEGYNNKVGVA | 191 |
| yHST1 | 159 | ENIRNLELPLCPYCYQKRKQYFPMSNGNNT--- | 188 |
| mSIR2α | 162 | GDIFNQVVPRCPRC------------P------ | 176 |
| CobB | 133 | MPEDKCHCCQFPAPLRPHVVWFG-EMP------ | 158 |

| | | | |
|---|---|---|---|
| ySIR2 | 192 | ASQGSMSERPPYILNSYGVLKPDITFFGEALPN | 224 |
| yHST1 | 189 | -VQTNINFNSP-ILKSYGVLKPDMTFFGEALPS | 219 |
| mSIR2α | 177 | ------A--DEP-----LAIMKPEIVFFGENLPE | 197 |
| CobB | 159 | -----LGMDEIYMALSMADIFIALGTSGHVYPA | 186 |

| | | | |
|---|---|---|---|
| ySIR2 | 225 | K--FHKSIREDILECDLLIC---IGTSLKVAPV | 252 |
| yHST1 | 220 | R--FHKTIRKDILECDLLIC---IGTSLKVAPV | 247 |
| mSIR2α | 198 | Q--FHRAMKYDKDEVDLLIV---IGSSLKVRPV | 225 |
| CobB | 187 | AGFVHEAKLHGAHTVELNLEPSQVGNEFEEKHY | 219 |

| | | | |
|---|---|---|---|
| ySIR2 | 253 | SEIVNMVPSHVPQILINRDP | 272 |
| yHST1 | 248 | SEIVNMVPSHVPQILINRDM | 267 |
| mSIR2α | 226 | ALIPSSIPHEVPQILINREP | 245 |
| CobB | 220 | GPASQVVPEFVDKFLKGL-- | 237 |

Fig. 2C

```
mSIR2α  249  IVLTGAGVSVSCGIPDFRSRDGIYARLAVDFPD
ySIR2   258  LVLTGAGVSTSLGIPDFRSSEGFYS--KIKHLG mSIR2α  282  LPDPQAMFDIEYFRKDPRPFFKFAKEIYP-GQF
ySIR2   289  LDDPQDVFNYNIFMHDPSVFYNIANMVLP-PEK mSIR2α  314  QPSLCHKFIALSDK-EGKLLRNYTQNIDTLEQV
ySIR2   321  IYSPLHSFIKMLQM-KGKLLRNYTQNIDNLESY mSIR2α  346  AGIQ--RILQCHGSFATASCLICKYKVDCEAVR
ySIR2   353  AGISTDKLVQCHGSFATATCVTCHWNLPGERIF
```

```
  1  MADEVALALQAAGSPSAAAAMEAASQPADEPLRKRPRRDG
 41  PGLGRSPGEPSAAVAPAAAGCEAASAAAPAALWREAAGAA
 81  ASAEREAPATAVAGDGDNGSGLRREPRAADDFDDDEGEEE
121  DEAAAAAAAAAIGYRDNLLLTDGLLTNGFHSCESDDDDRT
161  SHASSSDWTPRPRIGPYTFVQQHLMIGTDPRTILKDLLPE
201  TIPPPELDDMTLWQI VINILSEPPKRKKRKDINTIEDAVK
241  LLQECKKIIVLTGAGVSVSCGIPDFRSRDGIYARLAVDFP
281  DLPDPQAMFDIEYFRKDPRPFFKFAKEIYPGQFQPSLCHK
321  FIALSDKEGKLLRNYTQNIDTLEQVAGIQRILQCHGSFAT
361  ASCLICKYKVDCEAVRGDIFNQVVPRCPRCPADEPLAIMK
401  PEIVFFGENLPEQFHRAMKYDKDEVDLLIVIGSSLKVRPV
441  ALIPSSIPHEVPQILINREP LPHLHFDVELLGDCDVIINE
481  LCHRLGGEYAKLCCNPVKLSEITEKPPRPQKELVHLSELP
521  PTPLHISEDSSPERTVPQDSSVIATLVDQATNNNVNDLE
561  VSESSCVEEKPQEVQTSRNVENINVENPDFKAVGSSTADK
601  NERTSVAETVRKCWPNRLAKEQISKRLEGNQYLFVPPNRY
641  IFHGAEVYSDSEDDVLSSSSCGSNSDSGTCQSPSLEEPLE
681  DESEIEEFYNGLEDDTERPECAGGSGFGADGGDQEVVNEA
721  IATRQELTDVNYPSDKS
```

Fig. 12A

```
ySIR2    227  AINKVLCT--RLRLSNFFTIDHFIQKLHTARKI              257
mSIR2α   231  VINILSEPPKRKKRKDINTIEDAVKLLQECKKI              263
CobB       1  -------------------------MMENPRV                 7

▼       ▼▼    ▼
ySIR2    258  LVLTGAGVSTSLGIPDFRSSEGFYSKLKHLG--              288
mSIR2α   264  IVLTGAGVSVSCGIPDFRSRDGIYARLAVDFPD              296
CobB       8  LVLTGAGISAESGIRTFRAADGLWEEHRVED--               38 ySIR2    289  LDDPQDVFNYNIFMHDPSVFYNIANMVLPPEKI              321
mSIR2α   297  LPDPQAMFDIEYFRKDPRPFFKFAKEIYPGQFQ              329
CobB      39  VATPEGFARNPGLVQT--RYNARRQQLQQPEIQ               89

▼▼
ySIR2    322  YSPLHSFIKMLQM-KGKLLRNYTQNIDNLESYA              353
mSIR2α   330  PSLCHKFIALSDK-EGKLLRNYTQNIDTLEQVA              361
CobB      70  RNAAHLALANLKKRLAIAFLLVTQNIDNLHERA              102 ySIR2    354  GISTDKLVQCHGSFATATCVTCHWNLPGERIFN              386
mSIR2α   362  GIQ--RILQCHGSFATASCLICKYKVDCEAVRG              392
CobB     103  GNR--NIIQMHGELLKVRCSQSGQILEWN---G              130 ySIR2    387  KIRN-LELPLCPYCYKKRREYFPEGYNNKVGVA              418
mSIR2α   393  DIFN-QVVPRCPRCP-----------------               406
CobB     131  DVMP---EDKCHCCQ-----------------               142 ySIR2    419  ASQGSMSERPPYILNSYGVLKPDITFFGEALPN              451
mSIR2α   407  ------ADEP------LAIMKPEIVFFGENLPE              427
CobB     143  ------FPAP------L---RPHVWFGEMP--               158 ySIR2    452  KFHKSTREDILECDLLICIGTSLKVAPVS-ETV              483
mSIR2α   428  QFHRAMKYDKDEVDLLIVIGSSLKVRPVA-LIP              459
CobB     159  LGMDEIYMALSMADIFIAIGTSGHVYPAAGFVH              191 ySIR2    484  NMVPSHVPQVLINHDP-VKHAEFDLSLLGYCDD              515
mSIR2α   460  SSIPHEVPQILINREP-LPHLHFDVELLGDCDV              491
CobB     192  EAKLHGAHTVELNLEPSQVGNEFEEKHYGPASQ              224 ySIR2    516  IAAMVAQKCGWTIPHKKWNDLKNKNFKCQEKDK              548
mSIR2α   492  IINELCHRLGGEYAKLCCNPVKLSEITEKPPRP              524
CobB     225  VVPEFVDKFLKGL-------------------               237 ySIR2    549  GVYVVTSDEHPKTL-----------------                562
mSIR2α   525  QKELVHLSELPPTPLHISEDSSSPERTVPQDSS              557
CobB       0  -------------------------------                237
```

Fig. 14A

| Mutant | ADP-Rib. Activity (% of wt) | Deacetylase Activity (% of wt) | HM Silencing | Telomere Silencing | rDNA Silencing | rDNA Recombination | Mean Life Span (HML+) |
|---|---|---|---|---|---|---|---|
| sir2Δ | 0% | 2.7% | - | - | - | 1.15% | 11.4 |
| wildtype | 100% | 100% | + | + | + | 0.09% | 24.4 |
| Thr-261 | 4% | 17% | + | + | + | 0.09% | 19.8 |
| Gly-270 | 7% | 80% | + | +/- | + | 0.08% | 18.9 |
| Iso-271 | 8% | 36% | + | - | +/- | 0.22% | ND |
| Arg-275 | 100% | 67% | - | - | - | 1.03% | ND |
| Arg-345 | 0% | 3% | - | - | - | 1.22% | ND |
| Asp-347 | 0% | 3% | - | ND | ND | ND | ND |

Fig. 18

```
ySIR2      257 ILVLTGAGVSTSLGIPDFRS-SEGFYSKIKH--  286
yHST1      203 ILVLTGAGVSTSLGIPDFRS-SEGFYSKIRH--  232
yHST2       27 VIFMVGAGISTSCGIPDFRSPGTGLYHNLAR--   57
yHST3       55 IACLTGAGISCNAGIPDFRS-SDGLYDLVKKDC   86
yHST4       95 MVVVSGAGISVAAGIPDFRS-SEGIFSTVNGGS  126
mSIR2alpha 263 IIVLTGAGVSVSCGIPDFRS-RDGIVARLAVDF  294
mSIR2beta   79 VICLVGAGISTSAGIPDFRSPSTGLYANLEK--  109
mSIR2g...    1 --------------------GTRLYSNLQQ--   10
AI465098    48 VVFHTGAGISTASGIPDFRG-PHGVWTMEER--   77
AI465820    67 LLVMTGAGISTESGIPDYRSEKVGLYARTDR--   97
AI466061    59 IAITSGAGVSAESGVPTFRG-AGGYWRKWQA--   88 ySIR2      287 ---LGLDDPQDVFNYNIFMHDPSV--FYNIANM  314
yHST1      233 ---LGLEDPQDVFNLDIFLQDPSV--FYNIAHM  260
yHST2       58 ---LKLPYPEAVFDVDFFQSDPLP--FYTLAKE   85
yHST3       87 SQYWSIKSGREMFDISLFRDDFKTSIFAKFMER  119
yHST4      127 ---GKDLFDYNRVYGDESMSLKFN--QLMVSLF  154
mSIR2alpha 295 ---PDLPDPQAMFDIEYFRKDFRP--FFKFAKE  322
mSIR2beta  110 ---VHLPYPEAIFEISYFKKHPEP--FFALAKE  137
mSIR2g...   11 ---YDIPYPEAIFELGFFFHNPKP--FFMLAKE   38
AI465098    78 ---GLAPKFDTTFENA---------------   90
AI465820    98 -----RPIQ--HIDFVPVLRSASG--------  114
AI466061    89 ---QDLATPQAFARNPSQVWEFYH-----YRRE  113 ySIR2      315 VLP--PEKIYSPLHSFIKMLQMKGKLLRNYTQN  345
yHST1      261 VLP--PENMYSPLHSFIKMLQDKGKLLRNYTQN  291
yHST2       86 LYP--GNFRPSKFHYLLKLFQDKDVLKRVYTQN  116
yHST3      120 LYSNVQLAKPTKTHKFIAHLKDRNKLLRCYTQN  152
yHST4      155 RLS--KNCQPTKFHEMLNEFARDGRLLRLYTQN  185
mSIR2alpha 323 IYP--GQFGPSLCHKFIALSDKEGKLLRNYTQN  353
mSIR2beta  138 LYP--GQFKPTICHYFIRLLKEKGLLLRCYTQN  168
mSIR2g...   39 LYP--GHYRPNVTHYFLRLLHDKELLLRLYTQN   69
AI465098    91 ------R--PSKTHMALVQLERMGFLSFLVSQN  115
AI465820   115 TWP--ENLWAGLNSPLTNPTQHTWL-------  137
AI466061   114 VMR--SK-EPNPGHLAIAQCEAR---------  133 ySIR2      346 IDNLESYAGISTD--------------KLVQ   362
yHST1      292 IDNLESYAGIDPD--------------KLVQ   308
yHST2      117 IDTLERQAGVKDD--------------LIIE   133
yHST3      153 IDGLEESIGLTLSNRKLPLTSFSSHWKNLDVVQ  185
yHST4      186 IDGLDTQLPHLSTN------VPLAKPIPSTVQ  211
mSIR2alpha 354 IDTLEQVAGIQR---------------ILQ   368
mSIR2beta  169 IDTLERVAGLEPQ--------------DLVE   185
mSIR2g...   70 IDGLERASGIPAS--------------KLVE    86
AI465098   116 VDGLDVRSGFRRD--------------KLAE   132
AI465820     0 --------------------------------  137
AI466061     0 --------------------------------  133
```

Fig. 19

```
            10          20          30          40          50          60
GCGGAGCAGAGGAGGCGAGGGCGGAGGGCCAGAGAGGCAGTTGGAAGATGGCGGACGAGG
                                                  M  A  D  E  V 70          80          90         100         110         120
TGGCGCTCGCCCTTCAGGCCGCCGGCTCCCCTTCCGCGGCGGCCGCCATGGAGGCCGCGT
 A  L  A  L  Q  A  A  G  S  P  S  A  A  A  A  M  E  A  A  S 130         140         150         160         170         180
CGCAGCCGGCGGACGAGCCGCTCCGCAAGAGGCCCCGCCGAGACGGGCCTGGCCTCGGGC
 Q  P  A  D  E  P  L  R  K  R  P  R  R  D  G  P  G  L  G  R 190         200         210         220         230         240
GCAGCCCGGGCGAGCCGAGCGCAGCAGTGGCGCCGGCGGCCGCGGGGTGTGAGGCGGCGA
 S  P  G  E  P  S  A  A  V  A  P  A  A  A  G  C  E  A  A  S 250         260         270         280         290         300
GCGCCGCGGCCCCGGCGGCGCTGTGGCGGGAGGCGGCAGGGGCGGCGGCGAGCGCGGAGC
 A  A  A  P  A  A  L  W  R  E  A  A  G  A  A  A  S  A  E  R 310         320         330         340         350         360
GGGAGGCCCCGGCGACGGCCGTGGCCGGGGACGGAGACAATGGGTCCGGCCTGCGGCGGG
 E  A  P  A  T  A  V  A  G  D  G  D  N  G  S  G  L  R  R  E 370         380         390         400         410         420
AGCCGAGGGCGGCTGACGACTTCGACGACGACGAGGGCGAGGAGGAGGACGAGGCGGCGG
 P  R  A  A  D  D  F  D  D  D  E  G  E  E  E  D  E  A  A  A 430         440         450         460         470         480
CGGCAGCGGCGGCGGCAGCGATCGGCTACCGAGACAACCTCCTGTTGACCGATGGACTCC
 A  A  A  A  A  A  I  G  Y  R  D  N  L  L  L  T  D  G  L  L 490         500         510         520         530         540
TCACTAATGGCTTTCATTCCTGTGAAAGTGATGACGATGACAGAACGTCACACGCCAGCT
 T  N  G  F  H  S  C  E  S  D  D  D  D  R  T  S  H  A  S  S 550         560         570         580         590         600
CTAGTGACTGGACTCCGCGGCCGCGGATAGGTCCATATACTTTTGTTCAGCAACATCTCA
 S  D  W  T  P  R  P  R  I  G  P  Y  T  F  V  Q  Q  H  L  M 610         620         630         640         650         660
TGATTGGCACCGATCCTCGAACAATTCTTAAAGATTTATTACCAGAAACAATTCCTCCAC
 I  G  T  D  P  R  T  I  L  K  D  L  L  P  E  T  I  P  P  P 670         680         690         700         710         720
CTGAGCTGGATGATATGACGCTGTGGCAGATTGTTATTAATATCCTTTCAGAACCACCAA
 E  L  D  D  M  T  L  W  Q  I  V  I  N  I  L  S  E  P  P  K 730         740         750         760         770         780
AGCGGAAAAAAGAAAAGATATCAATACAATTGAAGATGCTGTGAAGTTACTGCAGGAGT
 R  K  K  R  K  D  I  N  T  I  E  D  A  V  K  L  L  Q  E  C 790         800         810         820         830         840
GTAAAAAGATAATAGTTCTGACTGGAGCTGGGGTTTCTGTCTCCTGTGGGATTCCTGACT
 K  K  I  I  V  L  T  G  A  G  V  S  V  S  C  G  I  P  D  F 850         860         870         880         890         900
TCAGATCAAGAGACGGTATCTATGCTCGCCTTGCGGTGGACTTCCCAGACCTCCCAGACC
 R  S  R  D  G  I  Y  A  R  L  A  V  D  F  P  D  L  P  D  P
```

Fig. 21A

```
            910       920       930       940       950       960
         CTCAAGCCATGTTTGATATTGAGTATTTTAGAAAAGACCCAAGACCATTCTTCAAGTTTG
           Q  A  M  F  D  I  E  Y  F  R  K  D  P  R  P  F  F  K  F  A 970       980       990      1000      1010      1020
         CAAAGGAAATATATCCCGGACAGTTCCAGCCGTCTCTGTGTCACAAATTCATAGCTTTGT
           K  E  I  Y  P  G  Q  F  Q  P  S  L  C  H  K  F  I  A  L  S 1030      1040      1050      1060      1070      1080
         CAGATAAGGAAGGAAAACTACTTCGAAATTATACTCAAAATATAGATACCTTGGAGCAGG
           D  K  E  G  K  L  L  R  N  Y  T  Q  N  I  D  T  L  E  Q  V 1090      1100      1110      1120      1130      1140
         TTGCAGGAATCCAAAGGATCCTTCAGTGTCATGGTTCCTTTGCAACAGCATCTTGCCTGA
           A  G  I  Q  R  I  L  Q  C  H  G  S  F  A  T  A  S  C  L  I 1150      1160      1170      1180      1190      1200
         TTTGTAAATACAAAGTTGATTGTGAAGCTGTTCGTGGAGACATTTTTAATCAGGTAGTTC
           C  K  Y  K  V  D  C  E  A  V  R  G  D  I  F  N  Q  V  V  P 1210      1220      1230      1240      1250      1260
         CTCGGTGCCCTAGGTGCCCAGCTGATGAGCCACTTGCCATCATGAAGCCAGAGATTGTCT
           R  C  P  R  C  P  A  D  E  P  L  A  I  M  K  P  E  I  V  F 1270      1280      1290      1300      1310      1320
         TCTTTGGTGAAAACTTACCAGAACAGTTTCATAGAGCCATGAAGTATGACAAAGATGAAG
           F  G  E  N  L  P  E  Q  F  H  R  A  M  K  Y  D  K  D  E  V 1330      1340      1350      1360      1370      1380
         TTGACCTCCTCATTGTTATTGGATCTTCTCTGAAAGTGAGACCAGTAGCACTAATTCCAA
           D  L  L  I  V  I  G  S  S  L  K  V  R  P  V  A  L  I  P  S 1390      1400      1410      1420      1430      1440
         GTTCTATACCCCATGAAGTGCCTCAAATATTAATAAATAGGGAACCTTTGCCTCATCTAC
           S  I  P  H  E  V  P  Q  I  L  I  N  R  E  P  L  P  H  L  H 1450      1460      1470      1480      1490      1500
         ATTTTGATGTAGAGCTCCTTGGAGACTGCGATGTTATAATTAATGAGTTGTGTCATAGGC
           F  D  V  E  L  L  G  D  C  D  V  I  I  N  E  L  C  H  R  L 1510      1520      1530      1540      1550      1560
         TAGGTGGTGAATATGCCAAACTTTGTTGTAACCCTGTAAAGCTTTCAGAAATTACTGAAA
           G  G  E  Y  A  K  L  C  C  N  P  V  K  L  S  E  I  T  E  K 1570      1580      1590      1600      1610      1620
         AACCTCCACGCCCACAAAAGGAATTGGTTCATTTATCAGAGTTGCCACCAACACCTCTTC
           P  P  R  P  Q  K  E  L  V  H  L  S  E  L  P  P  T  P  L  H 1630      1640      1650      1660      1670      1680
         ATATTTCGGAAGACTCAAGTTCACCTGAAAGAACTGTACCACAAGACTCTTCTGTGATTG
           I  S  E  D  S  S  S  P  E  R  T  V  P  Q  D  S  S  V  I  A 1690      1700      1710      1720      1730      1740
         CTACACTTGTAGACCAAGCAACAAACAACAATGTTAATGATTTAGAAGTATCTGAATCAA
           T  L  V  D  Q  A  T  N  N  N  V  N  D  L  E  V  S  E  S  S
```

Fig. 21B

```
        1750      1760      1770      1780      1790      1800
GTTGTGTGGAAGAAAAACCACAAGAAGTACAGACTAGTAGGAATGTTGAGAACATTAATG
   C  V  E  E  K  P  Q  E  V  Q  T  S  R  N  V  E  N  I  N  V 1810      1820      1830      1840      1850      1860
TGGAAAATCCAGATTTTAAGGCTGTTGGTTCCAGTACTGCAGACAAAAATGAAAGAACTT
   E  N  P  D  F  K  A  V  G  S  S  T  A  D  K  N  E  R  T  S 1870      1880      1890      1900      1910      1920
CAGTTGCAGAAACAGTGAGAAAATGCTGGCCTAATAGACTTGCAAAGGAGCAGATTAGTA
   V  A  E  T  V  R  K  C  W  P  N  R  L  A  K  E  Q  I  S  K 1930      1940      1950      1960      1970      1980
AGCGGCTTGAGGGTAATCAATACCTGTTTGTACCACCAAATCGTTACATATTCCACGGTG
   R  L  E  G  N  Q  Y  L  F  V  P  P  N  R  Y  I  F  H  G  A 1990      2000      2010      2020      2030      2040
CTGAGGTATACTCAGACTCTGAAGATGACGTCTTGTCCTCTAGTTCCTGTGGCAGTAACA
   E  V  Y  S  D  S  E  D  D  V  L  S  S  S  S  C  G  S  N  S 2050      2060      2070      2080      2090      2100
GTGACAGTGGCACATGCCAGAGTCCAAGTTTAGAAGAACCCTTGGAAGATGAAAGTGAAA
   D  S  G  T  C  Q  S  P  S  L  E  E  P  L  E  D  E  S  E  I 2110      2120      2130      2140      2150      2160
TTGAAGAATTCTACAATGGCTTGGAAGATGATACGGAGAGGCCCGAATGTGCTGGAGGAT
   E  E  F  Y  N  G  L  E  D  D  T  E  R  P  E  C  A  G  G  S 2170      2180      2190      2200      2210      2220
CTGGATTTGGAGCTGATGGAGGGGATCAAGAGGTTGTTAATGAAGCTATAGCTACAAGAC
   G  F  G  A  D  G  G  D  Q  E  V  V  N  E  A  I  A  T  R  Q 2230      2240      2250      2260      2270      2280
AGGAATTGACAGATGTAAACTATCCATCAGACAAATCATAACACTATTGAAGCTGTCCGG
   E  L  T  D  V  N  Y  P  S  D  K  S  *

2290      2300      2310      2320      2330      2340
ATTCAGGAATTGCTCCACCAGCATTGGGAACTTTAGCATGTCAAAAAAATGAATGTTTAC 2350      2360      2370      2380      2390      2400
TTGTGAACTTGAACAAGGAAATCTGAAAGATGTATTATTTATAGACTGGAAAATAGATTG 2410      2420      2430      2440      2450      2460
TCTTCTTGGATAATTTCTAAAGTTCCATCATTTCTGTTTGTACTTGTACATTCAACACTG 2470      2480      2490      2500      2510      2520
TTGGTTGACTTCATCTTCCTTTCAAGGTTCATTTGTATGATACATTCGTATGTATGTATA 2530      2540      2550      2560      2570      2580
ATTTTGTTTTTTGCCTAATGAGTTTCAACCTTTTAAAGTTTTCAAAAGCCATTGGAATGT 2590      2600      2610      2620      2630      2640
TAATGTAAAGGGAACAGCTTATCTAGACCAAAGAATGGTATTTCACACTTTTTTGTTTGT 2650      2660      2670      2680      2690      2700
AACATTGAATAGTTTAAAGCCCTCAATTTCTGTTCTGCTGAACTTTTATTTTTAGGACAG
```

Fig. 21C

```
       2710      2720      2730      2740      2750      2760
TTAACTTTTTAAACACTGGCATTTTCCAAAACTTGTGGCAGCTAACTTTTTAAAATCACA
       2770      2780      2790      2800      2810      2820
GATGACTTGTAATGTGAGGAGTCAGCACCGTGTCTGGAGCACTCAAAACTTGGGCTCAGT
       2830      2840      2850      2860      2870      2880
GTGTGAAGCGTACTTACTGCATCGTTTTGTACTTGCTGCAGACGTGGTAATGTCCAAAC
       2890      2900      2910      2920      2930      2940
AGGCCCCTGAGACTAATCTGATAAATGATTTGGAAATGTGTTTCAGTTGTTCTAGAAACA
       2950      2960      2970      2980      2990      3000
ATAGTGCCTGTCTATATAGGTCCCCTTAGTTTGAATATTTGCCATTGTTTAATTAAATAC
       3010      3020      3030      3040      3050      3060
CTATCACTGTGGTAGAGCCTGCATAGATCTTCACCACAAATACTGCCAAGATGTGAATAT
       3070      3080      3090      3100      3110      3120
GCAAAGCCTTTCTGAATCTAATAATGGTACTTCTACTGGGGAGAGTGTAATATTTTGGAC
       3130      3140      3150      3160      3170      3180
TGCTGTTTTTCCATTAATGAGGAAAGCAATAGGCCTCTTAATTAAAGTCCCAAAGTCATA
       3190      3200      3210      3220      3230      3240
AGATAAATTGTAGCTCAACCAGAAAGTACACTGTTGCCTGTTGAGGATTTGGTGTAATGT
       3250      3260      3270      3280      3290      3300
ATCCCAAGGTGTTAGCCTTGTATTATGGAGATGAATACAGATCCAATAGTCAAATGAAAC
       3310      3320      3330      3340      3350      3360
TAGTTCTTAGTTATTTAAAAGCTTAGCTTGCCTTAAAACTAGGGATCAATTTTCTCAACT
       3370      3380      3390      3400      3410      3420
GCAGAAACTTTTAGCCTTTCAAACAGTTCACACCTCAGAAAGTCAGTATTTATTTTACAG
       3430      3440      3450      3460      3470      3480
ACTTCTTTGGAACATTGCCCCCAAATTTAAATATTCATGTGGGTTTAGTATTTATTACAA
       3490      3500      3510      3520      3530      3540
AAAAATGATTTGAAATATAGCTGTTCTTTATGCATAAAATACCCAGTTAGGACCATTACT
       3550      3560      3570      3580      3590      3600
GCCAGAGGAGAAAAGTATTAAGTAGCTCATTTCCCTACCTAAAAGATAACTGAATTTATT
       3610      3620      3630      3640      3650      3660
TGGCTACACTAAAGAATGCAGTATATTTAGTTTTCCATTTGCATGATGTGTTTGTGCTAT
       3670      3680      3690      3700      3710      3720
AGACAATATTTTAAATTGAAAAATTTGTTTTAAATTATTTTACAGTGAAGACTGTTTTC
       3730      3740      3750      3760      3770      3780
AGCTCTTTTTATATTGTACATAGACTTTTATGTAATCTGGCATATGTTTTGTAGACCGTT
       3790      3800      3810      3820      3830      3840
TAATGACTGGATTATCTTCCTCCAACTTTTGAAATACAAAAACAGTGTTTTATACTAAAA
       3850      3860      3870
AAAAAAAAAGTCGACGCGGCCGCGAATTC
```

Fig. 21D

```
         10        20        30        40        50        60
CCACGCGTCCGCGGACGCGTGGGCACGGGACAGAGCAGTCGGTGACAGTCCCGAGGGCCC
  T  R  P  R  T  R  G  H  G  T  E  Q  S  V  T  V  P  R  A  P 70        80        90       100       110       120
CCACCCCGTTCCCATGGCCGAGCCGGACCGATTCAGACTCGGACACTGAGGGAGGAGCCA
  T  P  F  P  W  P  S  R  T  D  S  D  S  D  T  E  G  G  A  T 130       140       150       160       170       180
CTGGTGGAGAGGCAGAGATGGACTTCCTGAGGAATTTATTCACCCAGACCCTGGGCCTGG
  G  G  E  A  E  M  D  F  L  R  N  L  F  T  Q  T  L  G  L  G 190       200       210       220       230       240
GTTCCCAAAAGGAGCGTCTTCTAGACGAGCTGACCCTCGAAGGAGTGACACGCTACATGC
  S  Q  K  E  R  L  L  D  E  L  T  L  E  G  V  T  R  Y  M  Q 250       260       270       280       290       300
AGAGCGAGCGCTGCCGCAAGGTCATCTGTTTGGTGGGAGCCGGAATCTCCACGTCCGCGG
  S  E  R  C  R  K  V  I  C  L  V  G  A  G  I  S  T  S  A  G 310       320       330       340       350       360
GTATCCCTGACTTCCGCTCCCCGTCCACTGGCCTCTATGCAAACCTGGAGAAGTACCACC
  I  P  D  F  R  S  P  S  T  G  L  Y  A  N  L  E  K  Y  H  L 370       380       390       400       410       420
TTCCTTACCCAGAGGCCATCTTTGAGATCAGCTACTTCAAGAAACATCCGGAACCCTTCT
  P  Y  P  E  A  I  F  E  I  S  Y  F  K  K  H  P  E  P  F  F 430       440       450       460       470       480
TTGCCCTTGCCAAGGAGCTCTATCCCGGGCAGTTCAAGCCAACCATCTGCCACTACTTCA
  A  L  A  K  E  L  Y  P  G  Q  F  K  P  T  I  C  H  Y  F  I 490       500       510       520       530       540
TCCGCCTGCTGAAGGAGAAGGGGCTGCTGCTGCGCTGCTACACGCAGAACATAGACACGC
  R  L  L  K  E  K  G  L  L  L  R  C  Y  T  Q  N  I  D  T  L 550       560       570       580       590       600
TGGAACGAGTGGCGGGGCTGGAGCCCCAGGACCTGGTGGAGGCCCACGGCACCTTCTACA
  E  R  V  A  G  L  E  P  Q  D  L  V  E  A  H  G  T  F  Y  T 610       620       630       640       650       660
CATCACACTGTGTCAACACCTCCTGCAGAAAAGAATACACGATGGGCTGGATGAAAGAGA
  S  H  C  V  N  T  S  C  R  K  E  Y  T  M  G  W  M  K  E  K 670       680       690       700
AGATTTCTCAGAAGCAACTCCCAGGTGTGAGCAGTGTCA
  I  S  Q  K  Q  L  P  G  V  S  S  V
```

Fig. 22

METHODS FOR IDENTIFYING AGENTS WHICH ALTER HISTONE PROTEIN ACETYLATION

GOVERNMENT SUPPORT

The invention was supported, in whole or in part, by grant AG 11119 from the National Institutes of Aging. The Government has certain rights in the invention.

BACKGROUND OF THE INVENTION

Aging involves progressive and irreversible loss of cellular processes and physiological functions that ultimately increase the likelihood of death. Molecular correlates of aging, including an increase in chromosomal structural abnormalities, the frequency of single-strand DNA breaks, a decline in DNA methylation, and a loss of DNA telomeric sequences, have been described in a range of eukaryotic organisms from mammals, such as humans, to unicellular organisms, such as yeast.

Although several mechanisms have been postulated as mediators of aging (e.g., somatic mutation theory, error catastrophe theory, intrinsic DNA rearrangement theory), none have led to interventions or therapies to slow aging and increase life span. In humans, declining health in aging individuals has a significant impact on the cost and implementation of geriatric health care.

Thus, there is a need to identify agents which alter (e.g., agonize, antagonize) the level of substrates and cellular mediators associated with the aging process. The identification of such agents is important in the development of specific and effective treatment regimens to decrease aging or increase the life span of a cell or an organism, and to further define pathways which lead to aging in a cell or organism.

SUMMARY OF THE INVENTION

The present invention relates to methods of altering the NAD-dependent acetylation status of proteins, e.g., histone proteins, identifying agents which alter the NAD-dependent acetylation status of proteins, e.g., histone proteins, identifying agents which alter mono-ADP-ribosylation of nuclear proteins, alter aging or alter life span, as well as to methods of altering mono-ADP-ribosylation of nuclear proteins, methods of altering aging of a cell or organism, and methods of altering life span of a cell or organism. In preferred embodiments, the invention relates to methods of identifying agents which alter the NAD-dependent acetylation status of histone proteins by altering the activity of Sir2, increase mono-ADP-ribosylation of nuclear histone proteins, decrease aging or increase life span in a cell or organism, as well as to methods of increasing mono-ADP-ribosylation, decreasing aging or increasing life span of a cell or organism. In preferred embodiments, increasing mono-ADP-ribosylation or NAD-dependent deacetylation of histone proteins, decreasing aging or increasing life span of a cell or organism comprise administering to the cell or organism Sir2 or a mono-ADP-ribosyltransferase or an agonist of Sir2 and/or mono-ADP-ribosyltransferase activity, and combinations thereof.

In one embodiment, the method of the invention is a method of altering the NAD-dependent acetylation status of at least one amino acid residue in a histone protein by altering the activity of a Sir2 protein or a Sir2-like protein. The histone protein can be selected from the group consisting of a H2B, H3 or H4 histone protein. In a preferred embodiment, the amino acid residue is a lysine amino acid residue. In a particularly preferred embodiment, the lysine amino acid residue is lysine 9 and/or lysine 14 of a H3 histone protein and/or lysine 16 of a H4 histone protein. The NAD-dependent acetylation status is removal of an acetyl group and/or addition of an acetyl group.

In a preferred embodiment, NAD-dependent acetylation status of the histone protein is altered by altering the activity of Sir2α protein. In another embodiment, the NAD-dependent acetylation status is altered by altering the activity of a mutant Sir2α protein selected from the group consisting of G253A, G255A, S257A, I262A, F265A, R266A, G270A, P285A, T336A, H355A, Thr-261, Iso-271, Arg-275, Asn-345 or Asp-347.

In another embodiment, the invention relates to a method of identifying an agent which alters the activity of a Sir2 protein or a Sir2-like protein by assessing the NAD-dependent acetylation status of at least one amino acid in a histone protein, comprising combining the histone protein, the Sir2 protein or the Sir2-like protein, NAD or a NAD-like compound and the agent to be tested, thereby producing a combination; detecting the NAD-dependent acetylation status of an amino acid in the histone protein; and comparing the NAD-dependent acetylation status in the presence of the agent to be tested with the NAD-dependent acetylation status of the amino acid in the histone protein in the absence of the agent to be tested, wherein a difference in the NAD-dependent acetylation status of the amino acid of the histone protein between the presence of the agent and the absence of the agent indicates that the agent alters the NAD-dependent acetylation status of at least one amino acid of the histone protein.

Another aspect of the invention relates to a method of identifying an agent which alters life span of a cell by assessing the NAD-dependent acetylation status of at least one amino acid in a histone protein, comprising combining the histone protein, a Sir2 protein or Sir2-like protein, NAD or a NAD-like compound and the agent to be tested, thereby producing a combination; detecting the NAD-dependent acetylation status of an amino acid in the histone protein; and comparing the NAD-dependent acetylation status in the presence of the agent to be tested with the acetylation status of the amino acid in the histone protein in the absence of the agent to be tested, wherein a difference in the acetylation status of the amino acid of the histone protein between the presence of the agent alters the life span of the cell. The invention further relates to administering the agents identified by the method to a cell and assessing the NAD-dependent acetylation status of at least one amino acid in a histone protein of the cell.

In a further embodiment, the invention relates to a method of identifying an agent which alters the activity of a Sir2 protein or a Sir2-like protein by assessing the NAD-dependent acetylation status of at least one amino acid in a histone protein, comprising combining the histone protein, the Sir2 protein or the Sir2-like protein, NAD or a NAD-like compound and the agent to be tested, thereby producing a combination; detecting the NAD-dependent acetylation status of an amino acid in the histone protein; and comparing the NAD-dependent acetylation status in the presence of the agent to be tested with the NAD-dependent acetylation status of the amino acid in the histone protein in the absence of the agent to be tested, wherein a difference in the NAD-dependent acetylation status of the amino acid of the histone protein between the presence of the agent and the absence of the agent indicates that the agent alters the NAD-dependent acetylation status of at least one amino acid of the histone protein.

In yet another embodiment, the invention relates to a method of identifying an agent which alters aging of a cell by assessing the NAD-dependent acetylation status of at least one amino acid in a histone protein, comprising combining the histone protein, a Sir2 protein or Sir2-like protein, NAD or a NAD-like compound and the agent to be tested, thereby producing a combination; detecting the NAD-dependent acetylation status of an amino acid in the histone protein; and comparing the NAD-dependent acetylation status in the presence of the agent to be tested with the acetylation status of the amino acid in the histone protein in the absence of the agent to be tested, wherein a difference in the acetylation status of the amino acid of the histone protein between the presence of the agent alters aging of the cell. In one embodiment, the agent increases aging of the cell. In another embodiment, the agent decreases aging of the cell.

In another embodiment, the invention relates to a method of altering the NAD-dependent acetylation status of at least one amino acid residue in a histone protein comprising combining the histone protein, a Sir2 protein or Sir2-like protein and a NAD or a NAD-like compound.

In yet another embodiment, the methods of the invention include methods for identifying an agent which alters mono-ADP-ribosylation of a nuclear protein in a cell or an organism, comprising combining a cell or organism and an agent to be tested; determining a level of mono-ADP-ribosylation of a nuclear protein in the cell or in one or more cells of the organism; and comparing the level of mono-ADP-ribosylation in the presence of the agent with the level of mono-ADP-ribosylation of the nuclear protein in the absence of the agent. A difference in the level of mono-ADP-ribosylation of the nuclear protein in the presence of the agent as compared with in the absence of the agent indicates that the agent alters mono-ADP-ribosylation of the nuclear protein. In a preferred embodiment, the agent is an agonist of mono-ADP-ribosylation. In another embodiment, the agent is an antagonist of mono-ADP-ribosylation.

In another embodiment, the invention relates to methods for identifying an agent which alters life span of a cell or an organism, comprising combining a cell or organism and an agent to be tested; determining a level of mono-ADP-ribosylation of a nuclear protein in the cell or in one or more cells of the organism; and comparing the level of mono-ADP-ribosylation in the presence of the agent with the level of mono-ADP-ribosylation of the nuclear protein in the absence of the agent. A difference in the level of mono-ADP-ribosylation of the nuclear protein in the presence of the agent as compared with in the absence of the agent indicates that the agent alters mono-ADP-ribosylation of the nuclear protein, wherein agents which alter mono-ADP-ribosylation of nuclear proteins are agents which alter life span of a cell or an organism. In a preferred embodiment, the agent is an agonist of mono-ADP-ribosylation. In another embodiment, the agent is an antagonist of mono-ADP-ribosylation.

The invention also relates to a method of identifying an agent which increases life span of a cell or an organism, comprising the steps of combining a cell or organism and an agent to be tested; determining a level of mono-ADP-ribosylation of a nuclear protein in the cell or in one or more cells of the organism in the presence of the agent and in the absence of the agent; identifying an agent which increases mono-ADP-ribosylation of a nuclear protein; administering said agent to a cell or an organism; and determining the life span of said cell, wherein an agent which increases the life span of said cell or organism relative to the mean life span of said cell or organism or relative to the life span of said cell or organism in the absence of the agent is an agent which increases life span of a cell or organism.

The invention also relates to a method of identifying an agent which decreases life span of a cell or an organism, comprising the steps of combining a cell or organism and an agent to be tested; determining a level of mono-ADP-ribosylation of a nuclear protein in the cell or in one or more cells of the organism in the presence of the agent and in the absence of the agent; identifying an agent which decreases mono-ADP-ribosylation of a nuclear protein; administering said agent to a cell or an organism; and determining the life span of said cell, wherein an agent which decreases the life span of said cell or organism relative to the mean life span of said cell or organism or relative to the life span of said cell or organism in the absence of the agent is an agent which decreases life span of a cell or organism.

Also encompassed by the present invention is a method of identifying an agent which alters aging of a cell, comprising the steps of combining a cell and an agent to be tested; determining a level of mono-ADP-ribosylation of a nuclear protein in the cell; and comparing the level of mono-ADP-ribosylation in the presence of the agent with a level of mono-ADP-ribosylation of the nuclear protein in the absence of the agent to be tested. A difference in the level of mono-ADP-ribosylation of the nuclear protein between the presence of the agent and the absence of the agent indicates that the agent alters aging of the cell. In particular embodiment, the agent decreases aging of the cell. In another embodiment, the agent increases aging of the cell.

Another aspect of the invention includes a method of increasing the life span of a cell, comprising administering to the cell an effective amount of an agent which increases mono-ADP-ribosylation of a nuclear protein. The agent to be administered is identified by a method comprising the steps of combining a cell and an agent to be tested; determining a level of mono-ADP-ribosylation of a nuclear protein in the cell; and comparing the level of mono-ADP-ribosylation in the presence of the agent with a level of mono-ADP-ribosylation of the nuclear protein in the absence of the agent to be tested, wherein in the presence of the agent there is an increase in the level of mono-ADP-ribosylation of the nuclear protein.

The invention also relates to a method of decreasing aging of a cell, comprising administering to the cell an effective amount of an agent which increases mono-ADP-ribosylation of a nuclear protein. The agent to be administered is identified by a method comprising the steps of combining a cell and an agent to be tested; determining a level of mono-ADP-ribosylation of a nuclear protein in the cell; and comparing the level of mono-ADP-ribosylation in the presence of the agent with a level of mono-ADP-ribosylation of the nuclear protein in the absence of the agent to be tested, wherein in the presence of the agent there is an increase in the level of mono-ADP-ribosylation of the nuclear protein.

The invention further pertains to a method of increasing the life span of a cell or an organism comprising administering to the cell or organism a mono-ADP-ribosyltransferase or an agonist of mono-ADP-ribosyltransferase activity in an amount effective to increase the life span of the cell or organism.

In yet another embodiment, the present invention pertains to a method of increasing the life span of a cell or organism comprising administering to the cell or organism an agonist of mono-ADP-ribosylation of histone protein H2B in an amount effective to increase the life span of the cell or organism.

Another embodiment of the invention pertains to a method of decreasing aging of a cell or organism comprising administering to the cell or organism a mono-ADP-ribosyltransferase or an agonist of mono-ADP-ribosyltransferase activity in an amount effective to decrease aging of the cell or organism.

Also encompassed by the present invention is a method of decreasing aging of a cell or organism comprising administering to the cell or organism an agonist of mono-ADP-ribosylation of histone protein H2B in an amount effective to decrease aging of the cell or organism.

The invention also relates to a method of inhibiting the formation, replication and/or accumulation of rDNA circles in a cell comprising administering to the cell a mono-ADP-ribosyltransferase or an agonist of mono-ADP-ribosyltransferase activity in an amount effective to inhibit the formation, replication and/or accumulation of rDNA circles.

Another aspect of the invention is a method for decreasing recombination between rDNA in a cell comprising administering to the cell a mono-ADP-ribosyltransferase or an agonist of mono-ADP-ribosyltransferase activity in an amount effective to decrease recombination between rDNA.

In a preferred embodiment, the nuclear protein in the methods of the present invention is selected from the group consisting of histone proteins H2A, H2B and H3. In particular, the mono-ADP-ribosylation of nuclear proteins is performed by the core domain of Sir2, the Sir2 protein, a fragment of the Sir2 protein (e.g., SEQ ID NOS: 1, 2, 4, 9, 10, 11, 12, 14, 19, 20, 21 or 26), or an agonist of Sir2.

In one embodiment of the methods described herein, the cell is a yeast cell. In another embodiment, the cell is a mammalian cell.

The present invention also provides an isolated murine Sir2 protein, preferably the murine Sir2α protein (SEQ ID NO: 26) and the nucleic acid sequence encoding the Sir2α (SEQ ID NO: 25).

The invention also pertains to isolated nucleic acid molecules of murine SIR2 genes operably linked to a regulatory sequence and methods of preparing Sir2 proteins by culturing the recombinant host cells comprising isolated nucleic acid molecules of murine SIR2 genes.

Also encompassed by the present invention, are antibodies, or antigen-binding fragments thereof, which selectively bind a murine Sir2 proteins or a murine Sir2-like protein.

The invention described herein provides novel methods to readily identify agents that alter the NAD-dependent acetylation status of nuclear proteins and/or the mono-ADP-ribosylation of a nuclear protein; and to utilize the identified agents to alter NAD-dependent acetylation, ADP-ribosylation, aging and increase life span. For example, the invention provides unique and efficient ways to forestall senescence and extend life in cells and organisms.

BRIEF DESCRIPTION OF THE FIGURES

FIG. 2A is the deduced amino acid sequence of mSir2α (SEQ ID NO: 1) with the predicted nuclear localization signal underlined.

FIG. 2B is a Western blot of the mSir2α protein (120 kD) immunoprecipitated (IP) from cell extracts of murine NIH3T3 cells and in vitro translated (IVF) probed with a polyclonal antibody against the N-terminal 131 amino acids of the protein (αmSir2α).

FIG. 2C is an alignment of the evolutionarily conserved core domains of yeast (ySir2, GenBank Accession Nos: X01419, M21316, SEQ ID NO: 2; yHST1, GenBank Accession Nos: U39041, L47120, SEQ ID NO: 3); murine (mSir2α, SEQ ID NO: 4) and *Salmonella* (CobB, GenBank Accession No: U89687, SEQ ID NO: 5) Sir2 proteins. Identical amino acids are boxed. A putative NAD binding cleft is indicated by asterisks. Less conserved amino acids are shaded.

FIG. 8a is a Coomassie blue-stained SDS-PAGE gel of purified recombinant yeast (rSir2p) protein, mouse Sir2 (mSir2α) proteins and vector controls. Full length proteins are indicated by dots.

FIGS. 8b, 8c, 8d, 8e and 8f are HPLC chromatograms showing absorbance at 220 nm of products of deacetylation assays with yeast Sir2p and the indicated concentrations of NAD. The efficiencies of the reactions are calculated from the areas under peaks 1, 2, and 4.

FIG. 8g is a schematic of contents of peaks 1-5 shown in chromatograms.

FIGS. 9a and 9b depict peak 3 of the HPLC chromatogram of the deacetylase reaction at 1 mM NAD. The molecular weights of the two products in peak 3 correspond to the starting peptide (2370) and the doubly deacetylated dimer (2-times the molecular weight of the starting peptide, 4740, minus the difference between the molecular weight of two acetyl moieties versus two hydrogens, 84, yielding 4656).

FIG. 9c Peak 4 of the same reaction. The molecular weight of peak 4 (4698) corresponds to singly deacetylated dimer peptide.

FIG. 9d Peak 5 of the same reaction corresponds to dimer peptide (molecular weight 4740).

FIG. 11d shows the ADP-ribosylated peptide indicated by a bracket on a longer exposure (left), and NAD and its hydrolysed product are indicated by an arrow and an arrowhead on a shorter exposure, respectively (right).

FIGS. 12a, 12b, and 12c show the deacetylation activity of the mouse Sir2p homolog, mSir2α.

FIG. 12a is the amino acid sequence of mSir2α (SEQ ID NO: 1). The evolutionarily conserved core domain of mSir2α is boxed.

FIG. 12b show the phylogenetic tree of yeast and mouse Sir2 core domains. The core domain sequences of three mouse homologs termed α, γ, and γ are compared on Clustal X and NJPLOT programs to generate the phylogenetic tree.

FIG. 12c illustrates the HPLC chromatogram of the product of deacetylation assay with 10 μg of recombinant mSir2α protein at 1 mM NAD. The calculated efficiency of the reaction is indicated.

FIGS. 14a, 14b and 14c depict the putative ADP-ribosylation activities of Sir2 protein core domain mutants.

FIG. 14a is the amino acid sequence of the core domains of ySir2p (SEQ ID NO: 11), mSir2α (SEQ ID NO: 12) and CobB (SEQ ID NO: 13) aligned and six highly conserved residues, indicated by arrowheads, were mutated to alanine.

FIG. 14b shows the 6×His tagged versions of wildtype ySir2p (wt) and the six mutant Sir2p (Thr-261, Gly-270, Iso-271, Arg-275, Asn-345, Asp-347) and a vector control (vector) expressed in E. coli, purified over a Nickel-NTA column and analyzed on a 7% polyacrylamide SDS gel to assess expression levels.

FIG. 14c depicts the ability of ySir2p and mutant Sir2p proteins to modify histone H3 with $^{32}$P labeled NAD.

FIG. 16a is a Western blot of 25 μg of whole cell extract from wildtype, sir2Δ and Sir2 mutants probed with Sir2 antibody. The upper band corresponds to Sir2p and a lower background band is included as a loading control.

FIG. 16b illustrates silencing at HMLα by mating the strains with tester strains of the opposite mating type and monitoring growth of diploids on selective media.

FIG. 16c illustrates telomere-silencing by the ability of strains with telomeric URA3 to grow on media containing 5-FOA, which is toxic when URA3 is expressed, but harmless when URA3 is silenced.

FIG. 16d illustrates rDNA silencing was monitored in a strain with the ADE2 marker located within the rDNA array. RPD3 was disrupted to enhance silencing differences between the wildtype and sir2Δ strains. sir2 mutant strains were spotted on complete and -ade media to monitor effects on silencing.

FIG. 17a illustrates W303R with ADE2 at rDNA tested for rDNA recombination rates by counting the frequency of loss of the marker in the first generation after plating.

FIG. 17b illustrates the life span of wildtype, sir2Δ, and mutants 261, 270, and 275 measured in hmlAE strains where the a/α effects are eliminated.

FIG. 17c illustrates the life span of wildtype, sir2Δ, and mutants 261 and 270 measured in HML+ strains as a sensitive test of a/α silencing.

FIG. 18 is a summary of in vitro and in vivo data regarding ADP-ribosyltransferase, deacetylase, HM silencing, telomere silencing, rDNA silencing, rDNA recombination and mean life span for Sir2 wildtype and mutant Sir2 proteins (Thr-261, Gly-270, Iso-271, Arg-275, Asn-345, Asp-347).

FIG. 19 depicts the amino acid sequence alignment of the core domain of ySir2 (SEQ ID NO: 14), yHST1 (SEQ ID NO: 15), yHST2 GenBank Accession NO: U39063, (SEQ ID NO: 16), yHST3 GenBank Accession No: U39062, (SEQ ID NO: 17), yHST4 GenBank Accession No: NC_001136 (SEQ ID NO: 18), mSir2alpha (mSir2α, SEQ ID NO: 19), mSir2beta (mSir2β, SEQ ID NO: 20), mSirg (mSir2γ, SEQ ID NO: 21), and deduced amino acid sequences of Sir2-like core domains (GenBank Accession No: AI465098, SEQ ID NO: 22; GenBank Accession No: AI465820, SEQ ID NO: 23; GenBank Accession No: AI466061, SEQ ID NO: 24).

FIGS. 21a, 21b, 21c, and 21d depict the nucleotide sequence (GenBank Accession No: AF214646, SEQ ID NO: 25) and amino acid sequence (SEQ ID NO: 26) of murine Sir2α.

FIG. 22 depicts the nucleotide sequence (SEQ ID NO: 34) and amino acid sequence (SEQ ID NO: 35) of an EST CDNA clone 557657 (Genome Systems, Inc.).

DETAILED DESCRIPTION OF THE INVENTION

Figure 1A:
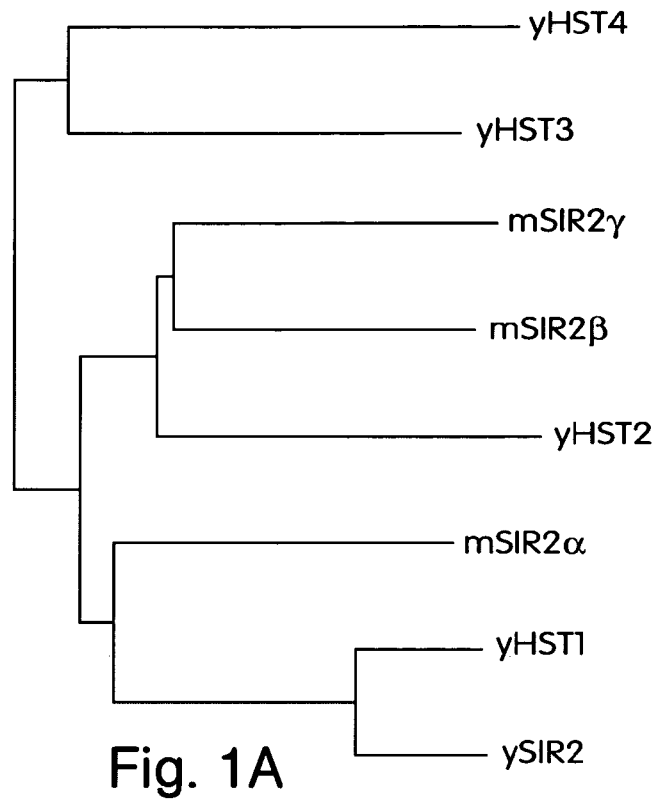
FIG. 1A is a diagrammatic representation of the phylogenetic tree of yeast and murine Sir2 protein core domains.

The invention relates to the discovery that Sir2 proteins, which play a part in the life span control mechanisms in eukaryotic cells, alter the NAD-dependent acetylation status of histone proteins and mono-ADP-ribosylate nuclear proteins. In particular, the invention pertains to the discovery that Sir2 (e.g., murine Sir2α) alters the NAD-dependent acetylation status (e.g., removes and/or adds an acetyl group) of histone proteins (e.g., histone proteins H2B, H2A, H3 and/or H4) and mono-ADP-ribosylates histone proteins. As a result of this discovery, methods for identifying agents (e.g., agonists) which alter the NAD-dependent acetylation status of nuclear proteins, such as histone proteins, and/or their mono-ADP-ribosylation are available to provide methods and compositions to alter (e.g., slow) aging and alter (e.g., increase) life span of cells and organisms.

The present invention relates to a method of altering the NAD-dependent acetylation status of at least one amino acid residue of a histone protein by altering the activity of a Sir2-protein or Sir-2 like protein. In a particular embodiment, the NAD-dependent acetylation status of H3 and/or H4 is altered. Specifically encompassed by the invention is the alteration of lysine residues in the N-terminus of H3 (e.g., lysine 9 and/or 14) and H4 (e.g., lysine 16).

"NAD-dependent" as used herein refers to a requirement for NAD (nicotinamide adenine dinucleotide) compound in a reaction. The reaction can performed or take place in the presence (e.g., in vivo) or the absence (e.g., in vitro) of cells. A "NAD-like compound" is also within the scope of the invention and refers to a compound (e.g., a synthetic or naturally occurring chemical, drug, protein, peptide, small organic molecule) which possesses structural similarity (e.g., adenine, ribose and phosphate groups) or functional similarity (e.g., oxidation of substrates, NAD-dependent deacetylation of histone proteins). For example, NAD-like compounds can be NADH, NADP, NADPH, non-hydrolyzable NAD and fluorescent analogs of NAD (e.g., 1, N6-etheno NAD).

The term "NAD-dependent acetylation status" refers to the requirement of NAD to either transfer (also referred to herein as the addition) or remove (also referred to herein as deacetylation) at least one acetyl group (e.g., $CH_3CO$—) to a substrate having OH or $NH_2$ groups (e.g., at least one amino acid residue of a histone protein such as H2B, H2A, H3 and/or H4). Thus, "acetylation status" can be either acetylation or deacetylation of a substrate.

In a particular embodiment, the amino acid residue who acetylation status is altered is a basic amino acid (e.g., lysine, arginine, histidine). In a preferred embodiment, the acetylation status lysine residues of histone proteins H1, H2A, H2B, H3 or H4 are altered. In a more preferred embodiment, the acetylation status of lysine residues at the amino terminus of H3 and H4 is altered In particular, lysine 9 and/or lysine 14 of H3 and/or lysine 16 of H4. Any suitable amino acid residue (e.g. having OH or $NH_2$ groups) capable of undergoing an alteration in acetylation status in a cell and/or an animal or under in vitro conditions (e.g., outside a cell or an animal) is within the scope of the invention.

The invention also relates to a method of identifying an agent which alters the activity of a Sir2 protein or a Sir2-like protein by assessing the NAD-dependent acetylation status of at least one amino acid in a histone protein, comprising combining the histone protein, the Sir2 protein or the Sir2-like protein, NAD or a NAD-like compound and the agent to be tested, thereby producing a combination; detecting the NAD-dependent acetylation status of an amino acid in the histone protein; and comparing the NAD-dependent acetylation status in the presence of the agent to be tested with the NAD-dependent acetylation status of the amino acid in the histone protein in the absence of the agent to be tested, wherein a difference in the NAD-dependent acetylation status of the amino acid of the histone protein between the presence of the agent and the absence of the agent indicates that the agent alters the NAD-dependent acetylation status of at least one amino acid of the histone protein.

The agent identified by the methods of the invention can add an acetyl group or remove an acetyl group from at least one amino acid residue (e.g., lysine) of a histone protein (e.g., H2B, H3 or H4).

The invention further relates to a method of identifying an agent which alters life span of a cell by altering the activity of a Sir2 protein or a Sir2-like protein by assessing the NAD-dependent acetylation status of at least one amino acid (e.g., lysine) in a histone protein (e.g., H2B, H3 or H4). The histone protein, a Sir2 protein or Sir2-like protein, NAD or a NAD-like compound and the agent to be tested are combined to produce a combination, the NAD-dependent acetylation status of an amino acid in the histone protein is detected (e.g., electron-spray or matrix assisted laser desorption/ionization (MALDI) mass spectroscopy); and compared the NAD-dependent acetylation status in the presence of the agent to be tested with the acetylation status of the amino acid in the histone protein in the absence of the agent to be tested. A difference in the acetylation status of the amino acid of the histone protein between the presence and absence of the agent alters the life span of the cell. The agent tested can increase the lifespan of a cell by NAD-dependent deacetylation of the histone protein. Alternatively, or additionally, the agent can decrease the lifespan of the cell by NAD-dependent acetylation of histone proteins. The agent can be an agonist of Sir2 activity or the agent can be an antagonist of Sir2 activity.

The invention also provides a method of identifying an agent which alters aging of a cell by altering the activity of Sir2 or a Sir-2 like protein by assessing the NAD-dependent acetylation status of at least one amino acid (e.g., lysine) in a histone protein (e.g., H2B, H3 or H4). The histone protein, a Sir2 protein or Sir2-like protein, NAD or a NAD-like compound and the agent to be tested are combined to produce a combination, the NAD-dependent acetylation status of an amino acid in the histone protein is detected (e.g., electronspray mass spectroscopy); and compared the NAD-dependent acetylation status in the presence of the agent to be tested with the acetylation status of the amino acid in the histone protein in the absence of the agent to be tested. A difference in the acetylation status of the amino acid of the histone protein in the presence of the agent alters aging of the cell. The agent tested can increase the aging of a cell by NAD-dependent acetylation of the histone protein. Alternatively, the agent can decrease aging of the cell by NAD-dependent deacetylation of histone proteins. The agent can be an agonist of Sir2 or an antagonist of Sir2.

Agents identified by the in vitro methods of the invention, such as the method described above, can be further evaluated for their ability to alter the NAD-dependent acetylation status in a cell by administering the identified agents to a cell and monitoring the NAD-dependent acetylation status of at least one amino acid in a histone protein of the cell. It is expected that agents identified in vitro as agents which alter the NAD-dependent acetylation status of a histone protein will alter the NAD-dependent alteration status of histone protein in vivo. Likewise, it is expected that the agents which alter NAD-dependent acetylation status of histone proteins by the methods described herein will alter the lifespan and aging of a cell and/or organism.

The invention also relates to a method of altering the NAD-dependent acetylation status of at least one amino acid residue in a histone protein comprising combining the histone protein, a Sir2 protein or Sir2-like protein and a NAD or a NAD-like compound. The method can be used in vitro (e.g., the absence of cells or an animal) or in vivo (e.g., in cells or animals).

The present invention also relates to a method of identifying agents which alter mono-ADP-ribosylation of one or more nuclear proteins in a cell. The cell and agent to be tested are combined and the level of mono-ADP-ribosylation of a nuclear protein, such as one or more histone proteins (e.g., H2B, H2A, H3, H4), is determined and compared to the level of mono-ADP-ribosylation of that protein or proteins in the absence of the agent. A difference in the level of mono-ADP-ribosylation in the presence and absence of the agent indicates that the agent alters the mono-ADP-ribosylation of the nuclear protein. That is, if the level of mono-ADP-ribosylation is greater in the presence of the agent than in the absence of the agent, the agent is an agonist of mono-ADP-ribosylase activity. Similarly, if the level of mono-ADP-ribosylation is greater in the absence of the agent than in the presence of the agent, the agent is an antagonist of mono-ADP-ribosylation.

Alternatively, the method of identifying agents which alter NAD-dependent acetylation status of a histone protein and/or mono-ADP-ribosylation of one or more nuclear proteins can be carried out at the organism (e.g. animal) level. An agent to be tested is administered to an organism, and the alteration in NAD-dependent acetylation of a histone protein and/or the level of mono-ADP-ribosylation of one or more nuclear proteins, such as one or more histone proteins, in cells of the organism is determined and compared to the acetylation status of a histone protein and/or the level of mono-ADP-ribosylation of that protein or proteins in the absence of the agent. A difference in the acetylation status of a histone protein and/or the level of mono-ADP-ribosylation in the presence and absence of the agent indicates that the agent alters NAD-dependent acetylation status of histone proteins and/or the mono-ADP-ribosylation of the nuclear protein.

Agents to be tested for activity in the assays described herein can include proteins (including post-translationally modified proteins), peptides (including chemically or enzymatically modified peptides), or small molecules (including carbohydrates, steroids, lipids, anions or cations, drugs, small organic molecules, oligonucleotides, antibodies, and genes encoding proteins of the agents or antisense molecules), including libraries of compounds. The agents can be naturally occurring (e.g., found in nature or isolated from nature) or can be non-naturally occurring (e.g., synthetic, chemically synthesized or man-made). Agents which alter the level of NAD-dependent acetylation status of histone proteins or the mono-ADP-ribosylation of nuclear proteins of the invention can be agonists (e.g., stimulators/enhancers) or antagonists (e.g., inhibitors) of NAD-dependent acetylation or mono-ADP-ribosylase activity. In a particular embodiment, the agents are agonists or antagonists of Sir2 (e.g., mSir2α, ySir2) dependent NAD-dependent acetylation and mono-ADP-ribosylation of histone proteins (e.g., H2A, H2B, H3, H4).

The term "agonist" as used herein, refers to an agent which simulates or mimics NAD-dependent acetylation or deacetylation of histone proteins (e.g., mSir2, ySir2, human Sir2), a mono-ADP-ribosylase (e.g., mSir2α, ySir2, human Sir2) by, for example, deacetylating H3 or H4 (e.g., removal an acetyl group from at least one lysine residue in the amino terminus) and/or catalyzing the transfer of an adenosine diphosphate ribose unit from an ADP donor (e.g., NAD) to an amino acid residue (e.g., lysine) of a substrate (e.g., histone protein H2B, H3, H4). Alternatively, or additionally, an agonist can be an agent which stimulates, augments, enhances, increases, intensifies or strengthens NAD-dependent acetylation/deacetylation and/or mono-ADP-ribosylase activity or the interaction between a nuclear protein and a NAD-dependent acetylase, mono-ADP-ribosyltransferase, or alters a mono-ADP-ribosylase in a manner (e.g., results in a conformational change) which augments the activity of the mono-ADP-ribosylase such that the nuclear protein is mono-ADP-ribosylated at a higher rate or in greater quantities than in the absence of the agonist. An agonist can also enhance the rate of removal of acetyl groups from amino acid residues of histone proteins.

An agonist can also enhance the availability or accessability of a mono-ADP-ribosylase to a substrate, or a substrate to a mono-ADP-ribosylase, thereby further increasing the level of mono-ADP-ribosylation of a nuclear protein. For example, a substance possessing agonist activity can increase the rate at which ADP-ribose is transferred to an amino acid residue of a histone protein, such as H2B, H2A, H3, or H4 beyond that observed in the absence of the agonist.

The term "antagonist", as used herein, includes a substance which blocks, diminishes, inhibits, hinders, limits, decreases, reduces, restricts or interferes with the NAD-dependent acetylation/deacetylation of histone proteins and/or enzymatic activity of a mono-ADP-ribosylase, alters the substrate (e.g., a histone protein such as H2B, H2A, H3 or H4). An antagonist can act in a manner which prevents Sir2 from deacetylating an amino acid residue in a histone protein and/or a mono-ADP-ribosylase (e.g., mSir2α, ySir2, human Sir2) from acting on the substrate, or interferes with the accessibility of the substrate (e.g., H2B, H2 or H4) to Sir2 for alterations in NAD-dependent acetylation status and/or the mono-ADP-ribosyltransferase, or any combination thereof.

Alternatively or additionally, an antagonist can prevent, impede or interfere with the interaction between Sir2 and NAD, a mono-ADP-ribosyltransferase and a nuclear protein substrate by altering the Sir2 or mono-ADP ribosyltransferase (e.g., conformationally), thereby preventing the Sir2 and/or a mono-ADP-ribosyltransferase from altering the NAD-dependent acetylation status of a histone protein and/or catalyzing the transfer of an adenosine diphosphate ribose unit from an ADP donor (e.g., NAD) to an amino acid residue (e.g., threonine) of a substrate (e.g., a nuclear protein such as a histone protein). For example, a substance possessing antagonist activity can decrease the rate at which the status of NAD-dependent acetylation (e.g., deacetylation) takes place.

An agonist can also prevent, impede or interfere with ADP-ribose transfer to an amino acid residue of a histone protein, such as H2B, H2A, H3 or H4, relative to that observed in the absence of the antagonist.

The agonist or antagonists of the present invention can also alter transcription of NAD-dependent acetylases and/or mono-ADP-ribosyltransferase genes (e.g., SIR2), the mRNA stability of NAD-dependent acetylases and/or mono-ADP-ribosyltransferase transcripts, or degradation of the enzyme as a means to alter NAD-dependent acetylase and/or mono-ADP-ribosyltransferase activity. For example, an agonist can increase the level (e.g., total cellular pool) of deacetylated histone proteins by increasing the activity of Sir2 in an NAD-dependent manner. Likewise agonists of the invention can also mono-ADP-ribosylated nuclear protein by increasing transcription of mono-ADP-ribosyltransferase enzyme genes (e.g., SIR2α) or decreasing enzyme degradation in a cell.

Similarly, an antagonist can decrease the levels of deacetylated histone proteins or increase the amount of acetylated histone proteins. Antagonists can also decrease the levels of mono-ADP-ribosylation of a nuclear protein by down regulating transcription of mono-ADP-ribosyltransferase genes or increasing degradation of the enzyme.

As used herein, a "cell" refers to a single cell or a collection of at least two or more cells. The cell can be a yeast cell (e.g., Saccharomyces cerevisiae) or a mammalian cell, including but not limited to, somatic or embryonic cells, Chinese hamster ovary cells, HeLa cells, human 293 cells and monkey COS-7 cells. The collection of cells can form a tissue or an organism. An "organism" refers to any living individual, such as a vertebrate animal (e.g., a mammal, including but not limited to, mice, rats, pigs dogs, cats, primates, and humans) or nonvertebrate animal, such as an insect (e.g., Drospholia melanogaster) or nematode (e.g., C. elegans), considered as a whole. A "tissue" refers to a collection of similar cell types (such as epithelium, connective, muscle and nerve tissue).

The term "mono-ADP-ribosylation", as used herein, refers to the transfer of one adenosine diphosphate ribose unit from an ADP donor (e.g., NAD) to an amino acid residue (e.g., threonine) of a substrate (e.g., one or more histone proteins such as H2B). A "mono-ADP-ribosyltransferase" (also referred to herein as mono-ADP ribosylase is a protein (also referred to herein as a polypeptide) which catalyzes the mono-ADP-ribosylation. For example, mono-ADP-ribosyltransferases encompassed by the invention include murine (m) SIR2 genes and proteins (e.g., mSir2α, mSir2β, mSir2γ), human Sir2 genes (Frye, *Biochem. Biophys. Res. Commun.* 260:273-279 (1999)) and proteins, yeast genes and proteins that are Homologous to SIR2 (HST) (e.g., HST1, HST2, HST3, HST4), and nucleic acid molecules having accession numbers AI466061, AI465820, or AI465098. (See FIG. 19). Database accession numbers for the nucleotide and amino acid sequences for some of these mono-ADP-ribosyltransferases are known. (Frye, *Biochem. Biophys. Res. Commun.* 260:273-279 (1999)). A mSIR2β EST CDNA clone (SEQ ID NO: 34, 35) 557657 can be purchased from Genome Systems, Inc.

Other known mono-ADP-ribosyltransferases include bacterial toxins, such as cholera, pertussis and diphtheria toxins and mammalian glycosylphosphatidylinositol (GP1)-anchored mono-ADP-ribosyltransferases (Domenighini, et al., *Microbiology* 21:667-674 (1996); Moss, et al., *Mol. Cell.* *Biochem.* 193:109-113 (1999)). It is understood that any protein that mono-ADP-ribosylates nuclear proteins, in particular histone proteins such as H2B, H2A, or H3, is within the scope of the invention.

A "level of mono-ADP-ribosylation" refers to an amount of a substrate to which an adenosine diphosphate ribose has been transferred. The level of mono-ADP-ribosylation can be assessed using methods known in the art, such as in vitro labeling techniques, for example, by monitoring the addition of [$^{32}$P]NAD+ to a substrate (e.g., H2A, H2B, H3). By way of illustration only, the ADP-ribosylase activity of an agent and the level of mono-ADP-ribosylation of a substrate can be determined by adding a protein to be evaluated (about 0-1 g) to a reaction buffer comprising 50 mM Tris-HCl, pH 8.0, 4 mM $MgCl_2$, 0.2 mM DTT, 1 µM cold or nonradiolabeled NAD, 0.08 µM [$^{32}$P]NAD and admixing or gently vortexing to dilute, resuspend or mix the protein. Substrates (e.g., histone proteins at a concentration of about 0-1 g) are then added and the reaction mixture is incubated at ambient temperature (18-25° C.) for 30-120 minutes. The presence or absence of ADP-ribosylation products (e.g., ADP-ribosylated nuclear proteins) is detected using autoradiography. Differences in the levels of mono-ADP-ribosylation, for example in the presence and absence of an agent to be tested, can be determined using suitable techniques, including, but not limited to, densitometric scanning of autoradiographs or phosphoimaging techniques of gels. (See, Ausubel, et al., "Current Protocols in Molecular Biology" John Wiley & Sons (1999)). Techniques to perform the mono-ADP-ribosylation assays are detailed in the Exemplification Section.

Confirmation of mono-ADP-ribosylation of substrates and, thus, mono-ADP-ribosyltransferase activity of an agent, can be performed, for example, by adding a suitable amount of snake venom phosphodiesterase (e.g., 2 mg/ml, specific activity 1.5 U/mg) to the resulting product of the reaction mixture described above. The reaction product and phosphodiesterase are incubated at about 37° C. for about an hour. Absence of an autoradiographic band following phosphodiesterase digestion, as compared with presence of an autoradiographic band in the absence of digestion, indicates that the substrate was mono-ADP-ribosylated (FIG. 4E). Mono-ADP-ribosylase activity can also be verified by the addition of one or more specific mono-ADP-ribosylation inhibitors, including, but not limited to, novobiocin and coumermycin A1, to in vitro assays described above (FIG. 4F). The inhibitor (s) can be added before or after the addition of the substrate. The absence of a band in an autoradiograph following the addition of a specific mono-ADP-ribosylation inhibitor indicates that the agent has mono-ADP-ribosylase activity. Thus, the mono-ADP-ribosyltransferase activity of agents is evaluated by mono-ADP-ribosylation of substrate proteins as described in the Exemplification Section.

In a preferred embodiment, agonists of the invention are agonists of Sir2 NAD-dependent acetylation of histone proteins and Sir2 mono-ADP-ribosyltransferase activity. The identification of agonists or antagonists of Sir2 activity can be initially evaluated using yeast cells. In the presence of an agonist of Sir2 activity, a yeast cell will produce a red colonies, whereas antagonists of Sir2 will result in a white colony. When the ADE2 gene is inserted into one of the three Sir2-regulated silencing loci (e.g., telomere rDNA, or HM mating loci) it is silenced in the presence of the agonists, which eventually leads to yeast cells accumulating red pigment. When the ADE2 gene is transcribed in the presence of antagonists, yeast cells metabolizing the intermediate red pigments and become white in color. Prescreening agents employing color selection of yeast cells will be particularly useful for large scale screening of agents which alter the activity of NAD-acetylation of histone proteins and mono-ADP-ribosyltransferases that ADP-ribosylate nuclear proteins. Following a color selection screening protocol agents can be further evaluated for their ability to alter NAD-dependent acetylation of histone proteins and the level of mono-ADP-ribosylation of nuclear proteins using techniques described herein.

The mono-ADP-ribosyltransferases described herein catalyze the addition of ADP-ribose to cellular proteins, specifically nuclear proteins. A "nuclear protein" refers to any protein, polypeptide or peptide that is located in or performs a function in the nucleus of a eukaryotic cell (e.g., a yeast cell, a zebrafish cell, a C. elegans cell, Drosophila melanogaster cell, or a mammalian cell, such as a murine cell or a human cell). In a preferred embodiment, the nuclear proteins are histone proteins. Histone proteins are highly conserved DNA-binding nuclear proteins that form the nucleosome, the basic subunit of the chromatin. Histone proteins can be one or more core histone proteins (e.g., H2A, H2B, H3, H4) or an outer histone protein (e.g., H1), or combinations thereof. In a more preferred embodiment, the substrate for mono-ADP-ribosylation is histone H2B or H3.

The term "alters" is defined as a change in an activity (e.g., NAD-dependent acetylation status of at least one amino acid of a histone protein, mono-ADP-ribosylation) or phenomena (e.g., aging, life span), for example, relative to an activity or phenomena in the absence of an agent to be tested. Alteration includes both an increase and a decrease (e.g., complete abolishment), either qualitatively, quantitatively or both, in the activity or phenomena being monitored.

The agent to be tested (e.g., an agonist or antagonist) can be combined with the cell before or after the addition of the substrate (e.g., a histone protein such as H2B, H3, and/or H4). Experimental conditions for evaluating test substances, such as buffer (e.g., 50 mM Tris-HCl, pH 8.0) or media, concentration (about 0-1 g), temperature (about 18-25° C.), and incubation (about 30-120 minutes) requirements, can, initially, be similar to those described in the Exemplification Section herein relating to NAD-dependent acetylation status of histone proteins and mono-ADP-ribosylation of histone proteins by mSir2α or ySir2. One of ordinary skill in the art can determine empirically how to vary experimental conditions depending upon the biochemical nature of the agent and the particular cell used in the methods described herein.

If the agent to be tested is being administered to an organism, various methods and routes of administration are known in the art. The agent will preferably be formulated in a pharmaceutical composition. For instance, suitable agents can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The effective amount and optimum concentration of the active ingredient(s) (e.g., the agent) in the chosen medium can be determined empirically, according to procedures well known to medicinal chemists, and will depend on the ultimate pharmaceutical formulation desired. Methods of administration of compositions for use in the invention include, but are not limited to, intradermal, intramuscular, intraperitoneal, intravenous, subcutaneous, intraocular, oral and intranasal. Other suitable methods of introduction can also include rechargeable or biodegradable devices and slow release polymeric devices. The pharmaceutical compositions of this invention can also be administered as part of a combinatorial therapy with other agents.

The invention further relates to the discovery that increased NAD-dependent deacetylation of histone protein by Sir2 and/or mono-ADP-ribosylation of one or more nuclear proteins (e.g., histone proteins) correlates with decreased rDNA recombination, increased life span and decreased aging at the cellular level. Thus, agents which increase NAD-dependent deacetylation of histone proteins by Sir2 and/or mono-ADP-ribosylation of nuclear proteins are expected to be agents which decrease rDNA recombination, increase life span and decrease aging. Accordingly, in another embodiment, the methods of the invention relate to identifying agents which alter the life span of a cell or an organism. It is envisioned that the methods of the invention can be used for any cell that undergoes aging, for example, a mammalian cell (e.g., from a human), a zebrafish cell, a C. elegans cell, or Drosophila melanogaster cell in, for example, experimental systems.

The cell or organism is combined with the agent to be tested and the level of NAD-dependent acetylation or deacetylation of histone proteins by Sir2 and/or mono-ADP-ribosylation of one or more nuclear proteins is determined in the presence of the agent and compared to the level in an appropriate control in the absence of the agent. A difference in the level NAD-dependent acetylation of histone proteins and/or of mono-ADP-ribosylation of the nuclear protein in the presence of the agent indicates that the agent alters NAD-dependent acetylation of histone proteins and/or the mono-ADP-ribosylation of a nuclear protein of a cell or an organism and that the agent alters life span of the cell or organism.

Figure 20:
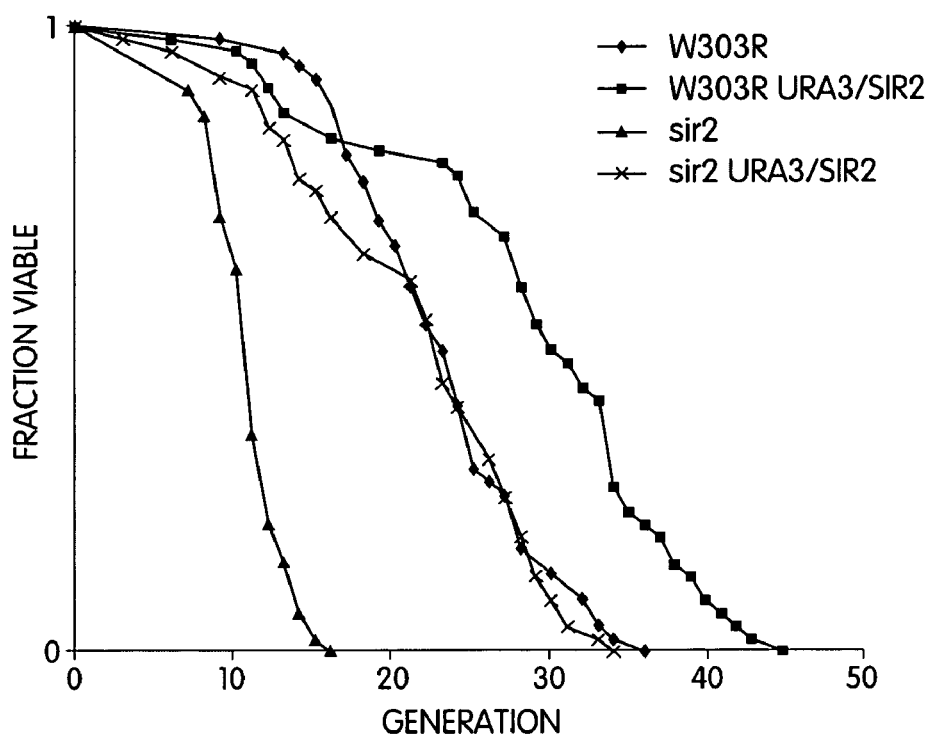
FIG. 20 depicts the effects of multiple copies of Sir2 on yeast life span.

Methods of determining life span of a cell or an organism are known in the art. With regard to a yeast cell, for example, "life span" refers to the number of generations, or divisions of a mother cell, which give rise to daughter cells. Techniques to assess the life span of yeast cells, including growth conditions for particular strains, are well known and include stress-resistance methods, cell surface labeling methods and temperature sensitive methods. (See, for example, Guarente et al., U.S. Pat. No. 5,874,210 (1999), the teachings of which are incorporated herein in their entirety). The life span of a yeast cell in the presence of an agent can be initially identified, e.g., by the mean number of generations using a colony color selection strategy. The ability of an agent to alter (e.g., increase) the life span of a cell, as described herein, is measured as an increase in the mean life span of a cell(s) as compared with the mean life span of a cell(s) not combined with the test agent. For example, the life span of the yeast *Saccharomyces cerevisiae* can be increased at least 2-3 fold in the presence of two copies of the yeast or mammalian (e.g., murine, human) NAD-dependent deacetylase and/or mono-ADP-ribosyltransferase SIR2 gene compared to cells lacking the SIR2 gene (FIG. 20). When SIR2 is deleted from yeast haploid cells the life span of cells is reduced by about 50% compared to wild type. When an extra copy of the SIR2 gene is introduced into wild type yeast haploid cells (the yeast cells have two copies of the gene), the cells display a longer life span than wild type (Kennedy, et al., *Cell* 90:485-496, (1995); Kaeberlein, et al., *Genes & Development*, 13:2370-2580, (1999)).

The life span of mammalian cells (e.g., human and murine diploid fibroblasts, epithelial cells and lymphocytes) refers to the number of population doublings until the cells are in a growth-arrested state such as "cellular senescence" (Hayflick et al., *Experimental Cell Research*, 25:585-621, (1961); Todaro, et al., *Journal of Cell Biology*, 17: 299-313, (1963); Rohme, *Proc. Natl. Acad. Sci. USA*, 78:5009-5013, (1981)). For some mammalian cells which obtain the ability to proliferate indefinitely in culture (e.g., cell lines established from cancers and cell lines engineered chemically or genetically to have infinite life span), the life span can be artificially terminated by the methods of the invention. In this case, the life span is defined as the average doubling cycles before the cells die by the induction of cellular senescence or apoptosis.

The life span of an organism (e.g., vertebrate organism, such as a human, or a nonvertebrate organism, such as an insect, nematode or fish) refers to the average (also referred to herein as mean) duration of life of a given organism. For example, the average life span of a male human being is about 71.8 years, and the average life span of a female human being is about 78.6 years and the average life span of a mouse is about 0.7-2.7 years (Finch, "Longevity, Senescence and the Genoma," Univ. of Chicago Press, Chicago, Ill. (1990)).

In one embodiment, the agent increases the life span of the cell or organism by increasing the NAD-dependent deacetylation of histone proteins, in particular at least one amino acid at the N-terminal lysine residues of H3 (e.g., lysine 9 and/or lysine 14) and/or H4 (e.g., lysine 16), by increasing the activity of Sir2. In another embodiment, the agent increases the lifespan of the cell or organism by increasing the level of mono-ADP-ribosylation of a nuclear protein, such as H2B or H3, in particular mono-ADP-ribosylation of a lysine residues in H3 and/or H4. An increase in life span would be a duration of a particular life beyond the average for that cell or organism.

In another embodiment, the agent decreases the life span of the cell or organism by decreasing the activity of Sir2, thereby altering NAD-dependent acetylation (e.g., deacetylation) of histone proteins, in particular at least one amino acid at the N-terminus of H3 (e.g., lysine 9 and/or lysine 14) and/or H4 (e.g., lysine 16). In an additional embodiment, the agent decreases the level of mono-ADP-ribosylation of a nuclear protein, such as H2B or H3. A decrease in life span would a duration of a particular life less than average for that cell organism.

The invention also pertains to a method of identifying an agent which alters aging of a cell or an organism. The cell or organism and agent to be tested are combined and the level of NAD-dependent acetylation of histone proteins and/or the level of mono-ADP-ribosylation of a nuclear protein (e.g., H2B, H2A or H3) is determined and compared to the NAD-dependent acetylation status of a histone protein and/or the level of mono-ADP-ribosylation of the nuclear protein in the absence of the agent. A difference in the NAD-dependent acetylation status and/or level of mono-ADP-ribosylation in the presence and absence of an agent indicates that the agent alters aging of the cell or organism.

"Aging" refers to all time-dependent changes to which biological entities, from molecules to ecosystems, are subject, though the mechanisms and consequences to function may be vastly different (Medawar, "An Unsolved Problem of Biology", H. K. Lewis, London, (1952). Additionally or alternatively, aging refers to the process of growing old or senencing. Aging is associated with particular phenotypes in a cell or organism. In a cell, aging can be characterized by an increase in cell size, a slowing of the cell cycle, shortening of telomeres, and/or expression of some particular categories of genes (Stanulis-Praeger, *Mech. Ageing Dev.* 38:1-48, (1987); Faraher, et al., *BioEssay,* 20:985-991, (1998)). The changes in heterochromatin structure and mitochondria can also be associated with aging (Imai, et al., *Experimental Gerontology,* 33:555-570, (1998); Wallace, et al., *Biofactors,* 7:187-190, (1998)). In yeast cells, sterility, the appearance of surface wrinkles, blebs and bud scars, nucleolar enlargement and fragmentation, and formation, replication, and accumulation of rDNA circles are also associated with aging (Sinclair, Mills and Guarente, *Annu. Rev. Microbiol.,* 52533-560, (1998)).

In yeast, aging is defined by the relatively fixed number of cell divisions undergone by mother cells (Müller et al., *Aging Dev.* 12:47 (1980)), as well as characteristic changes during their life span (Jazwinski, *Science* 273:54 (1996)), such as cell enlargement (Mortimer and Johnson, *Nature* 183:1751 (1959)) and sterility (Müller, *J. Microbiol. Serol.* 51:1 (1985)). Techniques to determine aging in a yeast cell are well-known and are described, for example, in Guarente et al., U.S. Pat. No. 5,874,210 (1999), Smeal, et al., *Cell* 84:633-642 (1996); Sinclair, et al., *Science* 277:1313-1316 (1997); Sinclair, et al., *Cell* 91:1033-1042 (1997)), the teachings of all of which are incorporated herein in their entirety.

Aging of an organism refers to the deterioration of the organism associated with changes in structures and functions (e.g., phenotype) that are characteristic of a particular organism. Such characteristics can include, for example, hair loss, graying of hair, osteoporosis, cataracts, atherosclerosis, loss of skin elasticity and a propensity for certain cancers.

The agents identified by the methods of the present invention can be used to alter the aging of a cell or an organism by altering the level Sir2 activity, NAD-dependent acetylation status of histone proteins and/or of mono-ADP-ribosylation of a nuclear protein. In a preferred embodiment, the agents identified by the methods of the invention decrease aging of the cell or organism. In another embodiment, the agents identified by the methods of the invention increase aging of the cell or organism.

Due to their ease of experimental manipulation, similar structural features associated with aging in mammalian cells (Guarente et al., U.S. Pat. No. 5,874,210 (1999)), and an Sir2 protein which shares sequence (nucleic acid and amino acid) and enzymatic (e.g., NAD-dependent acetylation of histone proteins, mono-ADP-ribosyltransferase) with a mammalian Sir2 proteins (e.g., mSir2α, mSir2β), the yeast cell is a suitable cellular model to identify agents which alter NAD-dependent acetylation of histone proteins or mono-ADP-ribosylation of nuclear proteins, increase life span and decrease aging in mammalian cells and organisms as well as nonmammalian cells and organisms (e.g., insect, nematode, fish). Moreover, a mammalian (e.g., mSir2α) NAD-dependent deacetylase and/or mono-ADP-ribosylase increases the life span and slows aging of yeast cells. Thus, mammalian and yeast Sir2 proteins mediate similar biological activities.

As defined herein, mammals include rodents (such as rats, mice or guinea pigs), domesticated animals (such as dogs or cats), ruminant animals (such as horses, cows) and primates (such as monkeys or humans).

Thus, the agents identified by the methods described herein, which increase life span or decrease aging as described above, can be used to increase the life span or decrease aging of cells, e.g., mammalian cells including human cells, or vertebrate (e.g., mice, humans, guinea pigs, rats) or invertebrate (e.g., insects, nematodes) organisms. For example, cells to be treated can be combined with an effective amount of an agent that increases the activity of Sir2, increases the NAD-dependent deacetylation of histone proteins, and/or level of mono-ADP-ribosylation of a nuclear protein, thereby increasing their life span or decreasing their aging relative to untreated cells or organisms.

An "effective amount" of an agent, as used herein, is defined as that quantity of an agent which increases life span or decreases aging, to any degree, in the cell or organism being treated by increasing, to any degree, the NAD-dependent deacetylation of histone proteins by Sir2 or a Sir2-like protein and/or the level of mono-ADP-ribosylation of a nuclear protein (e.g., H2B, H2A, H3, or H4). In a preferred embodiment, lysines at position 9 and/or 14 in H3 are deacetylated and/or lysine at position 16 in H4 is deacetylated. For example, an effective amount of an agonist of a mono-ADP-ribosyltransferase in a cell can inhibit certain characteristics associated with aging, for example, the formation of rDNA with, or without, inhibiting other characteristics, such as the replication and/or accumulation of rDNA. Similarly, an effective amount of an agent that increases the NAD-dependent deacetylation of histone proteins (e.g., H2B, H3 and/or H4) and/or the levels of mono-ADP-ribosylation of a nuclear protein can decrease aging in an organism by slowing hair loss, with or without, diminishing graying or hair, cataracts or atherosclerosis.

It is envisioned that the agents identified by the methods of the present invention can be administered to cells or organisms which age naturally (e.g., normally) or age prematurely or abnormally (e.g., as a result of Werner's syndrome in mice or humans) due to genetic permutations. Thus, the agents identified by the methods of the present invention, can be useful in anti-aging therapies and for the treatment of aging diseases, such as Werner's syndrome, to prevent, halt, hasten, slow or ameliorate premature aging. Additionally, or alternatively, the identification of agents which alter the NAD-dependent acetylation status of histone proteins (e.g., lysines 9 and/or 14 of H3, lysine 16 of H4) and/or the mono-ADP-ribosylation of nuclear proteins can be also useful for the continued study of cellular and organismal aging processes.

Thus, the present invention also pertains to methods of increasing the life span or decreasing the aging of a cell or an organism by administering an effective amount of an agent that increases the NAD-dependent deacetylation of histone proteins and/or increases the mono-ADP-ribosylation of a nuclear protein. The agent is identified by combining an agent to be tested with a cell or an organism and determining the level of NAD-dependent deacetylation of histone proteins (e.g., H3, H4) and/or mono-ADP-ribosylation of a nuclear protein in the presence of the agent which is compared to the NAD-dependent acetylation of a histone protein and/or level of mono-ADP-ribosylation of a nuclear protein in the absence of the agent. The presence of an agent which increases life span or decreases aging increases the activity of Sir2 thereby increasing the deacetylation of histone proteins and/or increases the level mono-ADP-ribosylated nuclear protein (e.g., H2B, H2A, H3, H4).

The present invention also pertains to methods of increasing the life span or decreasing aging of a cell or an organism by administering to the cell or organism an agonist of Sir2 that increases the NAD-dependent deacetylation of histone proteins, a mono-ADP-ribosyltransferase (e.g., Sir2) or an agonist of a mono-ADP-ribosyltransferase of a nuclear protein. In a preferred embodiment, the nuclear protein is a histone protein, in particular H2A, H2B, H3 or H4. In a more preferred embodiment, the acetylation status if lysine residues at positions 9 and/or 14 of H3 are altered and the lysine at position 16 of H4 is altered by altering the activity of Sir2. Preferably the mono-ADP-ribosyltransferase is a Sir2 protein (e.g., Sir2α, Sir2β, Sir2γ). Specifically, the core domain of a Sir2 protein (FIGS. 2B, 6A, 14a, 19; SEQ ID NOS: 2, 3, 4, 5, 9, 10, 11, 12, 13, 14, 15, 16, 17, 18, 19, 20, 21, 22, 23 and 24) alters the NAD-dependent acetylation status of histone proteins, the mono-ADP-ribosyltransferase or the agonist of NAD-dependent acetylation status of histone proteins and/or mono-ADP-ribosyltransferase activity of the core domain of Sir2.

Because aging in cells is associated with the formation, replication and/or accumulation of ribosomal DNA (rDNA) circles, the present invention relates to methods of inhibiting the formation, replication and/or accumulation of rDNA circles in a cell or an organism by administering an effective amount of a mono-ADP-ribosyltransferase or agonist of NAD-dependent acetylation status of histone proteins and/or a mono-ADP-ribosyltransferase to a cell or organism. rDNA circles accumulate exponentially in old yeast mother cells and are responsible for age-related enlargement and fragmentation of the nucleolus, and appear to nucleate the fragmented nucleolus. (Sinclair, et al., Cell 91:1033-1042 (1997)). For example, agents which have been identified by methods described herein as agonists of NAD-dependent deacetylation and/or of mono-ADP-ribosylation of nuclear proteins can be administered to a cell or an organism to suppress the formation, replication and/or accumulation of rDNA circles. The cell samples thus treated are then examined for longer-lived, slower aged colonies, using any of the methods described herein or other appropriate methods.

The invention further relates to a method of suppressing recombination between rDNA in a cell or an organism comprising administering to the cell or the organism a mono-ADP-ribosyltransferase or an agonist of NAD-dependent deacetylation of histone proteins and/or a mono-ADP-ribosyltransferase. Recombination between rDNA is a characteristic of aging in cells. In yeast cells, sterility associated aging is due to a loss of transcriptional silencing at HMRa and HMLα loci, and the resulting expression of both a and α mating-type information (Smeal et al., Cell 84:633 (1996)). The Sir2 protein silences genes inserted at rDNA (Bryk et al., Genes Dev. 11:255 (1997); Smith and Boeke, Genes Dev. 11:241 (1997)) and suppresses recombination between rDNA repeats (Gottleib and Esposito, Cell 56:771 (1989)). Thus, suppressing recombination between rDNA by administering a mono-ADP-ribosyltransferase or an agonist of a NAD-dependent deacetylation of histone proteins and/or mono-ADP-ribosyltransferase can also decrease aging and increase life span.

Agents which alter the NAD-dependent acetylation status of histone proteins and/or mono-ADP-ribosylation of nuclear proteins (e.g., agonist of NAD-dependent deacetylation and/or mono-ADP-ribosyltransferase activity) can be formulated into compositions. Such compositions can also comprise a pharmaceutically acceptable carrier, and are referred to herein as pharmaceutical compositions. The agonist or antagonist compositions of the present invention can be administered intravenously, parenterally, orally, nasally, by inhalation, by implant, by injection, or by suppository. The agonist or antagonist compositions can be administered in a single dose or in more than one dose over a period of time to achieve a level of NAD-dependent deacetylation of histone proteins and/or mono-ADP-ribosylation of nuclear protein which is sufficient to confer the desired effect.

Suitable pharmaceutical carriers include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The pharmaceutical preparations can be sterilized and if desired, mixed with auxiliary substances, e.g., lubricants, preservatives, stabilizers, wetting substances, emulsiers, salts for influencing osmotic pressure, buffers, coloring, and/or aromatic substances and the like which do not deleteriously react with the agonist or antagonist compounds. They can also be combined where desired with other active substances, e.g., enzyme inhibitors, to reduce metabolic degradation.

For parenteral application, particularly suitable are injectable, sterile solutions, preferably oily or aqueous solutions, as well as suspensions, emulsions, or implants, including suppositories. Ampules are convenient unit dosages.

It will be appreciated that the actual effective amounts of an agonist or antagonist of NAD-dependent acetylation status of histone proteins and/or mono-ADP-ribosylation of nuclear proteins in a specific case can vary according to the specific agonist or antagonist being utilized, the particular composition formulated, the mode of administration and the age, weight and condition of the patient, for example. For example, an effective amount of an agonist is an amount of agonist capable of slowing aging or extending the life span of a cell or an organism by altering the NAD-dependent acetylation status and/or mono-ADP-ribosylating substrates such as nuclear proteins (e.g., histone proteins, preferably H2A, H2B, H3). Dosages of suitable agonists or antagonists of NAD-dependent deacetylation of histone proteins and/or mono-ADP-ribosylation of nuclear proteins for a particular patient can be determined by one of ordinary skill in the art using conventional considerations, (e.g. by means of an appropriate, conventional pharmacological protocol).

The present invention further relates to novel murine SIR2 (Silent Information Regulator) genes (e.g., mSIR2α, mSIR2β) and their protein products. The invention also relates to the discovery that mSir2α and yeast Sir2 (ySir2) proteins possess mono-ADP-ribosyltransferase activity, in particular mSir2α and ySir2 mono-ADP-ribosylate histone proteins (e.g., H2B, H3, H4). As shown in the Exemplification Section, transfection of yeast cells, which lack SIR2, with ySIR2 genes, slows aging and extends the life span of cell. Specifically, the administration of two copies of the ySIR2 gene increases life expectancy of the cell about 1.5 fold over cells with a single copy of the SIR2 gene and about 2-3 fold above cells which do not contain the SIR2 gene. Thus, the SIR2 gene of the present invention plays a critical role in the life span and aging of a cell and, thus, of a multicellular organism such as a mammal.

The terms "SIR2" and "Sir2 amino acid sequence or Sir2 protein" refer to the SIR2 gene and its protein product, respectively. SIR2 or Sir2 refers to the any of the yeast (e.g., *S. cerevisiae*) SIR2 or Sir 2. "mSIR2" or "mSir2" refers to any murine SIR2 (e.g., SIR2α, SIR2β, SIR2γ). The terms "SIR2 nucleic acid", "nucleotide sequence of SIR2" or the "corresponding SIR2 nucleic acid", refer to the nucleic acid sequence that encodes the Sir2 protein.

The present invention also relates to the nucleic acid sequences encoding murine Sir2 proteins (e.g., mSir2α, mSir2β, mSir2γ). In particular a full length cDNA and genomic DNA nucleic acid sequence of mSIR2α and a partial cDNA sequence of SIR2β. The murine Sir2 proteins (e.g., mSir2α, mSir2β, mSir2γ) are encoded by at least three different genes. The nucleic acid sequence (SEQ ID NO.: 25) that encodes mSir2α protein (SEQ ID NO.: 26) can be found in FIG. 21.

The Sir2 proteins have functional domains. For example, one domain can be the core domain and another domain can be the amino-terminus or carboxy-terminus. The core-domain of the Sir2 protein (e.g., mSir2α) can alter the NAD-dependent acetylation status of histone proteins and/or mono-ADP-ribosyltransferase activity. The invention is also intended to embody the functional domains (e.g., core-domain of Sir2), as described herein. The amino acid sequence of the core domain of the mSir2α protein (SEQ ID NOS.: 4, 9, 12 and 19) is depicted in FIGS. 2C, 6, 14a and 19. Amino acid sequences (SEQ ID NOS: 2, 3, 5, 10, 11, 13, 14, 15, 16, 17, 18, 20, 21, 22, 23 and 24) which share structural identity to the nucleic acid and amino acid sequences of mSir2α are depicted in FIGS. 2C, 6A, 14a and 19.

The term "isolated", as it refers to a Sir2 protein, means a protein, as found in nature, but separated away from other proteins and cellular material of their source of origin. The isolated Sir2 proteins include essentially pure protein from cells, proteins produced by chemical synthesis, by combinations of biological and chemical synthesis and/or by recombinant methods.

The invention is intended to encompass Sir2 proteins, and proteins and polypeptides having amino acid sequences analogous (also referred to herein as similar or homologous) to the amino acid sequences of the Sir2 protein (e.g., mSir2α, ySir2) and functional equivalents or fragments thereof. Such proteins are defined herein as Sir2-like proteins, Sir2 homologs (e.g., analogues) or derivatives. Any protein possessing the Sir2 consensus sequence GAGISTS(L/A)GIPDFR (SEQ ID NO: 27) or YTQNID (SEQ ID NO: 28) (Brachmann, et al., *Genes & Development* 9:2888-2902 (1995) and which is capable of NAD-dependent deacetylation and/or mono-ADP-ribosylation of nuclear proteins is within the scope of the invention.

It is also envisioned that other Sir proteins (e.g., Sir1, Sir3, Sir4) or Sir-like proteins and the nucleic acids (e.g., SIR1, SIR3, SIR4) which encode Sir proteins, other than Sir2 or Sir2-like proteins, are within the scope of the invention.

Analogous or homologous amino acid sequences are further defined herein to mean amino acid sequences with sufficient identity to the Sir2 amino acid sequences so as to possess the biological activity of a Sir2 protein (e.g., mono-ADP-ribosylation of histone proteins). For example, an analogous peptide can be produced with "silent" changes in amino acid sequence wherein one, or more, amino acid residues differ from the amino acid residues of the Sir2 protein, yet still possess the biological activity of Sir2. Examples of such differences include additions, deletions or substitutions of residues of the amino acid sequence of Sir2. Also encompassed by the invention are analogous proteins that exhibit greater, or lesser, NAD-dependent deacetylation of histone proteins and/or mono-ADP-ribosyltransferase activity (e.g., biological activity) of the Sir2 protein of the present invention. Such structurally and functionally related proteins are also referred to herein as "Sir2-like" proteins.

The "biological activity" of a Sir2 protein is defined herein to mean the ability to alter the NAD-dependent acetylation status of a histone protein and/or the mono-ADP-ribosylates a substrate such as a histone protein (e.g., H2B, H2A, H3, H4). In particular, the biological activity of mSir2α is the ability to alter the NAD-dependent acetylation status of lysine residues in the N-terminus of H3 (e.g., lysine 9 and/or 14) and/or H4 (e.g., lysine 16) and/or mono-ADP-ribosylate an amino acid residue of H2B, H3 or H4. Additionally, or alternatively, the biological activity also means the ability to slow aging or extend life span by, for example, repressing recombination of rDNA, or inhibiting the formation, replication and/or accumulation of rDNA circles of a cell or an organism. The biological function of Sir2 is illustrated and further defined by the Exemplification Section.

The invention also encompasses biologically active polypeptide fragments of the Sir2 protein, as described herein. Such fragments can include only a part of a full length amino acid sequence of Sir2 and yet possess the ability to NAD-dependent deacetylation and/or mono-ADP-ribosylate a substrate. Specifically encompassed by the invention are fragments of Sir2 comprising the core domain of Sir2.

The term "core domain" (also referred to herein as "core") refers to the evolutionarily conserved domains of Sir2 or Sir2-like proteins which can be identified, for example, by the comparison of amino acid sequences by, for example, CLUSTAL X, BLAST, PSI-BLAST or FASTA algorithms. The "core domain" is the domain that shows significant identity and/or homology to about 240-270 amino acids of Sir2 or Sir2-like proteins (about 20-50% or higher as amino acid identity, see FIG. 2) and/or possesses the consensus sequence GAG(V/I)S(T/V)S (L/C/A)GIPDFRS (SEQ ID NO:38) and YTQNID (SEQ ID NO: 28) (Brachmann, et al., *Genes & Development* 9:2888-2902, (1995)). The "core domain" of Sir2 proteins has NAD-dependent deacetylation and/or mono-ADP-ribosylation activities. Any protein with a "core domain" of a Sir2 protein, a fragment of the core domain, or any functional or structural equivalent which is capable of NAD-dependent deacetylation and/or mono-ADP-ribosylation of nuclear proteins is within the scope of the invention.

Figure 2D:
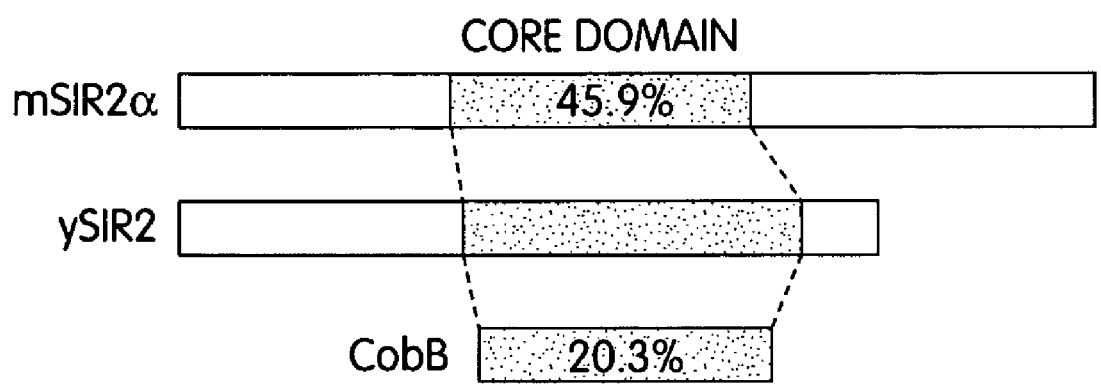
FIG. 2D is a schematic alignment of the core domain of mSir2α, ySir2p and CobB proteins.

The Sir2 protein and nucleic acid sequence include homologues, as defined herein. The homologous proteins and nucleic acid sequences can be determined using methods known to those of skill in the art. Initial homology searches can be performed at NCBI against the GenBank (release 87.0), EMBL (release 39.0), and SwissProt (release 30.0) databases using the BLAST and PSI-BLAST network services. (See, for example, Altshul, et al., *J. Mol. Biol.* 215: 403 (1990); Altschul et al. *Nucleic Acid Res.* 25: 3389-3402 (1997); Altschul, *Nucleic Acids Res.* 25:3389-3402 (1998), the teachings of which are incorporated herein by reference). Computer analysis of nucleotide sequences can be performed using the MOTIFS and the FindPatterns subroutines of the Genetics Computing Group (GCG, version 8.0) software. Protein and/or nucleotide comparisons can also be performed according to CLUSTAL algorithms (Higgins, et al., *Gene,* 73: 237-244 (1988)). Homologous proteins and/or nucleic acid sequences to the Sir2 protein and/or nucleic acid sequences that encode the Sir2 protein are defined as those molecules with greater than 25% sequences identity, also referred to herein as similarity, (e.g., 30%, 40%, 50%, 60%, 70%, 80% or 90% homology). The percent identity between the yeast (*S. cerevisiae*) SIR2 sequence and the murine SIR2α and SIR2β sequence is 45.9% (FIG. 2D). These particular sequence similarities and identities were determined using the CLUSTAL algorithm.

Homology was determined in accordance with the methods described in above (e.g., BLAST, PSI-BLAST algorithms). Homologs of mSIR2α can be, for example, mSIRγ, mSIR2β, ySIR2, yHST1, yHST2, yHST3, yHST4 (amino acid sequences depicted in SEQ ID NOS: 2, 3, 5, 10, 11, 13, 14, 15, 16, 17, 18, 20, 21, 22, 23 and 24; FIG. 2C, 6A, 14a and 19) and human SIR2 nucleic acid or protein (Frye, *Biochem. Biophys. Res. Commun.* 260:273-279 (1999)).

Sequence identity of homologs of SIR2 can be to the entire nucleic acid or amino acid sequence, or to the core domain of the protein. In one embodiment, the BLAST or PSI-BLAST parameters are set such that they yield a sequence having at least about 60% sequence identity with the corresponding known mSIR2α sequence, preferably, at least about 70% sequence. In another embodiment, the percent sequence identity is at least about 85%, and in yet another embodiment, at least about 95%. Such molecules are also referred to herein as Sir2-like proteins. Thus, the Sir2-like proteins possess structural identity with the SIR2 molecules (e.g., nucleic acid or amino acid identity) described herein. The Sir2-like proteins are capable of altering the NAD-dependent acetylation status of at least one amino acid in a histone protein (e.g. lysine 9 and/or 14 of H3, lysine 16 of H4) and/or mono-ADP-ribosylating substrates (e.g., histone proteins), thus extending the life span or slowing the aging of a cell or an organism.

Biologically active derivatives or analogs of the Sir2 protein can be made using peptide mimetics, designed and produced by techniques known to those of skill in the art. (see e.g., U.S. Pat. Nos. 4,612,132; 5,643,873 and 5,654,276, the teachings of which are incorporated herein by reference). These peptide mimetics can be based, for example, on a specific Sir2 amino acid sequence such as the core domain of Sir2α. These peptide mimetics can possess biological activity similar to the biological activity of the corresponding peptide compound, but possess a "biological advantage" over the corresponding Sir2 amino acid sequence with respect to one, or more, of the following properties: solubility, stability and susceptibility to hydrolysis and proteolysis.

It is also envisioned that any NAD-dependent deacetylase that alters the acetylation status of at least one, amino acid of a histone protein and/or a mono-ADP-ribosyltransferase or Sir2-like protein containing proteins functionally equivalent to the Sir2 proteins described herein will be within the scope of the invention. The phrase "functionally equivalent" as used herein refers to any molecule (e.g., peptide, peptide mimetic, protein and nucleic acid sequence encoding the protein) which mimics the NAD-dependent deacetylation activity of Sir2 and/or mono-ADP-ribosyltransferase activity of the Sir2α proteins and/or functional domains of Sir2 (e.g., the carboxy-terminus) described herein (such as Sir2β, Sir2γ, HST1, HST2, HST3) or which exhibit nucleotide or amino acid sequence identity to Sir2α such as Sir2β, Sir2γ, for example.

The Sir2 protein or Sir2-like protein can also be mutated to down-regulate or affect one or more properties of the protein, while other properties still exist. In particular, the Sir2 protein can be mutated at a position in the sequence that prevents it from catalyzing the transfer of an ADP ribose from a donor, such as NAD, to a substrate and/or from acetylating or deacetylating at least one amino acid of a histone protein (e.g., lysine 9 and/or 14 of H3, lysine 16 of H4).

Thus, another embodiment of the present invention encompasses mutants of Sir2 proteins with altered NAD-dependent deacetylation activity and/or mono-ADP-ribosyltransferase activity. Mutants with NAD-dependent deacetylation activity and/or mono-ADP-ribosyltransferase activity greater than that of wildtype (e.g., nonmutant, naturally occurring) Sir2 are referred to as having "increased" NAD-dependent deacetylation activity or "increased" mono-ADP-ribosyltransferase activity. Mutants with a mono-ADP-ribosyltransferase activity less than that of wildtype Sir2 are referred to as having "decreased" NAD-dependent deacetylation activity or "decreased" mono-ADP-ribosyltransferase activity. The mutants of the present invention can be used, for example, to further understand the mechanism of substrate specificity and cellular pathways influenced by NAD-dependent deacetylation of histone proteins and/or mono-ADP-ribosylation of substrates, such as histone proteins.

The term "mutant", as used herein, refers to any modified nucleic acid sequence encoding a Sir2 protein or Sir2-like protein. For example, the mutant can be a protein produced as a result of a point mutation or the addition, deletion, insertion and/or substitution of one or more nucleotides encoding the Sir2 protein, or any combination thereof. Modifications can be, for example, conserved or non-conserved, natural or unnatural.

As used herein a mutant also refers to the protein encoded by the mutated SIR2 nucleic acid. That is, the term "mutant" also refers to a protein (also referred to herein as polypeptide) which is modified at one, or more, amino acid residues from the wildtype (e.g., naturally occurring) Sir2 protein. In a preferred embodiment, mutants are generated by mutations in mSir2α or ySir2 proteins. In a particular embodiment, the core domain of the mSir2α protein, as described herein, has a mutation resulting in a altered mono-ADP-ribosyltransferase activity. For example, in this embodiment the mSir2α mutant is a mutant of mSir2α resulting from a point mutation substituting the glycine at position 253 in the core domain of mSir2α with alanine residue to generate the G253A Sir2α mutant. Sir2 mutants can be made by mutations to one, or more, amino acid residues selected from a group consisting of glycine, serine, proline, isoleucine, phenylalanine, threonine, or histidine, or any combination thereof.

As used herein the designation for the amino acid substitutions for the Sir2 mutants is indicated as, for example, "G253A", wherein the letter to the left of the number indicates the amino acid in the wildtype Sir2 protein (e.g., "G" or glycine); the number indicates the position of the amino acid in the wildtype Sir2 protein (e.g., position 253); and the letter to the right of the number indicates the amino acid residue which replaces the wildtype (e.g., "A" or alanine).

Additionally, or alternatively, the mutants are designated by the amino acid which is mutated to an alanine residue, for example Thr-261, Gly-270, Iso-271, Arg-275 or Asn-345. Specifically encompassed by the invention are mSir2α mutants G253A, G255A, S257A, I262A, F265A, R266A, G270A (also referred to herein as Gly-270), P285A, T336A, H355A; and ySir2 mutants Thr-261, Iso-271, Arg-275, Asn-345 and Asp-347.

Using well-known techniques to align amino acids, amino acid residues suitable for mutation as described herein for mSir2α or ySir2 proteins can be determined for other Sir2 (e.g., Sir2β, Sir2γ) or Sir2-like (e.g., HST1, HST2) proteins. Nucleic acid sequences encoding the Sir2 proteins can be mutated; the mutated nucleic acid constructs expressed under standard experimental conditions well known to the skilled artisan; and the resulting mutant proteins evaluated for NAD-dependent deacetylation of histone proteins and/or mono-ADP-ribosyltransferase activity, the ability to slow aging, or extend life span as described herein.

It is also envisioned that fragments of the Sir2 proteins can be used in the methods of the invention. "Fragments" of Sir2 proteins, as used herein, refer to any part of the Sir2 protein capable of altering the NAD-dependent acetylation status of at least one amino acid residue of a histone protein (e.g., lysine 9 and/or 14 of H3, lysine 16 of H4) and/or mono-ADP-ribosylating a substrate (e.g., H2B, H3, or H4). For example, the core domain of the Sir2 protein is considered a fragment of Sir2.

A Sir2 protein can be in the form of a conjugate or a fusion protein which can be manufactured by known methods. Fusion proteins can be manufactured according to known methods of recombinant DNA technology. For example, fusion proteins can be expressed from a nucleic acid molecule comprising sequences which code for a biologically active portion of the Sir2 protein and a fusion partner, for example, a portion of an immunoglobulin or a peptide linker. A nucleic acid construct encoding a Sir2 fusion protein can be introduced into a host cell, expressed, isolated or purified from a cell by means of an affinity matrix employing antibodies to Sir2 or the fusion partner (e.g., IgG).

Antibodies can be raised to the Sir2 protein, Sir2-like protein, analogs, and portions thereof, using techniques known to those of skill in the art. (See, for example, Kohler et al., Nature 256:495-497 (1975); Cole et al., "Monoclonal Antibodies and Cancer Therapy", Alan R. Liss, Inc., pp. 77-96 (1985); Ausubel et al., "Current Protocols in Molecular Biology", John Wiley & Sons, Inc. (1999)). A mammal, such as a murine, rat, hamster or rabbit, can be immunized with an immunogenic form of the protein (e.g., mSir2α, mSirβ, or a peptide comprising an antigenic fragment of the protein which is capable of eliciting an antibody response). Techniques for conferring immunogenicity on a protein or peptide include conjugation to carriers, such as BSA or keyhole limpet hemocyanin, or other techniques, such as the use of Freud's adjuvant or Titermax, well known in the art. The progress of immunization can be monitored by detection of antibody titers in plasma or serum. Standard ELISA, RIA or Western blots can be used with the Sir2 protein to assess the levels of antibody.

In a preferred embodiment, the antibody, or antigen-binding fragment, selectively binds murine Sir2 proteins, such as mSir2α and mSir2β. An "antigen-binding fragment" of an antibody refers to an antibody which binds to any part of the Sir2 protein.

The antibodies of the invention can be human and nonhuman antibodies. The antibodies can be polyclonal, monoclonal, chimeric (e.g., human chimeric antibodies), or fragments thereof. These antibodies can be used to purify or identify the Sir2 protein contained in a mixture of proteins, using techniques well known to those of skill in the art. These antibodies, or antigen-binding fragments thereof, can be used to detect the presence or absence of the Sir2 protein using standard immunochemistry, Western blot methods, ELISA, or RIA. For example, and ELISA and RIA assays can be used to quantitate the amount of Sir2 in a cellular or nuclear extract.

As used herein, an "isolated" nucleic acid molecule (e.g., gene, nucleotide sequence, nucleic acid sequence), when referring to an Sir2 protein encoded by a nucleic acid sequence, is a nucleic acid molecule which is not flanked by nucleic acid molecules which normally (e.g., naturally occurring) flank the gene or nucleotide sequence (e.g., as in genomic sequences) and/or has been completely or partially purified from other transcribed sequences (e.g., as in a cDNA library). Thus, an isolated nucleic acid molecule, gene or nucleotide sequence can include a nucleic acid molecule, gene or nucleotide sequence which is synthesized chemically or by recombinant means. Nucleic acid molecules contained in a vector are included in the definition of "isolated" as used herein. Also, isolated nucleic acid molecules include recombinant nucleic acid molecules and heterologous host cells, as well as partially or substantially or purified nucleic acid molecules in solution. In vivo and in vitro RNA transcripts of the invention are also encompassed by "isolated" nucleic acid molecules. Such isolated nucleic acid molecules are useful for introduction into host cells, the manufacture of the encoded Sir2 protein, as probes for isolating homologues sequences (e.g., from other mammalian species or other organisms), for gene mapping (e.g., by in situ hybridization), or for detecting the presence (e.g., by Southern blot analysis) or expression (e.g., by Northern blot analysis, RNase protection assays) of related SIR2 genes in cells or tissue.

The present invention also encompasses isolated nucleic acid sequences encoding the Sir2 proteins described herein, and fragments of nucleic acid sequences encoding biologically active Sir2 proteins. Fragments of the nucleic acid sequences, described herein, as useful as probes to detect the presence of SIR2. Specifically provided for in the present invention are DNA/RNA (also referred to herein as nucleic acid) sequences encoding mSir2α and mSir2β proteins, the fully complementary strands of these sequences, and allelic variations thereof. Also encompassed by the present invention are nucleic acid sequences, genomic DNA, cDNA, RNA or a combination thereof, which are substantially complementary to the nucleic acid sequences (e.g., DNA, RNA) encoding Sir2 (e.g., mSir2α, mSir2β), and which specifically hybridize with the SIR2 nucleic acid sequences under conditions of stringency known to those of skill in the art, those conditions being sufficient to identify nucleic acid sequences with substantial nucleic acid identity. As defined herein, substantially complementary means that the sequence need not reflect the exact sequence of the SIR2 nucleic acid, but must be sufficiently similar in identity of sequence to hybridize with SIR2 nucleic acid under stringent conditions. Conditions of stringency are described, for example, in Ausubel, et al., "Current Protocols in Molecular Biology", John Wiley & Sons, Inc. (1999). Non-complementary bases can be interspersed in the sequence, or the sequences can be longer or shorter than SIR2 nucleic acid, provided that the sequence has a sufficient number of bases complementary to SIR2 to hybridize therewith.

The SIR2 nucleic sequence, or a fragment thereof, can be used as a probe to isolate additional SIR2 homologs. For example, a cDNA or genomic DNA library from the appropriate organism can be screened with labeled SIR2 nucleic acid probes (e.g., DNA or RNA) to identify homologous genes, as described, for example, in Ausubel, F. M., et al., "Current Protocols in Molecular Biology", John Wiley & Sons, (1999).

Typically the nucleic acid probe comprises a nucleic acid sequence of sufficient length and complementary to specifically hybridize to nucleic acid sequences which encode mSir2α (SEQ ID NO: 25), mSir2β, mSir2γ, ySir2 or human Sir2. The requirements of sufficient length and complementarity can be easily determined by one of skill in the art.

Uses of nucleic acids encoding cloned Sir2 proteins or fragments include one or more the following: (1) producing proteins which can be used, for example, for structure determination, to further assess Sir2 NAD-dependent deacetylation activity and/or mono-ADP-ribosyltransferase activity, or to obtain antibodies binding to the Sir2 protein; (2) to determine the nucleotide sequence encoding a Sir2-like protein which can be used, for example, as a basis for comparison with other proteins to determine conserved regions, determine unique nucleotide sequences for normal and altered proteins, and to determine nucleotide sequences to be used as target sites for antisense nucleic acids, ribozymes, hybridization detection probes, or PCR amplification primers; (3) as hybridization detection probes to detect the presence of a native protein and/or a related protein in a sample; and (4) as PCR primers to generate particular nucleic acid sequence regions, for example, to generate regions to be probed by hybridization detection probes.

The Sir2 proteins and/or nucleic acid sequences include fragments thereof, (e.g., core domains of Sir2 proteins). Preferably, the nucleic acid contains at least 14, at least 20, at least 27, and at least 45, contiguous nucleic acids of a sequence provided in SEQ ID NO.: 25. Advantages of longer-length nucleic acid include producing longer-length protein fragments having the sequence of a Sir2 protein which can be used, for example, to produce antibodies; increased nucleic acid probe specificity under high stringent hybridization assay conditions; and more specificity for related the SIR2 nucleic acid under lower stringency hybridization assay conditions.

Another aspect of the present invention features a purified nucleic acid encoding a Sir2 protein or fragment thereof. Specifically, mSIR2α (SEQ ID NO: 25), mSIR2γ and/or mSIR2β. Due to the degeneracy of the genetic code, different combinations of nucleotides can code for the same protein. Thus, numerous protein fragments having the same amino acid sequences can be encoded for by difference nucleic acid sequences. In preferred embodiments, the nucleic acid encodes at least 12, at least 18, or at least 54 contiguous amino acids of SEQ ID NO.: 25.

Another aspect of the present invention features a purified nucleic acid having a nucleic acid sequence region of at least 12 contiguous nucleotides substantially complementary to a sequence region in SEQ ID NO.: 25. By "substantially complementary" is meant that the purified nucleic acid can hybridize to the complementary sequence region in nucleic acid sequences of SEQ ID NO.: 25, under stringent hybridizing conditions. Such nucleic acid sequences are particularly useful as hybridization conditions, only highly complementary nucleic acid sequences hybridize. Preferably, such conditions prevent hybridization of nucleic acids having 4 mismatches out of 20 contiguous nucleotides, more preferably 2 mismatches out of 20 contiguous nucleotides, most preferably one mismatch out of 20 contiguous nucleotides. In preferred embodiments, the nucleic acid is substantially complementary to at least 20, at least 27, or at least 45 contiguous nucleotides provided in SEQ ID NO.: 25.

Another aspect of the present invention features a purified protein having at least about 5-20 contiguous amino acids of an amino acid sequence provided in SEQ ID NOS.: 1, 2, 3, 4, 5, 9, 10, 11, 12, 13, 14, 15, 16, 17, 18, 19, 20, 21, 22, 23, 24, 26, 27 or 28. By "purified" in reference to a protein is meant that the protein is in a form (e.g., its association with other molecules) distinct from naturally occurring protein. Preferably, the protein is provided as substantially purified preparation representing at least 75%, more preferably 85%, most preferably 95% or the total protein in the preparation. In preferred embodiments, the purified protein has at least 5 contiguous amino acids of SEQ ID NO.: 27 or 28.

Preferred protein fragments include those having functional Sir2 activity (e.g., alter the NAD-dependent acetylation status of histone proteins such as H3 or H4; mono-ADP-ribosylate nuclear proteins such as H2B, H3 or H4), or epitope for antibody recognition. Such protein fragments have various uses such as being used to obtain antibodies to a particular region and being used to form chimeric proteins with fragments of other proteins create a new protein having unique properties, such as a longer half-life.

Nucleic acid molecules can be inserted into a construct which can, optionally, replicate and/or integrate into a recombinant host cell, by known methods. The host cell can be a eukaryote or prokaryote and includes, for example, yeast (such as *Pichia pastorius* or *Saccharomyces cerevisiae*) bacteria (such as *Escherichia coli* or *Bacillus subtilis*), animal cells or tissue, insect Sf9 cells (such as baculoviruses infected SF9 cells) or a mammalian cells (somatic or embryonic cells, Chinese hamster ovary cells, HeLa cells, human 293 cells, monkey COS-7 cells and mouse NIH 3T3 cells).

The invention also provides vectors or plasmids containing one or more of each of the SIR2 genes. Suitable vectors for use in eukaryotic and prokaryotic cells are known in the art and are commercially available or readily prepared by a skilled artisan. Additional vectors can also be found, for example, in Ausubel, F. M., et al., "Current Protocols in Molecular Biology", John Wiley & Sons, Inc. (1999) and Sambrook et al., "Molecular Cloning: A Laboratory Manual," 2nd Ed. (1989), the teachings of which are incorporated herein by reference in their entirety.

Another aspect of the present invention features a recombinant host cell comprising an isolated nucleic acid molecule of a SIR2 gene operably linked to a regulatory sequence. "Operably linked" is intended to mean that the nucleotide sequence(s) is linked to a regulatory sequence in a manner which allows expression of the nucleic acid sequence(s). The recombinant host cell is made up of an isolated nucleic acid sequence encoding at least about 5-20 contiguous amino acids provided in SEQ ID NO.: 1, 2, 3, 4, 5, 9, 10, 11, 12, 13, 14, 15, 16, 17, 18, 19, 20, 21, 22, 23, 24, 26, 27 or 28 and a cell able to express the nucleic acid. Cells containing a functioning Sir2 protein can be used, for example, to screen to agonists or antagonists of Sir2 activity.

The nucleic acid molecule can be incorporated or inserted into the host cell by known methods. Examples of suitable methods of transfecting or transforming cells include calcium phosphate precipitation, electroporation, microinjection, infection, lipofection and direct uptake. "Transformation" or "transfection" as used herein refers to the acquisition of new or altered genetic features by incorporation of additional nucleic acids, e.g., DNA. "Expression" of the genetic information of a host cell is a term of art which refers to the directed transcription of DNA to generate RNA which is translated into a protein. Methods for preparing such recombinant host cells and incorporating nucleic acids are described in more detail in Sambrook et al., "Molecular —Cloning: A Laboratory Manual," 2nd Ed. (1989) and Ausubel, et al. "Current Protocols in Molecular Biology," (1999), for example.

The host cell is then maintained under suitable conditions for expression of Sir2. Generally, the cells are maintained in a suitable buffer and/or growth medium or nutrient source for growth of the cells and expression of the gene product(s). The growth media are not critical to the invention, are generally known in the art and include sources of carbon, nitrogen and sulfur. Examples include Luria broth, Superbroth, Dulbecco's Modified Eagles Media (DMEM), RPMI-1640, M199 and Grace's insect media. The growth Media may contain a buffer, the selection of which is not critical to the invention. The pH of the buffered Media can be selected and is generally one tolerated by or optimal for growth for the host cell.

The mSIR2α gene can be expressed in mammalian or insect cells, any mammalian or insect expression plasmid or viral vector driven by native mSIR2α promoter can be used, any of other mammalian or insect promoters and enhances, any of viral promoters, or any of artificial inducible promoters can be used. The host cells can be cells of murine, human, or any of other organisms including insects cultured in conventional or specialized in vitro culture conditions. The cells transfected with a mSIR2 expression plasmid or infected by the virus containing a mSIR2α expression vector.

The host cell is maintained under a suitable temperature and atmosphere. Alternatively, the host cell is aerobic and the host cell is maintained under atmospheric conditions or other suitable conditions for growth. The temperature should also be selected so that the host cell tolerates the process and can be, for example, between about 13°-40° C.

The invention also relates to a method of preparing a Sir2 protein using the recombinant host cells described above. The recombinant host cells are biological factories to produce proteins encoded for by the isolated nucleic acid molecule of SIR2.

The chromosomes of higher eukaryotes are compartmentalized into two cytogenetically distinct regions, euchromatin and heterochromatin. Heterochromatin was initially described as chromosomal regions that failed to decondense after mitosis (Heitz, E. *Jb. Wiss. Bot.* 69:728 (1928)) Subsequent studies have revealed that heterochromatin is formed on highly repetitive DNA, such as centromeres and telomeres, replicates late in the cell cycle and is transcriptionally inactive (Hennig, W. *Heterochromatin. Chromosoma* 108:1-9 (1999)). Although many questions about the functional and structural properties of heterochromatin are unresolved, progress in understanding its molecular nature has been made in studies of yeast (Karpen, G., et al., *Trends Genet* 13: 489-496 (1997)); (Grunstein, M. *Cell* 93, 325-328 (1998)) and *Drosophila* (Wakimoto, B. T., *Cell* 93: 321-324 (1998)). In *Drosophila*, genes juxtaposed to centromeric heterochromatin through chromosomal rearrangement or transposition become inactivated. The phenomenon, known as position effect variegation (PEV) (Muller, H. J.; *J. Genet* 22: 299-335 (1930)), results from the spreading of heterochromatin across the rearrangement breakpoint. Genetic screens have identified large numbers of PEV modifiers some of which have been cloned and characterized (Reuter, G., et al., *BioEssays* 14: 605-612 (1992); (Weiler, K. S., et al., *Annu. Rev. Genet.* 29: 577-605 (1995); (Wallrath, L. L., *Curr. Opin. Genet. Dev.* 8: 147-153 (1998)). Heterochromatin protein 1 (HP1) are one of the best-characterized heterochromatin components and known to localize at centromeres and telomeres (James, T. C., et al., *Mol. Cell. Biol.* 6: 3862-3872 (1986); (James, T. C., et al., *Eur. J. Cell Biol.* 50: 170-180 (1989); (Fanti, L., et al., *Mol. Cell* 2: 527-538 (1998)). HP1-related proteins have been identified from a wide variety of organisms including mammals, and a region termed the chromodomain is highly conserved in HP1 family members (Singh, P. B., et al., *Nucleic Acids Res.* 19: 789-794 (1991)). The chromodomain is also shared by a related set of chromatin factors, the Polycomb group (Pc-G) (Pirrotta, V., *Cell* 93: 333-336 (1998)). Pc-G is required to maintain the repressed state of homeotic genes through many cell divisions in the developmental stages of *Drosophila* (Orlando, V., et al., *Cell* 75:1187 (1993)).

Transcriptional silencing in budding yeast is associated with genomic domains of structurally altered chromatin akin to heterochromatin in higher cells (Sherman, J. M., et al., *Trends Genet.* 13: 308-313 (1997)).

The principle genes required for silencing SIR2, SIR3, and SIR4 encode members of a complex that is targeted to the specific chromosomal domains that are silenced (Ivy, J. M., et al., *Mol. Cell. Biol.* 6: 688-702 (1986); (Gotta, M., et al., *J. Cell Biol.* 134: 1349-1363 (1996); (Rine, J., et al., *Genetics* 116: 9-22 (1987); (Aparicio, O. M., et al., *Cell* 66: 1279-1287 (1991)). For example, silencing at the extra copies of α and a mating type genes at HMLα and HMRa is mediated by the binding of these three Sir proteins, plus a fourth, Sir1p, to a set of DNA binding factors including Rap1p, ORC, and Abf1p (Triolo, T., et al., *Nature* 381: 251-253 (1996)).

In contrast, at telomeres Sirs 2p, 3p, and 4p bind to tandem Rap1p molecules arrayed at the telomeric repeat tract (Hardy, C. F. J., et al., *Genes Dev.* 6: 801 (1992); (Moretti, P., et al., *Genes Dev.* 8: 2257 (1994)). Finally, at the rDNA, Sir2p, but not the other Sir proteins, is bound to a specific region in the rDNA spacer in a complex termed RENT which includes another protein, Net1p (Shou, W., et al., *Cell* 97: 233-244 (1999)).

The function of SIR-mediated silencing at HM loci is to prevent the expression of both a and α mating types, which would lead to non-mating, pseudo-diploid strains. The role of the Sir complex at telomeres is less apparent. Interestingly, the telomeric Sir complex, along with the Ku protein, moves to sites of double strand DNA breaks to aid their repair by the non-homologous end joining pathway, suggesting that telomeric Sir complex exists as a poised DNA repairosome (Mills, K. D., et al., *Cell* 97: 609-620 (1999); (Martin, S. G., et al., *Cell* 97: 621-633 (1999)).

Sir2p in the rDNA silences marker genes inserted there (Bryk, M., et al., *Genes Dev.* 11: 255-269 (1997); (Smith, J. S., et al., *Genes Dev.* 11: 241-254 (1997)) and, plays an important role in repressing recombination within the 100-

200 tandemly repeated copies of the rDNA sequences in chromosome XII (Gottlieb, S., et al., *Cell* 56: 771-776 (1989)).

Replicative life span in yeast mother cells (the number of times a mother cell divides to give daughters) is limited, at least in part, by the accumulation of extrachromosomal rDNA circles (ERCs) in nuclei of aging mothers (Sinclair, D. A., et al., *Science* 277: 1313-1316 (1997)). These accumulated ERCs result from the excision of circles from the chromosomal rDNA array by homologous recombination (Park, P. U., et al., *Mol. Cell. Biol.* 19: 3848-3856 (1999)), the subsequent replication of ERCs in future cell divisions, and the preferential segregation of ERCs to mother cells.

SIR2, SIR3, and SIR4 play a key role in determining the life span of yeast mother cells (Kennedy, B. K., et al., *Cell* 89: 381-391 (1997); (Kaeberlein, M., et al., *Genes Dev.* 13: 2570-2580 (1999)). Deleting SIR3 or SIR4 shortens the life span by about 25%, and deleting SIR2 shortens the life span by about 50%. The shortening in the sir3 and sir4 mutants is due to the simultaneous expression of a and α mating type information, which somehow causes an increase in recombination in the rDNA leading most likely to an earlier accumulation of a lethal number of ERCs (Kaeberlein, M., et al., *Genes Dev.* 13: 2570-2580 (1999)).

The shortening in sir2 mutants is due to the absence of Sir2p in the rDNA leading to the elevated rate of recombination at that locus and the rapid generation of ERCs. The short life span of sir2 mutants is suppressed by deletions of FOB1 (Kaeberlein, M., et al., *Genes Dev.* 13: 2570-2580 (1999)), which encodes a protein that creates a unidirectional barrier to DNA replication in the rDNA (Kobayashi, T., et al., *Genes Cells* 1: 465-474 (1996)). Evidently this barrier is a signal that provokes recombination in the rDNA and the generation of ERCs (Defossez, P. A., et al., *Mol. Cell* 3: 447-455 (1999)), and the role of Sir2p is to counteract this hyperrecombination. In the absence of Fob1p (and the replication barrier) Sir2p is no longer needed to prevent the formation of ERCs. The addition of a second copy of SIR2 to cells extends the replicative life span of mothers well beyond that of the wild type, indicating that Sir2p is the limiting factor for life span (Kaeberlein, M., et al., *Genes Dev.* 13: 2570-2580 (1999)).

Since chromatin at HML and HMR is hypoacetylated (Braunstein, M., et al., *Mol. Cell. Biol.* 16: 4349-4356 (1996); (Braunstein, M., et al., *Genes Dev* 7: 592-604 (1993)), Sir2p was hypothesized to be a histone deacetylase. However, it is also possible that hypoacetylation of chromatin results from some other effect, such as the exclusion of acetylases by the inaccessible structure of these chromosomal regions or the recruitment of other deacetylases.

More recent studies identified SIR2 orthologs in yeast and homologs in many species, including bacteria, which all share a core homology of about 270 amino acids. The four *S. cerevisiae* orthologs HST1-4 do not play any role in yeast silencing, with the exception that high level expression of HST1 can partially compensate for the absence of SIR2 (Brachmann, C. B., et al., *Genes Dev.* 9: 2888-2902 (1995)). The bacterial homolog, cobB, can apparently function in cells in a biosynthetic step that transfers phosphoribose from nicotinate mononucleotide to dimethyl benzimidazole (Tsang, A. W., et al., *J. Biol. Chem.* 273: 31788-31794 (1998)). The present invention, documents that yeast Sir2p and its mouse homologue mSir2α are mono-ADP-ribosyltransferases and NAD hydrolases with specifically acetylated histone substrates. Amino acid changes in mSir2α that disrupt this enzymatic activity also reduce function in vivo. The modification of the acetylation status of N-terminal tails of histones by Sir2 can trigger genomic silencing in yeast and heterochromatin formation more generally in eukaryotic organisms.

As described herein, yeast Sir2p and its mouse Sir2α homologue possess ADP-ribosyltransferase and NAD hydrolase. These activities are stimulated by N-terminal peptides of histones H3 and H4. In particular, acetylated lysines of histone proteins Lys9Ac and Lys14Ac of H3 and Lys16 of the H4. Transfer to histone H2B is also observed. Studies using enzyme inhibitors and snake venom phosphodiesterase show that Sir2β and mSir2α are mono-ADP ribosyltransferases.

Sir2 Proteins are Novel Nuclear Mono-ADP-Ribosyltransferases with Histone Substrates Yeast and mouse Sir2 proteins are shown herein to be mono-ADP-ribosyltransferases by several criteria. First, the proteins transfer $^{32}$P-labeled ADP-ribose from NAD to histones H2B and H3. The endogenous mSir2α protein immunoprecipitated from NIH3T3 cell extracts shows the same activity. Second, this modification can be removed by snake venom phosphodiesterase, which digests the phosphodiester bond in the ADP-ribose moiety. Third, the reactions are sensitive to mono-ADP-ribosylation inhibitors, but not to poly (ADP-ribose)polymerase (PARP) inhibitors. ySir2p and mSir2α provide the first examples of nuclear mono-ADP-ribosyltransferases in yeast and mammals.

In the mammalian nucleus, PARPs are likely involved in DNA repair (Menissier-de Murcia, J., et al., *Proc. Natl. Acad. Sci. USA* 94: 7303-7307 (1997); (Wang, Z. Q., et al., *Genes Dev.* 11: 2347-2358 (1997)), replication (Yoshida, S., et al., *Mol. Cell. Biochem.* 138: 39-44 (1994)), transcription (Oliver, F. J., et al., *Embo J.* 18: 4446-4454 (1999)), apoptosis (Germain, M., et al., *J. Biol. Chem.* 274: 28379-28384 (1999)) and telomere maintenance (Di Fagagna, F. D. A., et al., *Nat. Genet.* 23: 76-80 (1999)). On the other hand, it has been reported that alkylating agents induce mono-ADP-ribosylation of histones H1, H2B, and H3 (Kreimeyer, A., et al., *J. Biol. Chem.* 259: 890-896 (1984); (Adamietz, P., et al., *J. Biol. Chem.* 259:6841-6846 (1984)). Interestingly, many viral, bacterial, and eukaryotic enzymes such as diphtheria, pertussis, and cholera toxins (DT, PT, and CT, respectively) and vertebrate arginine-specific mono-ADP-ribosyltransferases catalyze similar reactions (Domenighini, M., et al., *Mol. Microbiol.* 21: 667-674 (1996)).

These ADP-ribosyltransferases share structural motifs in their catalytic domains and can be classified into two groups: the DT group and the CT group (Domenighini, M., et al., *Mol. Microbiol* 21: 667-674 (1996); (Moss, J., et al., *Mol. Cell Biochem.* 193: 109-113 (1999)). The DT group includes diphtheria toxin and the family of PARPs, while the CT group includes CT, PT, and other eukaryotic mono-ADP-ribosyltransferases. ySir2p and mSir2α share at least one motif of the CT group (see FIG. 2C), hydrophobic-Ser-Thr-Ser-hydrophobic (VSTSL, SEQ ID NO: 30, in ySir2p and VSVSC, SEQ ID NO: 31, in mSir2α), which forms the NAD-binding cleft. The mutation of the first serine, which is known to be important for positioning NAD, abolishes the mono-ADP-ribosylation activity of the mSir2α (see FIG. 6C).

The mutagenesis of highly conserved residues in the mSir2α core domain revealed that mutations in 10 of 10 residues affected the mono-ADP-ribosylation activity. In mouse cells, 9 of these 10 mutants were inactive in a transient assay for repression of a reporter, suggesting that the enzymatic activity is critical in vivo. The mutant, P285A, could misfold in *E. coli* and thus be inactive. Genetic analysis of the core of yeast Sir2p indicates that the four conserved cysteines at positions 372, 374, 396, and 398 are crucial for silencing in vivo. Further, chimeras in which a human Sir2 core domain is substituted for the yeast domain can function in silencing at HM loci, but not at telomeres or rDNA.

Specific Acetylation of H3 and H4 Tails Stimulates Sir2 Activities

A striking feature of the specificity of ADP-ribosylation of H3 was revealed by the use of N-terminal peptides (residues 1-20). Sir2 modified the H3 N-terminal tail peptide when Lys9 and Lys14 were acetylated but not when the peptide was unacetylated. These lysines are acetylated and important for silencing in vivo (Thompson, J. S., et al., *Nature* 369: 245-247 (1994)). In addition, a large fraction of the NAD was hydrolyzed specifically in the presence of the diacetylated peptide and either yeast or mouse Sir2. This latter activity can reflect inefficient transfer of ADP-ribose to the peptide substrate or can present another yet unknown activity of Sir2 proteins in the modification of histones. These data show that the N-terminal tail of H3 is a biologically relevant target of Sir2 proteins in vivo.

An H4 peptide (residues 1-20) acetylated on Lys16 stimulated both ADP-ribosyltransferase and NAD hydrolase activities of Sir2, but H4 peptides acetylated on Lys5, Lys8, or Lys 12 did, at best, very weakly. A tetra-acetylated H4 peptide (aceylated Lys5, 8, 12 and 16) was also a poor substrate. Lys16 is a highly acetylated residue in mammalian chromatin. In constitutive heterochromatin, H4 is hypoacetylated at all four lysines, but in facultative heterochromatin Lys5, 8, and 12 are hypoacetylated, while Lys16 is not. Thus, these data illustrate the role of Sir2 in regulating the state of facultative heterochromatin, consistent with the observed intracellular localization of the protein. In yeast mutations of Lys16 to an uncharged residue, glutamine, reduce silencing, and mutation to arginine, even though positive charge is retained, also reduces silencing. Mutations in Lys5, 8, or 12 to arginine, in contrast, exert smaller effects on silencing. These findings are consistent with the idea that the acetylated Lys16 residue of H4 is critical for recognition by Sir2.

Figure 7:
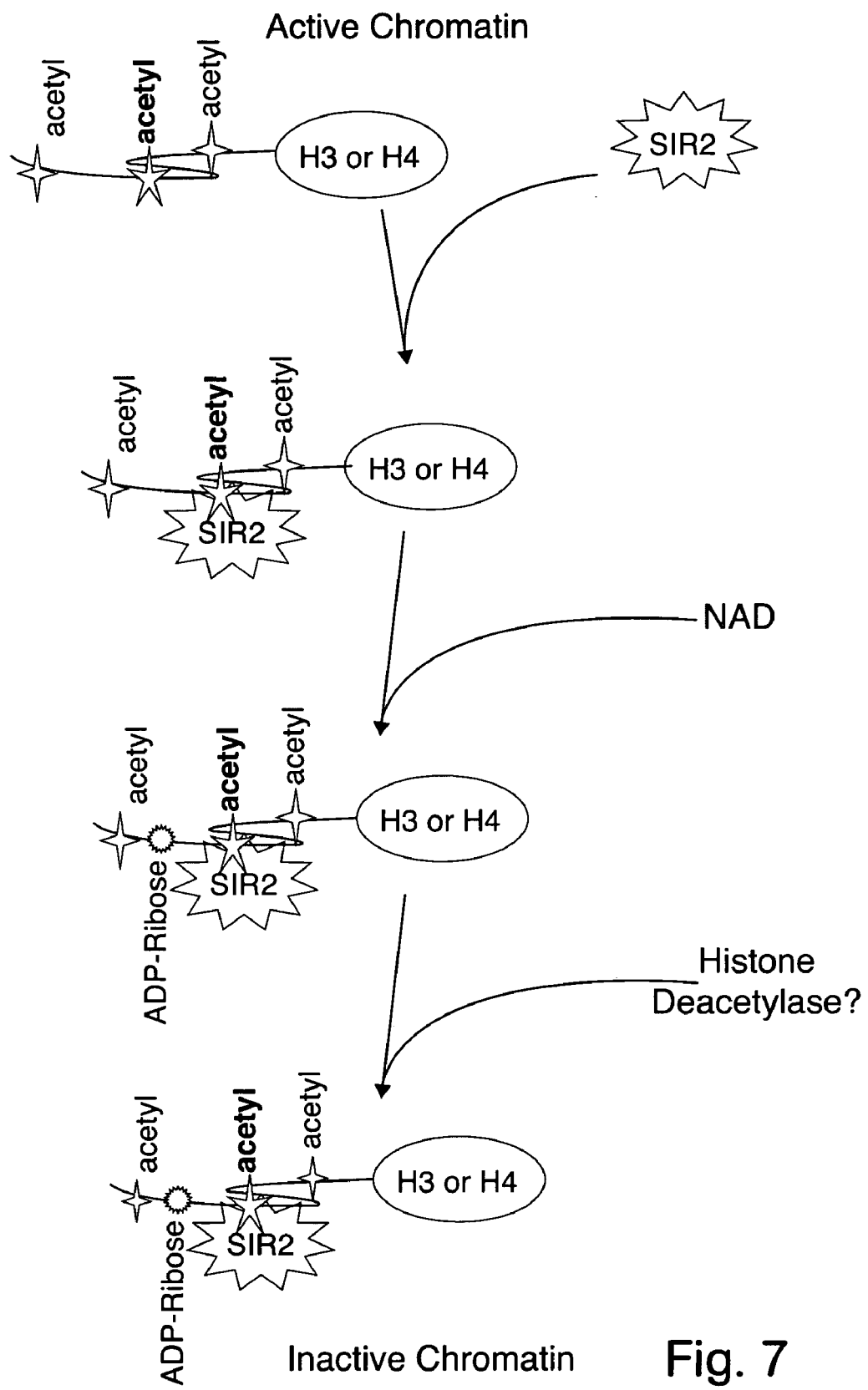
FIG. 7 is a diagrammatic representation of a model of Sir2-mediated modification of histone proteins H3 and H4.

ADP-ribosylation of histone N-terminal tails can lead to heterochromatin and gene silencing by interacting with histone residues that are constitutively acetylated, like Lys16 of mammalian H4, thereby inducing ADP-ribosylation by Sir2 proteins in one or more adjacent residues in the N-terminal tail (FIG. 7). In active chromatin, the lysines in the N-terminal tails of H3 and H4 are acetylated (depicted by stars at top). Sir2 recognizes H3 and H4 tails containing specifically acetylated lysines (indicated by a large star). Sir2 ADP-ribosylates these N-terminal tails, causing the formation of heterochromatin, perhaps by the recruitment of histone deacetylases. The ADP-ribosylation in turn facilitates silencing, for example, by restricting access of histone acetylases or by recruiting deacetylases, leading to the hypoacetylated state of other lysine residues in the tail and thus a tighter chromatin structure. ADP-ribosylation and deacetylation are targeted to specific regions of the genome by the selective recruitment of Sir2. In yeast, Sir3p and Sir4p facilitating targeting of Sir2p to telomeres and HM loci, and Net1p and perhaps other components of the RENT complex recruit Sir2p to the rDNA. Consistent with this model, overexpression of Sir2 induces a more global hypoacetylation of histones H2B, H3 and H4 in yeast.

The model depicted in FIG. 7 is consistent with the silencing phenotypes of several yeast mutants. Rpd3p is a histone deacetylase. Rpd3 mutants show hyperacetylation of histones and generally an increase in transcription of genes assayed. An exception to this rule, however, occurs in the case of silenced chromatin at yeast telomeres and rDNA, where silencing actually increases in the mutant. The increase in silencing can occur as a result of hyperacetylation of the lysines in the N-terminal tail that are recognized by Sir2. NAT1/ARD1 encode subunits of an N-terminal acetyltransferase. Mutations in either gene abolish silencing in yeast. It is possible that the nat1 or ard1 mutants have underacetylation of histone residues that potentiate Sir2 activity. Additionally, or alternatively, the effects of these mutants can be indirect.

Mammalian Sir2 Proteins

SIR2 homologs have been found in a variety of organisms. Human SIR2 homologs that all correspond to the same gene, mSIR2, which is most related to yeast HST2 have been reported (Afshar, et al., *Gene* 234:161-168 (1999); Frye, *Biochem. Biophys. Res. Commun.* 260:273-279 (1999); Sherman, et al., *Mol. Biol. Cell* 10:3045-3059 (1999)). In contrast, the human SIR2 gene appears to correspond to a fragment of a homolog of mSIR2α. Of all mammalian SIR2 homologs analyzed to date, mSIR2α shows the greatest homology to ySir2p in the evolutionarily conserved core domain. Nonetheless, there are some significant differences between ySir2p and mSir2α. mSir2α has a diverged N-terminal portion and a longer C-terminal tail and is almost twice the size of ySir2p. It is possible that these mSir2α-specific regions may be involved in species-specific or cell type-specific protein-protein interactions.

In yeast, the Sir complex moves to sites of DNA double strand breaks. Since ADP-ribosylation has been associated with sites of DNA repair in mammalian cells, it is likely that mammalian Sir2 proteins are recruited to DNA damage. Mono-ADP-ribosylation of histones near sites of DNA damage in yeast and mammals likely have an important biological role.

Link Between Energy Metabolism, Heterochromatin and Aging

The substrate for Sir2 modification of chromatin, NAD, may be an indicator of the energy status of cells. Cells grown under energy limitation may have a high NAD/NADH ratio, while cells growing under energy surplus would have a low ratio. Since NAD but not NADH is expected to function as a substrate in the mono-ADP-ribosylation reaction, Sir2 activity can be highest under conditions of energy limitation. Thus, the rate of energy metabolism may control gene expression of certain chromosomal domains by regulating the activity of Sir2.

Recent studies indicate that Sir2p is a limiting component in the determination of the life span of yeast mother cells for example, overexpression of Sir2p extends the life span beyond wild type. Caloric or dietary restriction is associated with an extension of life span in rodents, *C. elegans*, and even yeast. Caloric restriction may exert of its effect, in part, by creating a condition of energy limitation, which would activate Sir2 and promote ADP-ribosylation of chromatin and gene silencing. ADP-ribosylation is a biochemical event which has been suggested to play a role in aging. Alterations in the maintenance of Sir2-silenced chromatin could result in normal mammalian aging and by slowing caloric restriction. The fact that Sir2 proteins are simple enzymes suggests a strategy for intervening in non genetic ways to influence life span. Small molecules that are agonists for this enzyme can extend life span in yeast cells and in mammals.

The present invention shows that yeast Sir2p and its mouse homolog mSIR2α are ADP-ribosyltransferases and NAD hydrolases with specific histone substrates, the N-terminal tails of H3 and H4. Both activities are stimulated by acetylation in the histone tails, in particular Lys9Ac and Lys14Ac for H3, and Lys16Ac for H4. Acetylation of these lysine residues is important for silencing of chromatin in vivo. Mutations in the conserved sequences of mSir2α reduce ADP-ribosyltransferase activity in vitro and chromatin of the silencing activity in mouse NIH3T3 cells. The mSir2α protein is localized in the nuclei of mouse cells shown that acetylation—terminal tails of H3 and H4 trigger ADP-ribosyltransferase and NAD hydrolase activities of Sir2 proteins. The ADP-ribosylation and acetylation of histones proteins can be important in the formation of heterchromatin in eukaryotic cells.

The present invention shows that Sir2 proteins are novel NAD-dependent deacetylases specific for the N-terminal tail of histone H3. Although NAD and NADH are frequent enzyme cofactors in oxidation/reduction reactions, this is the first time NAD has been shown to drive a distinct enzymatic reaction in a substrate, such as a peptide of the amino-terminal tail of histone H3 di-acetylated at lysines 9 and 14.

Since histones in silenced chromatin are hypoacetylated, and because overexpressed Sir2p promotes global deacetylation of histones in yeast (Braunstein, M., et al., *Genes Dev* 7: 592-604 (1993); (Braunstein, M., et al., *Mol. Cell. Biol.* 16: 4349-4356 (1996)), it was originally proposed that Sir2p might be a histone deacetylase. However, such an activity could not be demonstrated until now, presumably because of its absolute requirement for NAD. The present invention is consistent with studies that show mutating lysines in the tails of histones H3 and H4 can reduce silencing in vivo (Thompson, J. S., et al., *Nature* 369: 245-247 (1994); (Braunstein, M., et al., *Mol. Cell. Biol.* 16: 4349-4356 (1996)) and suggest that this NAD-dependent deacetylation of histones per se is sufficient to establish silencing in vivo. These data show that SIR2 mutations reduce or eliminate deacetylase activity show corresponding defects in silencing, suppression of recombination, and life span in vivo. The nature of the requirement of NAD for deacetylation is not yet clear, but at the concentrations of about one hundred µM, NAD may serve as an allosteric effector to activate the histone deacetylase activity of Sir2. The failure of NADH, NADP, or NADPH to function as such reveals a remarkable specificity of Sir2p for the oxidized form of NAD. Sir2 proteins catalyze the putative transfer of ADP-ribose from NAD to the proteins such as intact histone H3 or the amino-terminal peptide and labeled NAD, to allow the detection of low levels of $^{32}P$ transfer. However, in reactions allowing a direct comparison between ADP-ribosylation and deacetylation (using the H3 peptide at 1 mM NAD), the reaction products displayed at least 27% conversion of the peptide to deacetylated species, and no detectable conversion to any ADP-ribosylated species. Thus, ADP ribosyltransferase reaction proceeds to a much lesser degree than deacetylation, at least with this H3 peptide substrate.

Coumermycin A1 is an inhibitor of mono-ADP-ribosyltransferases (Banasik, M., et al., *Mol. Cell. Biochem.* 138: 185-187 (1994)) and was shown to inhibit the putative ADP-ribose transferase activity as well as the accompanying NAD hydrolysis. However, coumermycin A1 did not inhibit the Sir2p deacetylase activity at all. These findings indicate that the putative ADP-ribosyltransferase activity is separable and may play a distinct role in vivo. The ADP-ribosylation of histones is known to occur when cells are treated with DNA damaging agents (Adamietz, P., et al., *J. Biol. Chem.* 259: 6841-6846 (1984); (Kreimeyer, A., et al., *J. Biol. Chem.* 259: 890-896 (1984); (Pero, R. W., et al., *Mutat. Res.* 142: 69-73 (1985)). Moreover, antibodies against mono-ADP-ribose react with mammalian nuclei only if when cells are treated with DNA-damaging agents. Thus ADP-ribosylation of histones and NAD hydrolysis may play a role in opening up chromatin to allow DNA repair. In this regard, the Sir proteins are known to move to sites of DNA breaks to aid their repair by non-homologous end joining (Mills, K. D., et al., *Cell* 97: 609-620 (1999); (Martin, S. G., et al., *Cell* 97: 621-633 (1999)).

There are four SIR2-related genes in yeast, HST1-4 (Brachmann, C. B., et al., *Genes Dev.* 9: 2888-2902 (1995)), but no single hst mutant affects silencing, although effects are observed in the hst3/hst4 double mutant. It is expected that the these gene products catalyze histone deacetylation. In mammals there are at least five homologs (Frye, R. A., *Biochem. Biophys. Res. Commun.* 260: 273-279 (1999); (Brachmann, C. B., et al., *Genes Dev.* 9: 2888-2902 (1995)), of which mSir2α is the most closely related to Sir2p. mSir2α is identical to yeast Sir2p in the deacetylation reaction, indicating that this activity is highly conserved in nature.

mSir2α is not at the rDNA, centromeres, or telomeres, but broadly distributed in nuclei (not shown) suggesting that Sir2 proteins may regulate silencing in widely distributed blocks of the mammalian genome. A distinction between Sir2-silenced heterochromatin and constitutive heterochromatin is illustrated by the disruption of centromeric heterochromatin in *S. pombe* by the general deacetylase inhibitor, trichostatin A (TSA) (Ekwall, K., et al., *Cell* 91: 1021-1032 (1997)), which does not affect the deacetylase activity of Sir2p. The involvement of a distantly related SIR2 family member, hst4+, in this centromeric silencing (Freeman-Cook, L. L., et al., *Molecular Biology of the Cell* 10: 3171-3186 (1999)) provides a hint that the more distant SIR2 family members may target constitutive heterochromatin, while closely related SIR2 genes target regulated blocks of silencing.

In addition to a role in silencing, Sir2p also extends life span of mother cells by repressing recombination in the rDNA (Gottlieb, S., et al., *Cell* 56: 771-776 (1989)), and reducing the production of toxic rDNA circles (Sinclair, D. A., et al., *Science* 277: 1313-1316 (1997); (Sinclair, D. A., et al., *Cell* 91: 1-20 (1997)). The fact that NAD but not NADH, NADP, or NADPH can activate deacetylation of histones by Sir2p may link chromatin silencing and ageing to the metabolic state of cells, i.e., Sir2 proteins can sense the energy or oxidation state of cells. Most of the NAD in eukaryotic cells is present in the nucleus (Rechsteiner, M., et al., *Nature* 259: 695-696 (1976)), where it turns over rapidly (Dai, Y., et al., *Mut. Res.* 191: 29-35 (1987)). Thus, a pool of NAD can regulate chromatin structure by controlling the histone deacetylase activity of Sir2 proteins.

It is interesting to note that caloric restriction slows ageing in a variety of organisms, including yeast (Muller, I., et al., *Mech. Ageing Dev.* 12: 47-52 (1980)), *C. elegans* (Lakowski, B., et al., *Proc. Natl. Acad. Sci. USA* 95: 13091-13096 (1998)), rodents (Weindruch, R. H., et al., *J. Nutrit.* 116: 641-654 (1986)), and probably primates (Roth, G. S., *J. Am. Geriatr. Soc.* 47: 896-903 (1999)). It is possible that the altered metabolic rate in calorically restricted cells exert at least part of its effect by increasing the availability of NAD in the nucleus, which, in turn, up-regulates Sir2 proteins and chromatin silencing. The hunkering down of the genome in the face of carbon limitation is sensible because it conserves energy and could explain the extended life span under this regimen. In normal ageing, NAD levels decline (Chapman, M. L., et al., *Mech. Of Aging and Dev.* 21: 157-167 (1983)), perhaps causing a decrease in Sir2 activity and a deleterious loss of genomic silencing.

It is clear that nuclei obtained from adult animals may be reprogrammed in oocytes to undergo embryonic development and produce viable progeny (Wilmut, I., et al., *nature* 385: 810-813 (1997); (Wakayama, T., et al., *Nature* 394: 369-374 (1998)). This cloning implies that there can be no irreversible changes in nuclei of ageing animals, such as DNA deletions or DNA circles. Were changes in chromatin structure the basis of ageing, then such a reversibility in oocytes would be theoretically possible. It is possible that reprogramming of adult nuclei, a slow and inefficient process, can be facilitated by the addition of chromatin modification factors, such as Sir2 to oocytes. Moreover, it possible that increasing the activity of Sir2 in metazoans extends their life span, as it does in yeast (Kaeberlein, M., et al., *Genes Dev.* 13: 2570-2580 (1999)). The most ready way to achieve this goal is to provide additional copies of SIR2 genes in transgenic animals. A more long term strategy with possible implications to humans is to intervene with small molecules that increase the deacetylation activity of Sir2. The latter approach offers the advantage of late intervention to avoid any unwanted side effects on development or fertility and could, in principle, afford the benefits of caloric restriction without the practical difficulties.

While this invention has been particularly shown and described with references to preferred embodiments thereof, it will be understood by those skilled in the art that various changes in form and details may be made therein without departing from the scope of the invention encompassed by the appended claims. The teachings of all references cited herein are hereby incorporated by reference in their entirety.

EXEMPLIFICATION

Materials and Methods

Data Base and Sequence Analysis

TBLASTN searches were performed on the NCBI mouse EST sequence databases, using the amino acid sequence of ySir2p. All mouse EST sequences homologous to ySir2p were classified into three groups termed α, β, and γ, based on the homology results from the searches. Three representative EST cDNA clones were purchased for three mouse homolog groups from Genome Systems Inc (St. Louis, Mo.): AA199012 for α, AA105536 for β, and AA260334 for γ. The cDNA clones were partially or completely sequenced. All deduced amino acid sequences were aligned with the Clustal X program. To cover each core domain completely, amino acid sequences of AA137380 and AA212772 for β and γ respectively, were also used. A phylogenetic tree of the core domains of the yeast and mouse Sir2 families was generated with the Clustal X and NJPLOT program by using the following amino acid sequences: position 228-499 for ySir2p, 174-440 for yHst1p, 1-251 for yHst2p, 26-315 for yHst3p, 65-343 for yHst4, 215-460 for mSir2α, TLGL (SEQ ID NO:36) to LINKEK (SEQ ID NO:32) for mSir2β, and FGGG (SEQ ID NO:37) to LINRDL (SEQ ID NO:33) for mSIR2γ.

Northern Blotting

The multiple tissue Northern blot (heart, brain, spleen, lung, liver, skeletal, muscle, kidney, testis) was purchased from Clontech (Palo Alto, Calif.). Prehybridization and hybridization were performed at 65° C. in 5×SSPE, 5×Denhardt's solution, 1% SDS and 0.1 mg/ml poly(A). The cDNA fragments of AA199012, AA105536, and AA260334 were used as probes for mSIR2α, β, and γ, respectively. The human β actin fragment from the manufacturer was used as a control probe. Between each blotting, the probe was stripped off by boiling the membrane in 0.5% SDS for 1 min.

Molecular Cloning of mSIR2α

The mouse 15-day embryo 5'-STRETCH PLUS cDNA library (Clontech) was screened with the cDNA fragment of AA199012 as a probe. Five positive clones were obtained from approximately one million independent plaques. One of the five clones contained a 3.9 kb cDNA fragment. The nucleotide sequence of this fragment was determined with an Applied Biosystems 374 automated sequencer. Although more 5' sequences of mSIR2α cDNA were obtained by 5' RACE with the mouse liver Marathon-Ready cDNA (Clontech), no stop codon could be found in the upstream of the first start codon (data not shown). This finding was confirmed on the genomic sequence of the mSIR2α gene (data not shown). Thus, the cDNA clone encodes the full-length mSir2α protein, as shown in FIG. 2B. The deduced amino acid sequence of mSir2α was aligned in the Clustal X and SeqVu 1.1 programs with other Sir2 family members.

Antibody Production to mSir2α

The 5' SalI-PvuI fragment of the mSIR2α cDNA was engineered to be cloned into BamHI site of pET16b vector (Novagen, Madison, Wis.). The BL21(DE3)pLysS bacterial strain that also has an extra copy of arginine tRNA gene was transformed with the resultant plasmid. A transformed bacterial clone was induced in 1 mM IPTG at 37° C. for 7 hrs to produce 10×His-tagged N-terminal fragment of the mSir2α protein. The mSir2α N-terminal protein was purified with Ni-NTA agarose (QIAGEN, Valencia, Calif.) under denaturing condition. Rabbit polyclonal antisera against this purified protein was produced at Covance Research Products (Denver, Pa.). Affinity purification of the antibody was performed with HiTrap NHS-activated column (Amersham Pharmacia Biotech, Piscataway, N.J.) conjugated with the dialyzed mSir2α N-terminal protein.

Western Blotting and Immunoprecipitation

Mouse NIH3T3 cells were lysed directly in Laemmli's sample buffer for Western blotting or in extraction buffer (20 mM Tris-HCl [pH7.6], 150 mM NaCl, 0.5% IGEPAL CA-630 (SIGMA, St. Louis, Mo.), 1 mM EDTA, 0.5 mM PMSF, 10 μg/ml leupeptin, 10 g/ml pepstatin A, 10 μl/ml aprotinin) for immunoprecipitation. The in vitro translated mSir2α protein was produced with the XbaI-linearized pBluescript containing the mSIR2α cDNA at SalI site and the STP3 T7 in vitro transcription/translation kit (Novagen). For Western blotting, 17 μg of the extract or 211 of the in vitro translation mixture was run on a 4-15% gradient SDS-PAGE gel and transferred onto an Immobilon-P PVDF membrane (Millipore, Bedford, Mass.). After preblocking strips of the membrane in TBS containing 0.1% Tween20 and 5% nonfat skim milk, the first antibody reaction was performed in the 1:2000 dilution of the affinity-purified antibody against mSir2α or control rabbit IgG. The mSir2α band was visualized with the secondary anti-rabbit IgG antibody conjugated with horse radish peroxidase and the ECL detection kit (Amersham Pharmacia Biotech). For immunoprecipitation, approximately 300 μg of the extract was incubated at 4° C. with 1 μg of the affinity-purified mSir2α antibody for 1 hr and then with Protein A-Sepharose beads (SIGMA) for another 1 hr. The protein complex on beads was washed with extraction buffer three times and extracted in sample buffer. The protein was electrophoresed and blotted as described above.

Immunofluorescence

NIH3T3 cells or mouse embryonic fibroblasts were plated on 10-well multitest slideglasses (ICN Biomedicals, Aurora, Ohio). The cells were briefly washed with PBS, fixed in PBS containing 3.2% paraformaldehyde for 10 min, and then treated with PBS containing 0.5% IGEPAL-CA630 for 20 min. Preblocking reaction was performed with PBG buffer (PBS containing 0.2% cold water fish gelatin and 0.5% bovine serum albumin (SIGMA)) at 37° C. for 20 min. After washing cells in PBS-T (PBS containing 0.2% Tween20) briefly, the first antibody reaction was performed at 37° C. for 1 hr in PBG containing the affinity-purified mSir2α antibody diluted to 1:500 and/or one of the anti-human nuclear antibodies (ANA-N for nucleolus or ANA-C for centromeres, SIGMA) diluted to 1:5 or 1:10 or control rabbit IgG. The cells were washed in PBS-T for 5 min twice. The secondary antibody reaction was performed at 37° C. for 1 hr with the anti-rabbit IgG antibody conjugated with FITC (Jackson ImmunoResearch Laboratories, PA) and/or the anti-human IgG antibody conjugated with Texas-Red (Vector Laboratories, CA). After washing in PBS-T for 5 min, the cells were counterstained in 200 ng/ml of DAPI for 1 min. They were washed in TBS-T for 5 min again and in $dH_2O$ briefly, and then embedded under coverslips with Vectorshield (Vector Laboratories).

For the immuno-FISH of mSir2α and telomeres, the first antibody reaction for mSir2α was performed as described above. The cells with the first immune complex was then fixed with 3.2% paraformaldehyde for 10 min, permealized again in PBS containing 0.5% IGEPAL-CA630 for 20 min, treated in 0.1 M NaOH for 2 min to denature DNA, and immediately washed in ice-cold PBS. The synthesis of a telomeric probe, hybridization of the probe and visualization of the hybridized spots were done as described previously. The secondary antibody reaction to detect mSir2α was also done during the last visualization step.

All immunofluorescent digital images were obtained with the Nikon Eclipse TE300 fluorescent microscope equipped with a CCD digital camera (Hamamatsu Photonics, Japan) and the Metamorph imaging system software (Universal Imaging Corp., PA).

Production of Recombinant Proteins

The yeast SIR2 gene or the mSIR2a full-length cDNA was cloned into pET28a vector (Novagen). BL21 (DE3) and BL21 (DE3)pLysS with an extra copy of arginine tRNA gene was transformed with the ySIR2 and mSIR2α plasmids, respectively. Each transformed bacterial clone was induced in 1 mM IPTG at 37° C. for 1 hr. The induced 6×His-tagged proteins were purified with Ni-NTA agarose under native condition (see FIG. 4A). The N-terminal fragment of mSir2α was prepared in the same way. The control elute was prepared from a bacterial clone carrying pET28a vector only. The recombinant proteins were aliquoted and kept at −70° C.

Site-directed mutagenesis of mSIR2α core domain was performed with the GeneEditor system (Promega, Madison, Wis.) according to the procedure provided by the manufacturer. The mutant recombinant proteins were prepared in the same way as described above.

ADP-Ribosylation Assay

The typical reaction was performed in 50 or 100 µl of the buffer containing 50M Tris-HCl [pH8.0 or 9.0], 4 mM $MgCl_2$, 0.2 mM DTT, 1 µM cold β-$NAD^+$ (SIGMA) and 8 µCi nicotinamide adenine dinucleotide 5'-[α-$^{32}$P]triphosphate (NAD) as a donor of ADP-ribose (~1000 Ci/mmol, Amershan Pharmacia Biotech). To check the sensitivity to poly- or mono-ADP-ribosylation inhibitors, 3-aminobenzamide (ICN Pharmaceuticals, CA), benzamide, novobiocin and coumermycin A1 (SIGMA) were added to the reactions prior to adding Sir2 proteins, respectively. The wild type or mutant recombinant proteins (0.5-1 µg for ySir2p and 10 µg of mSir2α) were added with 4 µg of each histone purchased from Roche Molecular Biochemicals (Indianapolis, Ind.). For the peptide experiments, 5-10 µg of unacetylated or acetylated N-terminal tail peptides (amino acids 1-20) of H3 and H4 purchased from Upstate Biotechnology (Lake Placid, N.Y.) were used as substrates of the yeast and mouse Sir2 recombinant proteins.

To detect the activity of the endogenous mSir2α, which was usually immunoprecipitated from 300-400 µg of the NIH3T3 whole cell extract, the reaction buffer and substrates were added directly to the immune complex on Protein A-Sepharose beads. The reaction mixture was incubated at room temperature for 1 hr. For the reaction of snake venom phosphodiesterase (Roche Molecular Biochemicals), 1-2 µl of the enzyme or the same volume of $dH_2O$ was added to the reaction mixture, respectively, after finishing ADP-ribosylation reaction. Each mixture was incubated at 37° C. for 1 hr and the reaction was terminated as described below.

To analyze histone modification, 25 µl of 100% trichloroacetic acid (TCA) solution was mixed to the reaction mixture and left on ice for 15 min. The protein precipitates were centrifuged at 4° C. and washed with 5 or 20% TCA solution twice. The pellets were dissolved in 15 µl of Leammli's sample buffer and boiled for 1.5 min. The proteins were electrophoresed in a 10-20% gradient SDS-PAGE gel. The gel was stained with Coomassie Brilliant Blue R-250 (GibcoBRL Life Technologies, Frederick, Md.) to check equal loading of histones, dried, and exposed to Kodak X-OMAT film.

To analyze modified peptides, 10 µl of each reaction mixture was spotted on a cellulose TLC plate (EM Science, Gibbstown, N.J.). The chromatography was performed for 9-10 hrs in a TLC chamber containing the 65:5:3:2:29 mixture of isobutyric acid, pyridine, acetic acid, butanol and water. The plate was dried and exposed to Kodak X-OMAT film. The peptide spots were visualized by ninhydrin staining.

Transient Transfection Assay

Effector plasmids of mSIR2α were constructed using DNA fragments corresponding to amino acids 220-500 of the wild type and mutant mSIR2α amplified by PCR with Pfu Turbo DNA polymerase (Stratagene, La Jolla, Calif.) with primers that create EcoRI sites at both ends of each fragment. Fragments were cloned into the EcoRI site of pM mammalian expression vector (Clontech) to produce the N-terminal fusion protein to the GAL4 DNA binding domain. The luciferase plasmid, $pUAS_4tkluc$, which has four GAL4 binding sites in the upstream of the luciferase gene, was employed as a reporter gene. Plasmids preparations were made using the QIAfilter plasmid midi kit (QIAGEN).

NIH3T3 cells ($10^6$ cells) were plated a day before transfection. Cells were transfected using SuperFect transfection reagent (QIAGEN) with 4 µg of the GAL4 DBD-core domain effector plasmid, 1 µg of the luciferase reporter gene and 1.5 µg of SV40 promoter-driven β-galactosidase gene to normalize the transfection efficiency. The extracts of the transfectants were prepared 48 hrs after transfection. The luciferase assay was performed using the luciferase assay system kit (Promega) and the Optocomp I luminometer (MGM Instruments, CT), according to the procedures provided by the manufacturers.

Production of Recombinant Proteins

The yeast SIR2 gene or the mSIR2α full-length cDNA were cloned into pET28a vector (Novagen, Wis.). BL21 (DE3) and BL21(DE3)pLysS with an extra copy of arginine tRNA gene was transformed with the SIR2 and mSIR2α plasmids, respectively. Each transformed bacterial clone was induced in 1 mM IPTG at 37° C. for 1 hr. The induced 6×His-tagged proteins were purified with Ni-NTA agarose under native conditions. The control elute was prepared from a bacterial clone carrying pET28a vector only. The recombinant proteins were aliquoted and kept at −70° C.

Deacetylation and ADP-Ribosylation Assays

The typical reaction of Sir2 deacetylase activity was performed in 50 µl of buffer containing 50 mM Tris-HCl [pH 9.0], 4 mM $MgCl_2$, 0.2 mM DTT, variable concentration of cold nicotinamide adenine dinucleotide (NAD) or NAD derivatives (SIGMA, MO), 5-10 µg of the purified recombinant Sir2 proteins, and 10 µg of the histone H3 N-terminal tail peptide (amino acid 1-20) di-acetylated at positions 9 and 14 (Upstate Biotechnology, NY). This starting peptide material contains a contaminant with 100 Da smaller molecular weight, which also showed exactly the same patterns of deacetylation (data not shown). To detect the ADP-ribosylation activity, 8 µCi of NAD 5'-[α-$^{32}$P]triphosphate (~1000 Ci/mmol, Amersham Pharmacia Biotech, NJ) was added to the same reaction containing 1 µM cold NAD. Histone H3 protein (4 µg) (Roche Molecular Biochemicals, IN) were used for this assay. All reaction mixtures were incubated at room temperature for 1 hr. Trichostatin A and coumermycin A1 (SIGMA) were prepared in dimethylsulfoxide (DMSO, SIGMA), and 5 µl of solvent or inhibitor was added to the reactions prior to adding Sir2 proteins.

Analysis of Deacetylated or ADP-Ribosylated Products

After the incubation, the products were precipitated at −20° C. overnight by adding 50 µl of distilled water and 25 µl of 100% trichloroacetic acid (TCA) solution. For high pressure liquid chromatography (HPLC), the precipitates were reconstituted in 5% $CH_3CN$ and 0.1% trifluoroacetic acid (TFA) and run in the gradient concentration between 0.05% TFA and 0.043% TFA plus 80% $CH_3CN$ on Hewlett Packard Model 1100 HPLC system with 214TP52 column (VYDAC, CA). The chromatograms at the absorbance of 210 nm were digitally recorded and analyzed by Hewlett Packard ChemStation system (version A.06.03[509]). Fractions of samples were collected every 1 min by Gilson Fraction Collector Model 203. Peptide sequencing was done by the Applied Biosystems Procise 494 HT protein sequencing system. PTH amino acid chromatograms were recorded and analyzed by the ABI Model 610A2.1 data integration/analysis system.

Electron-spray mass spectroscopy (also referred to herein as mass spectroscopy) was done on the PE Sciex Model API365 system. Matrix assisted laser desorption/ionization (MALDI) mass spectroscopy can also be used. The electron-spray mass spectroscopy data were analyzed by the BioMultiView program (version 1.3.1). To detect the ADP-ribosylated intact H3 protein, the pellets were dissolved in 15 µl of Leammli sample buffer, boiled for 1.5 min and electrophoresed in a 10-20% gradient SDS-PAGE gel. The gel was stained with Coomassie Brilliant Blue to check equal loading of histones, dried, and exposed to Kodak X-OMAT film. To analyze the ADP-ribosylated H3 peptides, 10 µl of each reaction mixture was spotted on a cellulose TLC plate (EM Science, NJ). The chromatography was performed for 9-10 hrs in a TLC chamber containing the 65:5:3:2:29 mixture of isobutyric acid, pyridine, acetic acid, butanol and water (Scheidtmann, K. H., et al., *J. Virol.* 44: 116-133 (1982)). The plate was dried and exposed to Kodak, X-OMAT film. The peptide spots were checked by ninhydrin staining.

Molecular Cloning of mSIR2α

The mouse 15-day embryo 5-STRETCH PLUS cDNA library (Clontech, CA) was screened with the EST cDNA fragment of AA199012 as a probe. Five positive clones were obtained from approximately one million independent plaques. One of the five clones contained a 3.9 kb cDNA fragment. The nucleotide sequence of this fragment was determined with an Applied Biosystems 374 automated sequencer. The isolated cDNA clone encodes the full-length mSir2α protein since the in vitro-translated protein from this cDNA clone showed an indistinguishable size (10-120 kD) to the protein in the mouse NIH3T3 extract recognized by a specific polyclonal antibody against a N-terminal portion of mSir2α (data not shown).

The amino acid sequences of mSir2α and other Sir2 family members were aligned in the Clustal X program and a phylogenetic tree was generated by using the NJPLOT program.

Strains, Plasmids, and Antibodies

All strains used were derivatives of W303a sir2ΔE: W303R sir2ΔE (MATa, ade2-1, leu2-3,112, trp1-1, ura3-52, his3-11, sir2::TRP1, rDNA-ADE2), W303RT sir2ΔE (MATa, ade2-1, leu2-3,112, trp1-1, ura3-52, his3-11, rad5-535, sir2::TRP1, rDNA-ADE2, URA3-TEL???), and W303R sir2ΔE/rpd3ΔE (MATa, ade2-1, leu2-3,112, trp1-1, ura3-52, his3-11, rdp3::URA3, sir2::TRP1, rDNA-ADE2). Two integrating plasmids that contain SIR2 driven by its native promoter were used: pRS305-SIR2 and pRS305-SIR2*, the latter expressing Sir2p at low levels. SIR2 and mutant sir2 strains were generated by cutting the plasmid within the LEU2 gene and integrated using standard yeast transformation protocols. Unless otherwise noted derivative strains were generated using pRS305-SIR2. Rabbit antibodies to Sir2p were generated by using full-length rSir2β isolated under denaturing conditions.

Generation of Core Domain Mutants

Site directed mutations were generated in the plasmid pRS305-SIR2* using the Gene Editor system (Promega, Madison, Wis.) according to the procedure provided by the manufacturer. Sequences were verified by Sanger sequencing methods. The mutants were then subcloned into pRS305-SIR2 and pET28a.

ADP-Ribosylation and Deacetylation Assays

BL21 with SIR2 or the sir2 mutants subcloned into pET28a (Novagen) were induced with 1 mM IPTG for 1 hr. The recombinant proteins were purified by Nickel-NTA column under native condition. Ribosylation and deacetylation assays were performed using 1 µg of recombinant protein for the ribosylation assay and 5 µg for the deacetylation assay.

Silencing, Life Span and rDNA Recombination Assays

To evaluate silencing at the telomeres and rDNA, 10-fold dilutions of the derivatives of either W303RT or W303R ΔErpd3 were spotted on media containing 5-FOA or media lacking adenine, respectively. To assay for HM silencing, W303R derivatives generated with pRS305-SIR2* were patched onto YPD with the tester strain CKy20(MATa, arg1, tsm11) and after overnight growth were replica plated to minimal media with no supplemented amino acids. Life span and rDNA recombination rates were measured as in Kaeberlein, et. al., (Kaeberlein, M., et al., *Genes Dev.* 13: 2570-2580 (1999)).

Results

Characterization of the Closest Mouse SIR2 Homolog, mSIR2α

At least three different sequences, mSir2α, β, and γ, related to yeast Sir2p (ySir2p) have been identified in the mouse EST database. mSir2α was identified as having the greatest homology to ySir2p and the related yeast protein, Hst1p (FIG. 1A). mSir2β and γ have significant homology to Hst2p, another member of yeast Sir2 family.

Figure 1B:
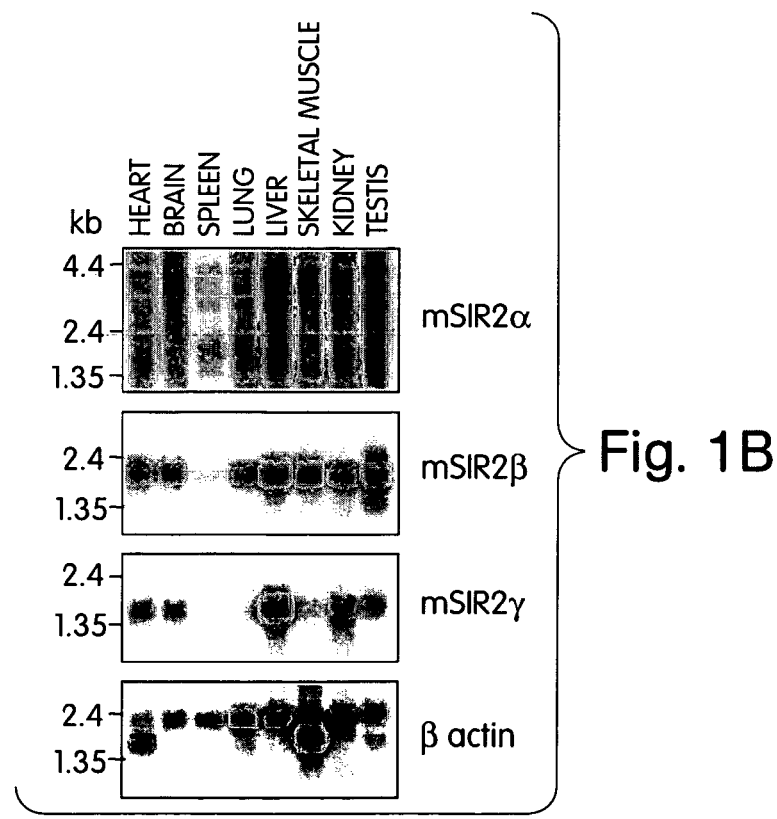
FIG. 1B is a Northern blot analysis of the tissue distribution of murine SIR2α, β, and γ mRNA transcripts.

The tissue distribution of mSIR2α, β, and γ mRNA expression was examined (FIG. 1B). A major transcript encoding mSIR2α (~4.0 kb) is present in all tissues examined. Minor transcripts of various size are also detected in each tissue. mSIR2 has only one transcript (~1.9 kb). mSIR2α and β appear to be expressed ubiquitously, showing a high level of expression in liver. The mSIR2γ transcript (~1.6 kb) is also predominantly expressed in liver.

A 3.9 kb cDNA clone of mSIR2α was identified by screening a mouse embryonic cDNA library with the EST clone AA199012 as a probe. This cDNA clone encodes a predicted protein with 737 amino acids with a molecular weight of 80.3 kD. The deduced amino acid sequence of mSIR2α is shown in FIG. 2A. A predicted nuclear localization signal KRKKRK (SEQ ID NO: 29) is present.

A rabbit polyclonal antibody raised against the N-terminal 131 amino acids of the mSir2α protein recognized a 120 kD protein in the cell extracts of murine NIH3T3 cells (FIG. 2B) and embryonic fibroblasts (data not shown). The in vitro translated (IVT) protein from the cDNA clone has an indistinguishable size to the protein in the NIH3T3 extract, suggesting that this cDNA clone encodes a full length protein of mSir2α (right panel, FIG. 2B). The 120 kD band was not detected in immunoprecipitates incubated with rabbit IgG alone or the in vitro translation mixture containing no RNA (FIG. 2B). An asterisk indicates IgG in immunoprecipitates.

In the mSir2α, the greatest homology to ySir2p resides in the middle or core domain of the protein (FIG. 2C). The amino acid identity of the mSir2α core domain to ySir2p is 45.9% and the N-terminal region of the mSir2α protein also shows weak homology to ySir2p (13.4% identity). The mSir2α has a longer C-terminal region than ySir2p, but no significant homology to other proteins in this region. The highly conserved core domains of yeast and mouse SIR2 family members have homology to the *Salmonella typhimurium* CobB protein (Tsang, A. W., et al., *J. Biol. Chem.* 273: 31788-31794 (1998)) (20.3% identity in the core domain (FIG. 2D). Asterisks denote a motif of putative NAD binding clefts conserved in known mono-ADP-ribosyltransferases. (FIG. 2C).

Figure 3:
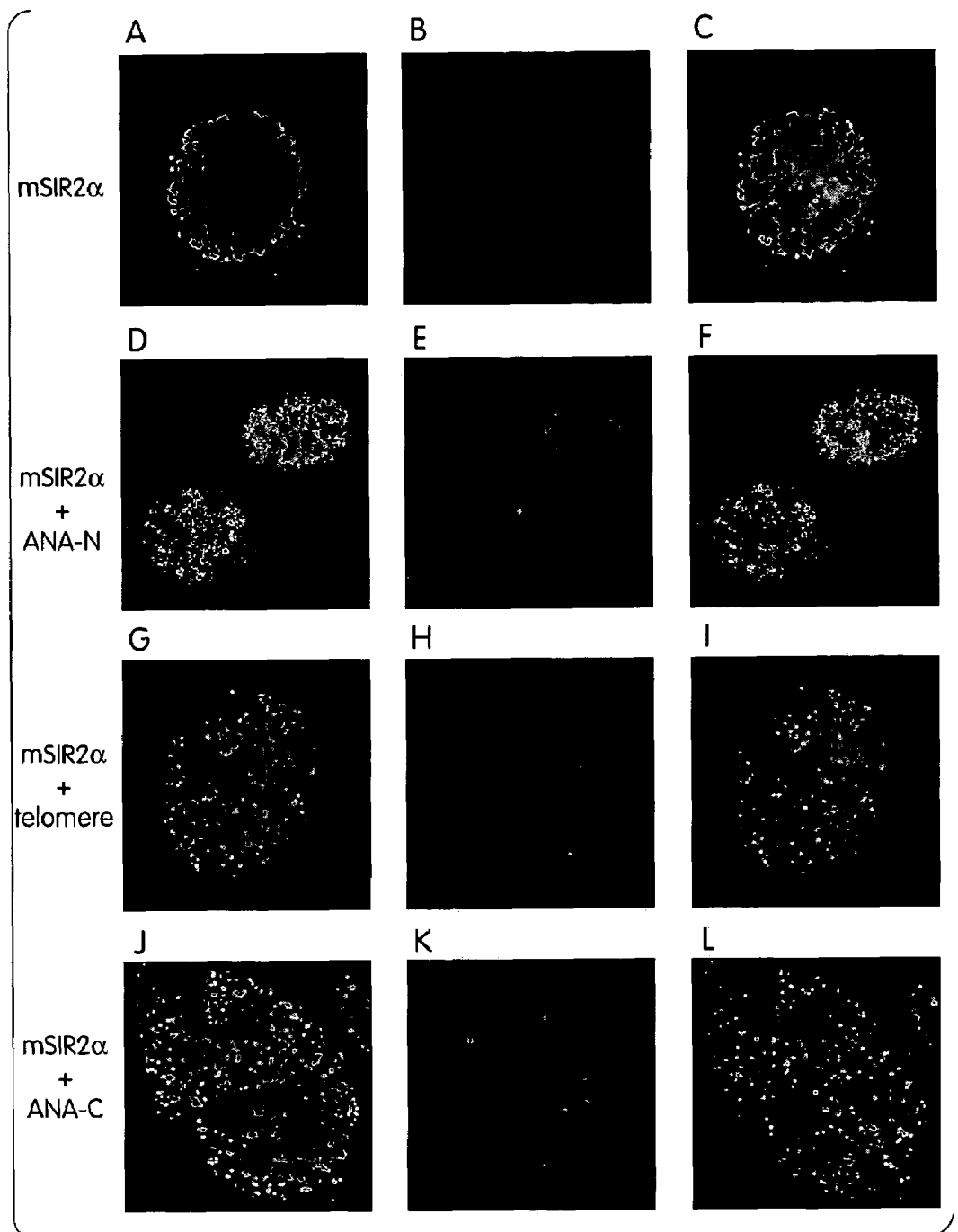
FIG. 3 depicts the immunocytochemical localization of mSir2α in mouse NIH3T3 cells (A, D, G, and J). Cells were counterstained with DAPI (B, E, H, and K). Nucleoli (E), telomeres (H), and centromeres (K) were visualized using an anti-human nucleolar antibody (ANA-N), telomeric FISH, and an anti-human centromeric antibody (ANA-C), respectively. Merged images are shown in C, F, I, and L.

In yeast, immunostaining revealed Sir2p localization in the nucleolus and telomeres (Gotta, M., et al., *Embo J.* 16: 3243-3255 (1997)). Immunostaining of mouse NIH3T3 cells with a polyclonal antibody raised against the N-terminal fragment of mSir2α localized mSir2α in the nucleus (FIG. 3A). DAPI-dense regions in nuclei, which correspond to mouse centromeres, were excluded (FIGS. 3B and C). This staining pattern was observed throughout the cell cycle except on mitotic chromosomes, which lacked staining (data not shown). Surprisingly, mSir2α was not localized to nucleoli, telomeres, or centromeres by co-immunofluorescence (FIG. 3, D-F, G-I, J-L) indicating that is not associated with the most highly repeated DNA in the mouse genome.

Yeast and Mouse Sir2 Proteins are Novel Nuclear Mono-ADP-Ribosyltransferases

Figure 4A:
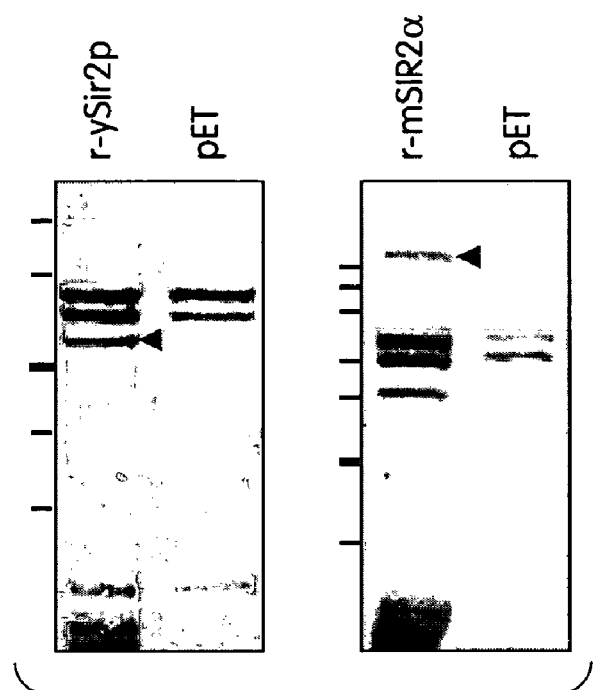
FIG. 4A is a Coomassie blue stained gel of 6×His-tagged recombinant yeast (r-y Sir2p) and murine (r-m Sir2α) Sir2 proteins purified with Ni-NTA agarose under native conditions. Arrowheads indicate each full-length protein.
Figure 4B:
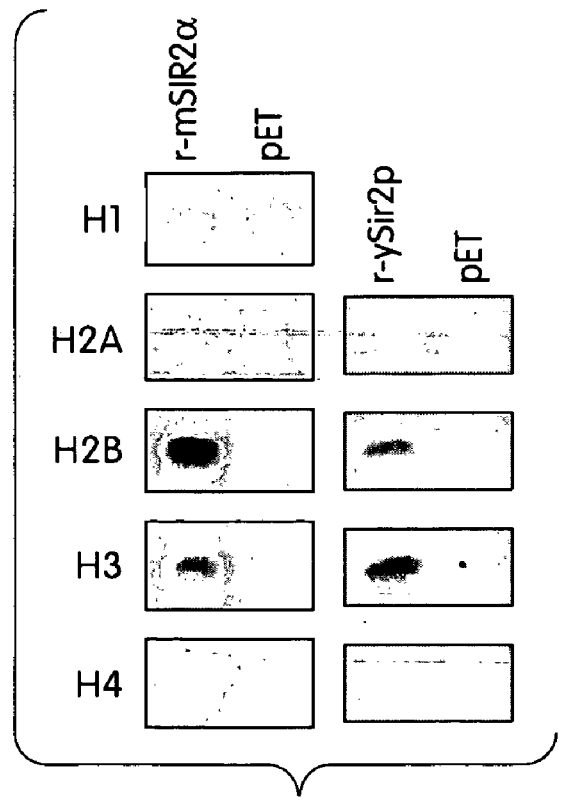
FIG. 4B depicts the results of ADP-ribosylation of histone proteins H1, H2A, H2B, H3 and H4 by recombinant r-ySir2p and r-mSir2α.

The ADP-ribosylase activity of bacterial recombinant full-length proteins of ySir2p and mSir2α was determined in in vitro assays (FIG. 4A). Calf thymus histones were used as substrates and $^{32}$P-labeled nicotinamide adenine dinucleotide (NAD) as a donor of ADP-ribose. Reaction products were visualized by SDS-PAGE. The recombinant rySir2p and r-mSir2α proteins transferred radioactive ADP-ribose to H2B and H3, but not to H1, H2A and H4 (FIGS. 4B, C). The Sir2 proteins modified H2B and H3 in a dose-dependent manner, the ADP-ribosylase activity did not reside in the mSir2α-specific N-terminal fragment N-ter (FIG. 4D). As shown in the upper panel of FIG. 4D, 5, 10, and 15 μg of recombinant full-length mSir2α (r-mSir2α) or its N-terminal fragment (N-ter) or control eluate (pET) were added to the reaction with histone H2B. Only the full-length protein showed the dose-dependent modification. As shown in the lower panel of FIG. 4D, 100, 250, 500, and 1000 ng of recombinant full-length ySir2p (r-ySir2p) were added to the reaction with histone H3. ADP-ribosylase activity was not observed when histone proteins were incubated with control pET alone (FIG. 4B).

Figure 4C:
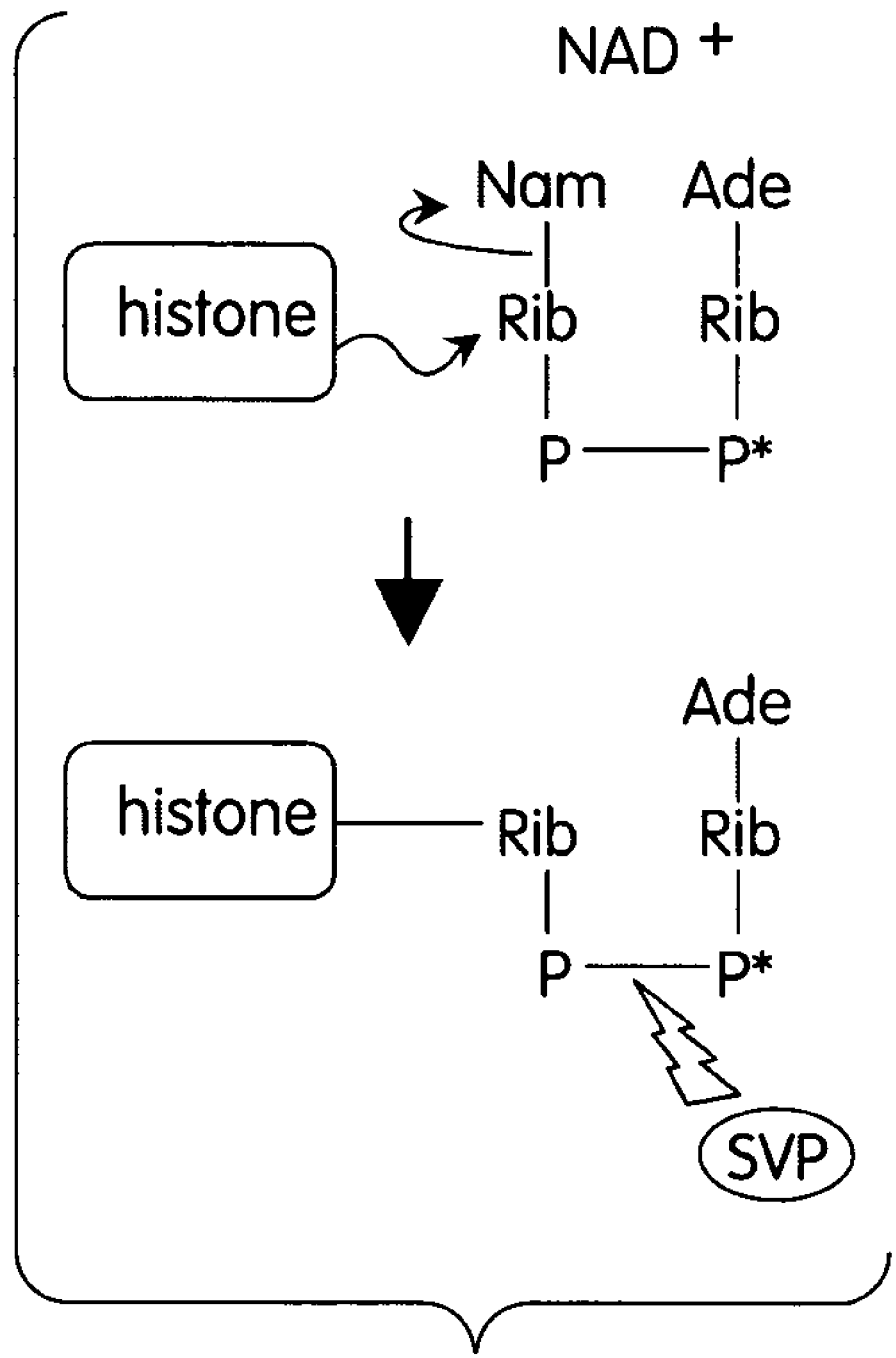
FIG. 4C illustrates ADP-ribosyltransferases cleaving nicotinamide (Nam) from $NAD^+$ (Ade-Rib-P*) creating a linkage between ribose (Rib) and histone proteins.
Figure 4D:
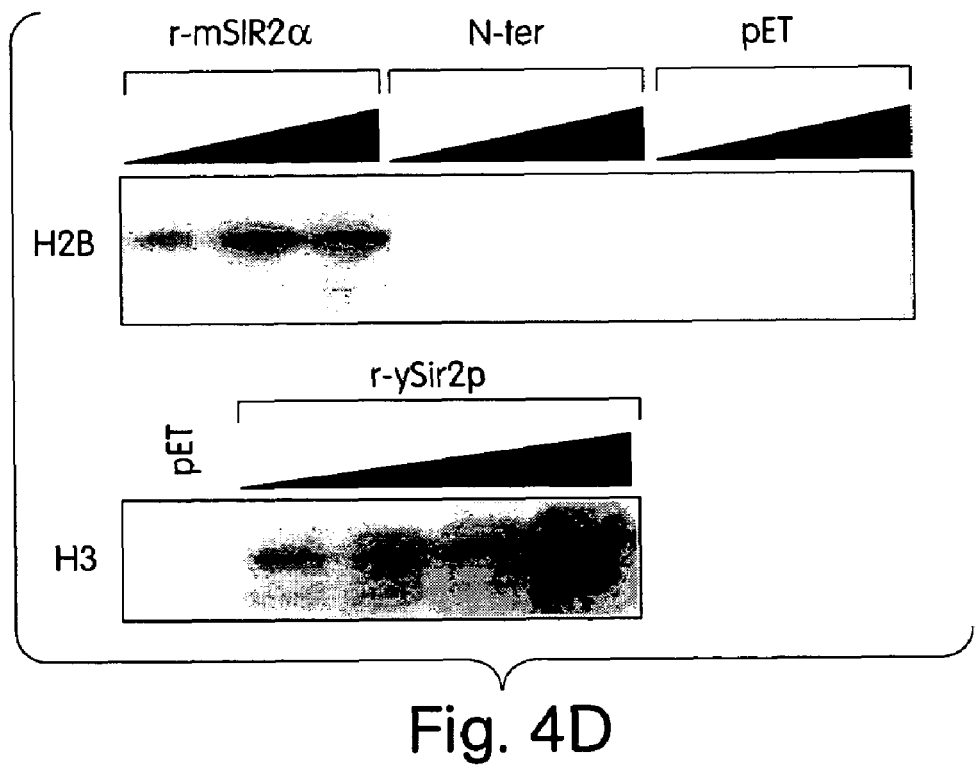
FIG. 4D illustrates the dose-dependent modification of H2B and H3 by recombinant yeast r-ySir2p and murine r-mSir2α proteins.
Figure 4E:
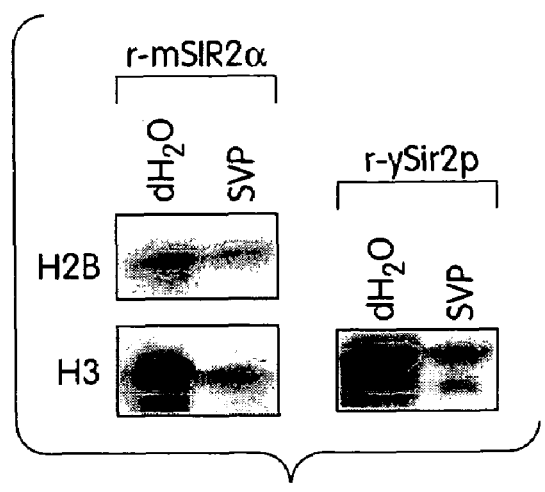
FIG. 4E illustrates the effects of snake venom phosphodiesterase (SVP) on the removal of radiolabeled $^{32}P$-NAD from Sir2-modified H2B and H3.
Figure 4F:
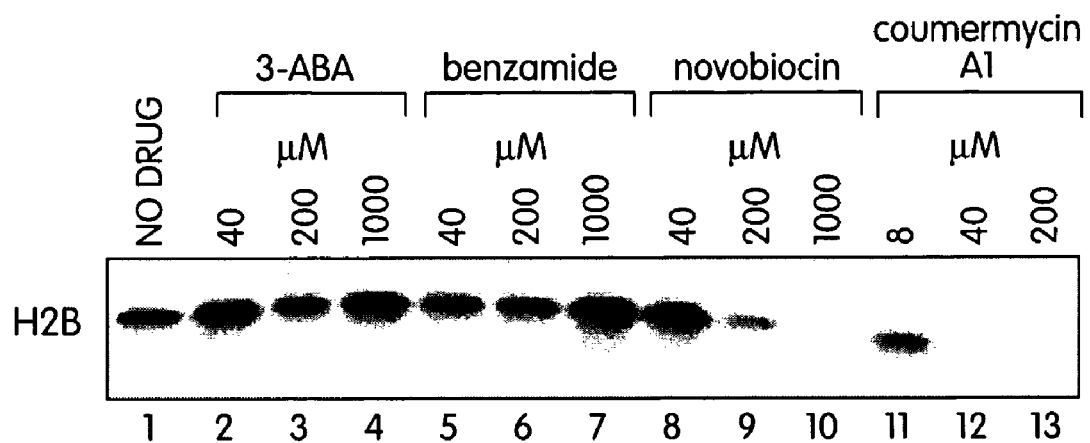
FIG. 4F depicts the effects of mono-ADP-ribosylation inhibitors (novobiocin and coumermycin A1), but not poly-ADP-ribosylation inhibitors (3-aminobenzamide (3-ABA) and benzamide), on mSir2α ADP-ribosylation of H2B.

To gain further evidence that this modification is due to ADP-ribose, the ySir2p- or mSir2α-modified H2B and H3 with snake venom phosphodiesterase (SVP) that can digest the phosphodiester bond in the ADP-ribose moiety (FIGS. 4C, E). The radiolabeled $P^{32}$ (P*) is located at a position and the phosphodiester bond between radiolabeled and nonlabeled phosphates can be digested by snake venom phosphodiesterase (SVP), resulting in the removal of the radiolabel from ADP-ribosylated proteins (FIG. 4E). The radiolabel could be substantially removed from H2B and H3 by SVP (FIG. 4E). The label remaining in the histones may be due to the forward reaction by Sir2 enzymes and NAD during this treatment.

Histone products of Sir2 modification of unique molecular weights were observed in this assay, suggesting that this modification may not be poly-ADP-ribosylation, but mono-ADP-ribosylation. The sensitivity of the ADP-ribosylase activity of mSir2α to poly ADP-ribosylation inhibitors (3-aminobenzamide and benzamide) and mono-ADP-ribosylation inhibitors (novobiocin and coumermycin A1) was evaluated. (FIG. 4F). 3-aminobenzamide and benzamide did not inhibit the ADP-ribosylation activity of the mSir2α protein at concentrations of 40, 200 and 1000 μM (FIG. 4F, lanes 2 to 7) whereas novobiocin and coumermycin A1 strongly inhibited ADP-ribosylation at concentrations of 200 μM and 40 μM, respectively (FIG. 4F, lanes 9 and 12), consistent with their reported $IC_{50}$ concentrations of 370 and 27 μM. ySir2p showed the same sensitivity to those inhibitors (data not shown). Therefore, the sensitivity of the Sir2 enzymatic activities to those inhibitors demonstrates that these proteins are of the mono-ADP-ribosyltansferase class.

Figure 4G:
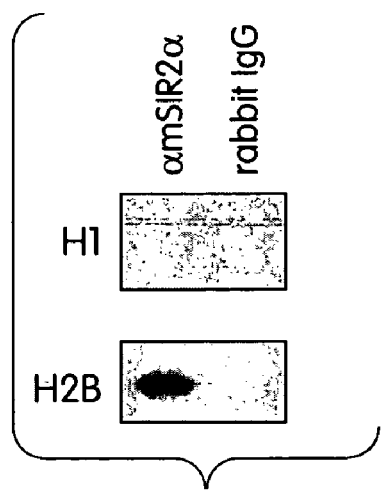
FIG. 4G depicts the mono-ADP-ribosyltransferase activity of mSir2α immunoprecipitated by an antiserum to mSir2α (αmSir2α) from NIH3T3 whole cell extracts.

ADP-ribosyl-transferase activity could be detected for the endogenous mSir2α immunoprecipitated from NIH3T3 whole cell extracts (FIG. 4G). The endogenous mSir2α was immunoprecipitated from 300 μg of the NIH3T3 whole cell extract with an anti-mSir2α polyclonal antibody and the immune complex on Protein A-Sepharose beads was incubated in the reaction buffer containing $^{32}$P-labeled NAD and histone H1 or H2B.

ADP-Ribosyltransferase and NAD Hydrolase Activities of Yeast and Mouse Sir2 are Specifically Triggered by Acetylated H3 and H4 N-Terminal Tail Peptides Extended N-terminal tails of H3 and H4 are known to be important for the formation of Sir complex-mediated heterochromatin structure in yeast (Hecht, A., et al., *Cell* 80: 583-592 (1995)) and are targets for several different types of histone modification, such as acetylation, phosphorylation, and methylation (Hansen, J. C., et al., *Biochemistry* 37: 17637-17641 (1998)). The residues 1-20 of H3 are conserved through evolution and lysines 9 and 14 which are acetylated in the diacetylated peptide are indicated by asterisks in FIG. 5A. The residues 1-20 of monoacetylated H4 peptide originate from the human sequence and acetylated residues are indicated by asterisks FIG. 5A. Tetra-acetylated H4 peptide corresponds to the Tetrahymena sequence where all lysines are acetylated. The N-terminal tails of histones were evaluated as targets for ADP-ribosylation by Sir2 proteins.

Figures 5A, 5B:
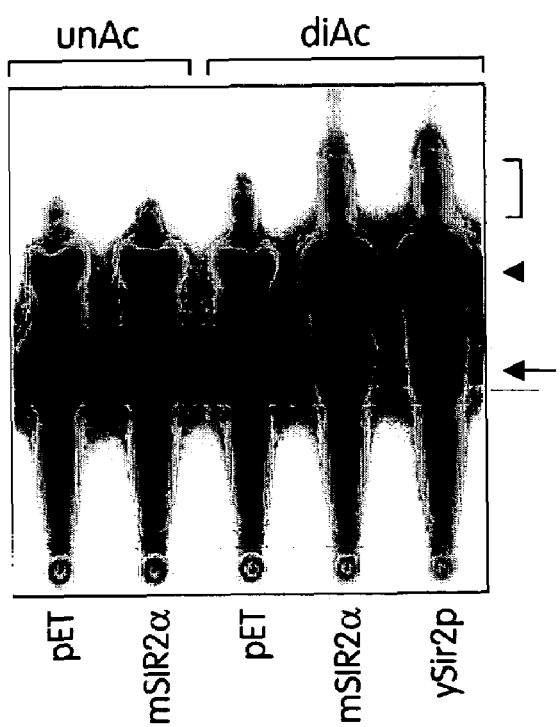
FIG. 5A depicts the amino acid sequences of the N-terminal tails of H3 (SEQ ID NO: 6) and H4 (mono AC, SEQ ID NO: 7, tetra Ac, SEQ ID NO: 8) peptides. The asterisks depict the site of acetylation (mono Ac, tetra Ac) to generate peptides with and without acetylated lysines. Human H3 GenBank Accession No: M26150, mouse H3 GenBank Accession Nos: M23459, 32460, 32461, 32462. Human H4 GenBank Accession Nos: M60749, M16707, mouse H4 GenBank Accession No: U62672.
FIG. 5B depicts the effects of mSir2α and ySir2p on diacetylated H3 peptide (diAc), but not unacetylated H3 (unAc). A bracket, an arrowhead, and an arrow at right indicate modified peptides, hydrolyzed and/or decomposed products of $^{32}P$-NAD, and unhydrolyzed $^{32}P$-NAD, respectively.

Two synthetic peptides corresponding to the first 20 amino acids of H3 either unacetylated or diacetylated (on lysines 9 and 14) (FIG. 5A) were evaluated to determine whether yeast and mouse Sir2 proteins could modify these peptides. Reactions were carried out as above and analyzed by thin layer chromatography. Both the yeast and mouse Sir2 modified only the diacetylated H3 tail peptide (FIG. 5B). The indicated spot (bracket, FIG. 5B) was identified as the modified peptide because it migrated just below the ninhydrin-positive peptide spot on the chromatogram. Further, NAD hydrolase activity of both ySir2p and mSir2α was stimulated in the presence of the diacetylated peptide, indicated by the arrowhead in FIG. 5B. Since Lys9 and Lys14 of H3 are acetylated in vivo, this preferential utilization of the acetylated H3 peptide strongly suggests that the tail of H3 is a biologically relevant substrate for Sir2 proteins.

Figure 5C:
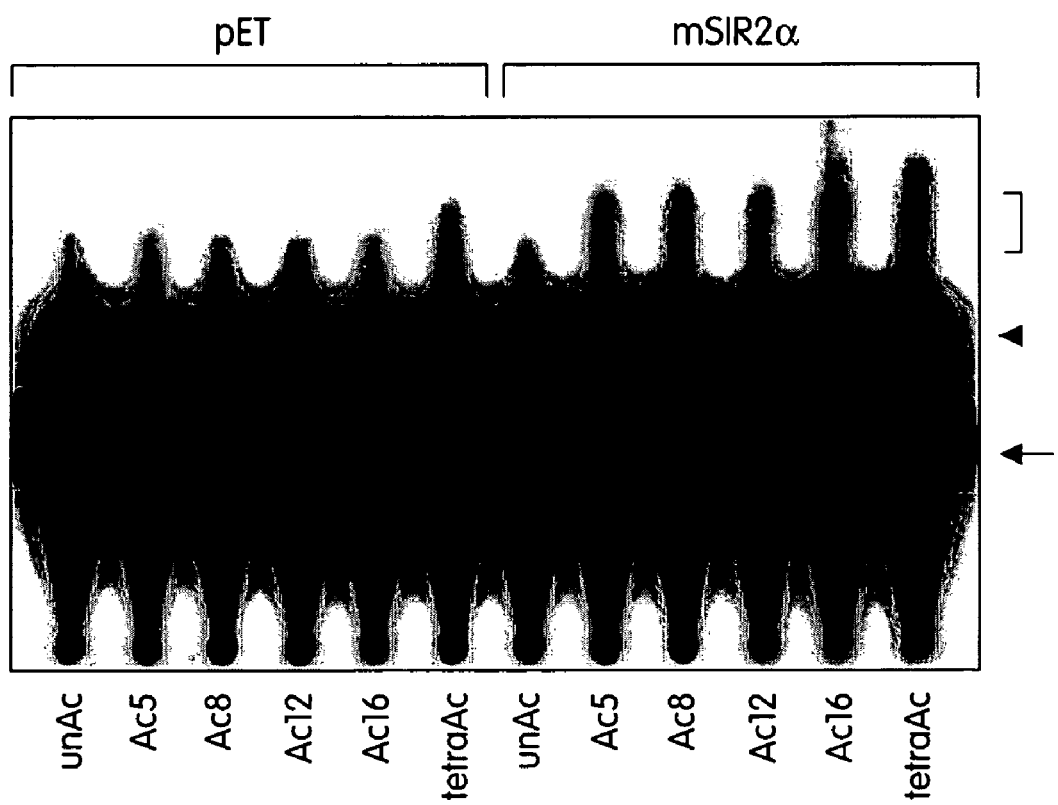
FIG. 5C illustrates mSir2α modification of Lys16-acetylated H4 peptide (Ac16). Unacetylated (unAc), monoacetylated (Ac5, Ac8, Ac12, or Ac16), and tetraacetylated (tetraAc) peptides were added in the reactions with the control eluate (pET) or the mSir2α, respectively.

The extended N-terminal tail of histone H4 has four lysines at positions 5, 8, 12, and 16. (FIG. 5A). Mutational studies show the importance of these residues in silencing in vivo, and Lys5, 8, and 16 are hypoacetylated in yeast chromatin at HM loci. In mammalian cells, Lys16 of H4 is highly acetylated. H4 peptides (residues 1-20), which were acetylated singly at each of these lysines (5, 8, 12 or 16), were synthesized and evaluated for mSir2α stimulated ADP-ribosyltransferase and NAD hydrolase activities (FIG. 5C). A striking specificity in the acetylation pattern of the H4 tail was required to stimulate Sir2 activity. Both ADP-ribosylation and NAD hydrolysis were stimulated by the Lys16Ac peptide, but were affected weakly by the Lys5-, 8-, 12-, and tetra-acetylated peptides (FIG. 5C).

Highly Conserved Amino Acid Residues in the Core Domain are Essential for the Mono-ADP-Ribosylation Activity of mSir2α

To analyze the mono-ADP-ribosylation activity more precisely, ten highly conserved amino acid residues in the core domain of mSir2α were changed to alanine (FIG. 6A), mutant recombinant Sir2 proteins produced E. coli, and evaluated for ADP-ribosylation activities on H2B and H3 in vitro. Protocols for the production of mutant nucleic acid constructs and proteins are well known to the skilled artisan. (See, for example, Ausubel et al., "Current Protocols in Molecular Biology", John Wiley & Sons, NY, N.Y. (1999)).

Figures 6A, 6B:
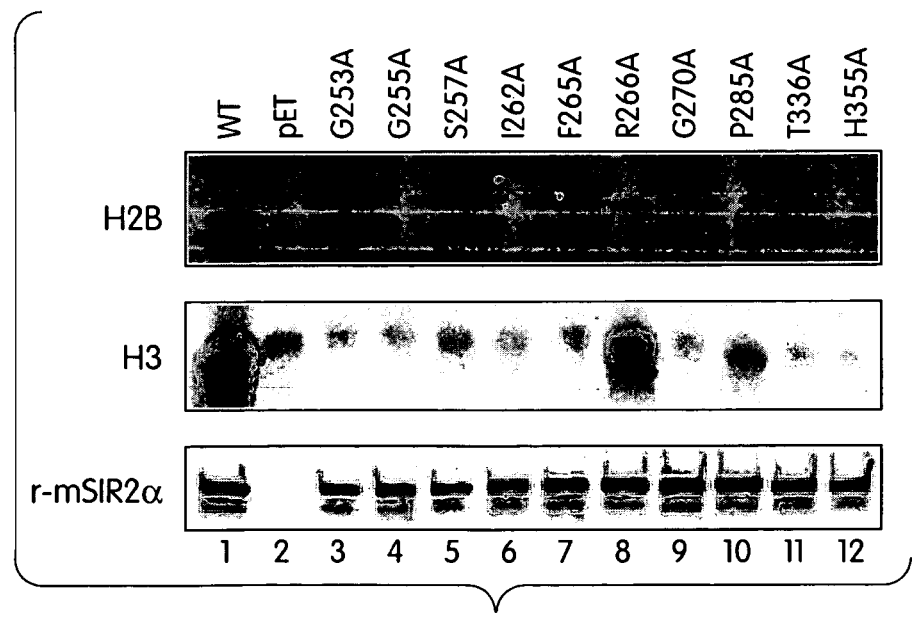
FIG. 6A depicts the highly conserved amino acid residues in the core domain of mSir2α (SEQ ID NO: 9) and ySir2 (SEQ ID NO: 10) proteins. Identical amino acids are boxed. Arrowheads depict the amino acid residues used to generate mutant Sir2 proteins which were evaluated for ADP-ribosylation activity.
FIG. 6B depicts the ADP-ribosylation activities of mSir2α proteins (Wildtype, WT; vector alone, pET; mutants G253A, G255A, S257A, I262A, F265A, R266A, G270A, P285A, T336A, H355A) on histones H2B and H3.

Aliquots of recombinant protein (10 µg) of the wild type recombinant mSir2α (WT), the pET control pET, and the mutant proteins (G253A, G255A, S257A, I262A, F265A, R266A, G270A, P285A, T336A, H355A) were incubated with H2B or H3. Western blot analysis showed that the amount of each full-length protein used was comparable (FIG. 5B, r-mSirα). All of the mutations of highly conserved residues dramatically affected the mono-ADP-ribosylation activity of mSir2α (FIG. 6B). The results were similar using H2B or H3.

Figure 6C:
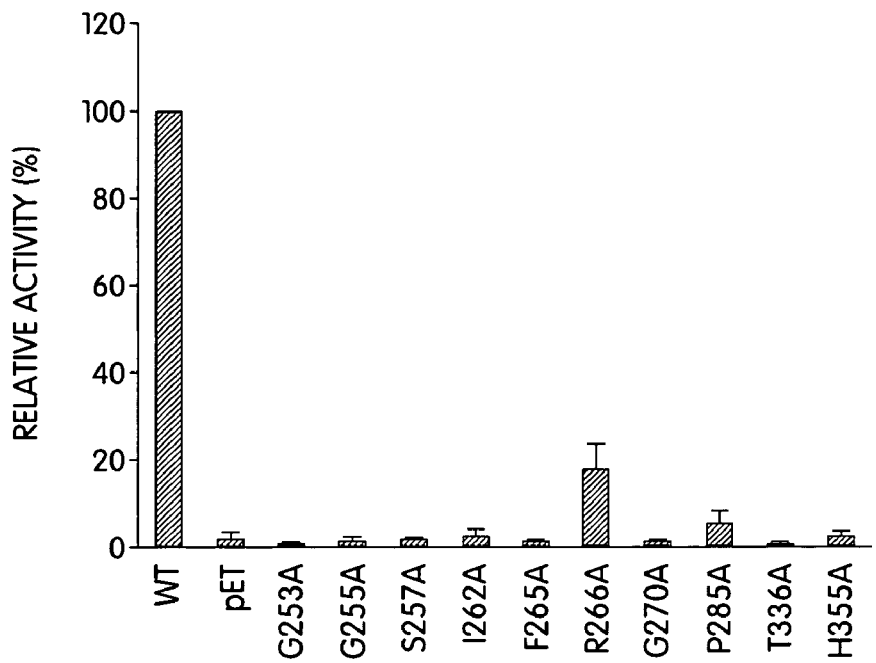
FIG. 6C illustrates the quantitation of the ADP-ribosylation activities of the mSir2α mutants (G253A, G255A, S257A, I262A, F265A, R266A, G270A, P285A, T336A, H355A) compared to wild type (WT) and control pET.

Eight mutants (G253A, G255A, S257A, I262A, F265A, G270A, T336A, H355A) completely abolished the activity and the two mutants R266A and P285A showed some residual activities compared to the wild type activity (18% for R266A and 5% for P285A, see FIG. 6C). The radioactivity of H2B modified by the wild type is assigned to 100% and other data were normalized according to the wild type activity and blots quantitated by Phosphorimaging. The averages and the standard deviations were calculated from two independent experiments. In the core domain of ySir2p, mutations on highly conserved residues also affected the mono-ADP-ribosylation activity. Therefore, the core domain of Sir2 proteins contain the catalytic activity of mono-ADP-ribosylation and the evolutionarily conserved residues in the core domain are essential for this activity.

The mSir2α Core Domain Conveys Transcriptional Repressive Activity in Mouse Cells The in vivo function of the mSir2α mono-ADP-ribosylation activity, was evaluated by constructing expression vectors of wild-type (WT) and each of the mutant core domains (G253A, G255A, S257A, I262A, F265A, R266A, G270A, P285A, T336A, H355A) fused to the yeast Gal4 DNA binding domain (DBD) and transfecting the constructed NIH3T3 cells with a luciferase reporter plasmid containing four upstream Gal4 binding sites.

Figure 6D:
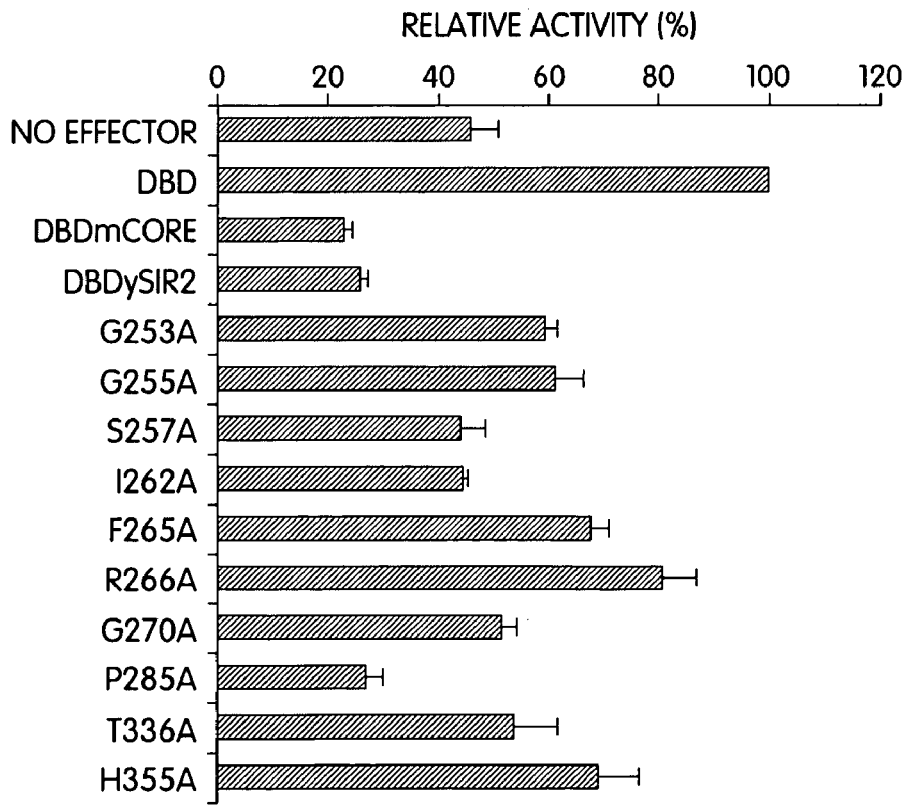
FIG. 6D illustrates the in vivo transcriptional repression by the mSir2α wildtype and mutant core domain fused to the GAL4 DNA binding domain (DBD).

NIH3T3 cells $10^6$ were transfected with 4 µg of effector plasmids which fuse Sir2 sequences to the DBD, 1 µg of a reporter plasmid with luciferase expression driven by GAL4 DNA-binding sites and 1.5 µg of SV40 promoter-driven β-galactosidase gene to normalize the transfection efficiency. All luciferase activities after normalization were standardized to DBD alone. The averages and the standard deviations were calculated from three independent transfection experiments. The wild-type core domain was able to repress transcription four-fold, compared to the activity of the DBD only, which is known to activate transcription approximately two-fold in mammalian cells (FIG. 6D). The DBD-fused full-length ySir2p also showed similar repressive activity in NIH3T3 cells, suggesting that the shared mono-ADP-ribosylation activity can be involved in transcriptional repressive activity. All of the core domain mutants except for P285A reduced transcriptional repressive activity (FIG. 6D). One explanation for this discrepancy is that the P285A change does not inhibit the catalytic domain but causes the recombinant protein to be misfolded in E. coli. Another protein that binds to mSir2α can rescue such a mutant in mammalian cells.

Sir2p is an NAD-Dependent Deacetylase for Histone H3

Figure 8A:
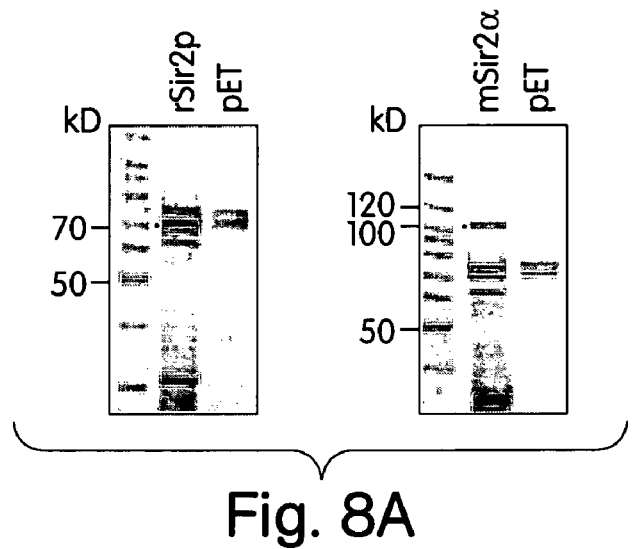
FIGS. 8a, 8b, 8c, 8d, 8e, 8f, and 8g illustrate the in vitro deacetylation of the H3 peptide (residues 1-20) di-acetylated at lysines 9 and 14 by recombinant yeast Sir2p.

The experiments employed purified recombinant Sir2p in a reaction with NAD and a peptide of the histone H3 amino-terminal tail (residues 1-20) di-acetylated at lysines 9 and 14. These lysines are hypoacetylated in silenced chromatin and mutations at these positions to glycine greatly reduce silencing in vivo (Thompson, J. S., et al., Nature 369: 245-247 (1994)). The products of a reaction containing 5 µg of recombinant yeast Sir2p (79 pmoles) (FIG. 8a), 10 µg of the H3 peptide (4.2 nmoles) increasing concentrations of NAD were analyzed s by high pressure liquid chromatography (HPLC).

Figure 8B:
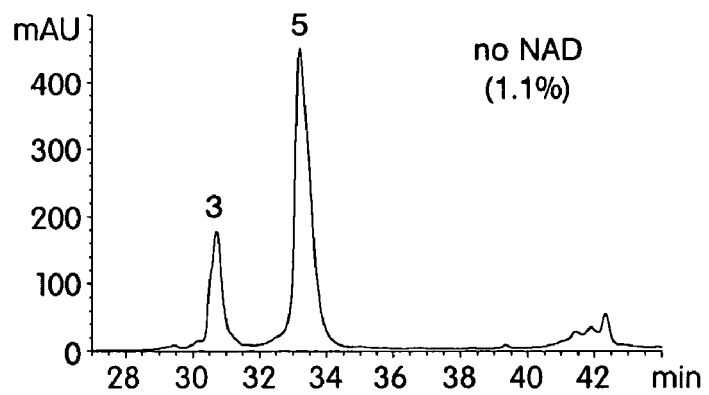
Figure 8C:
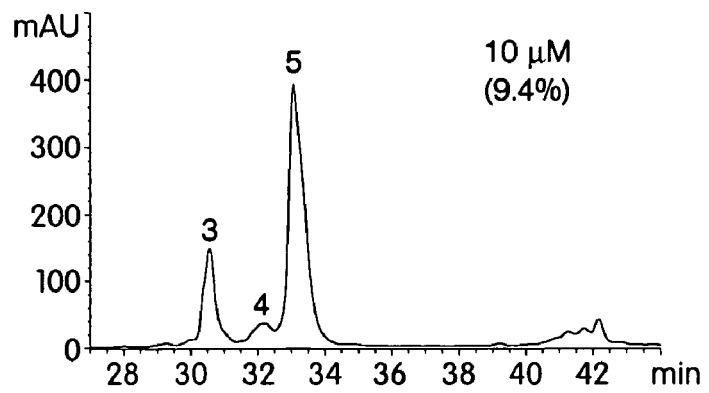
Figure 8D:
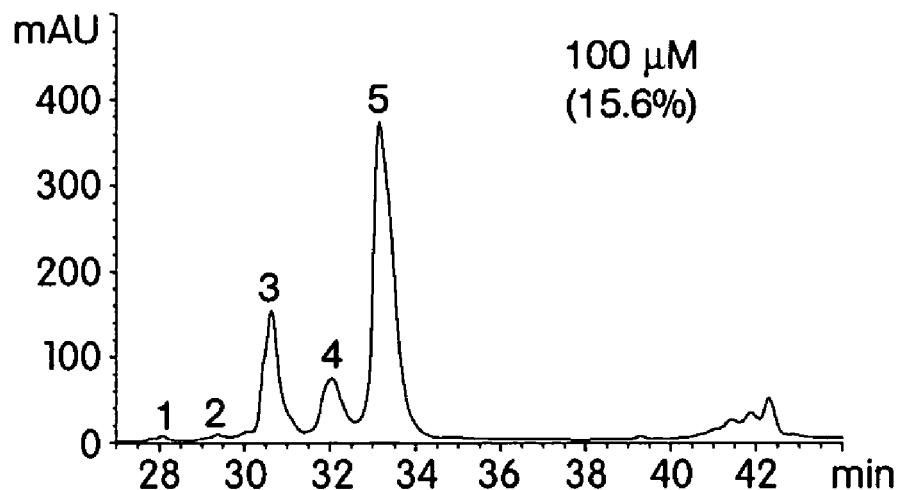
Figure 8E:
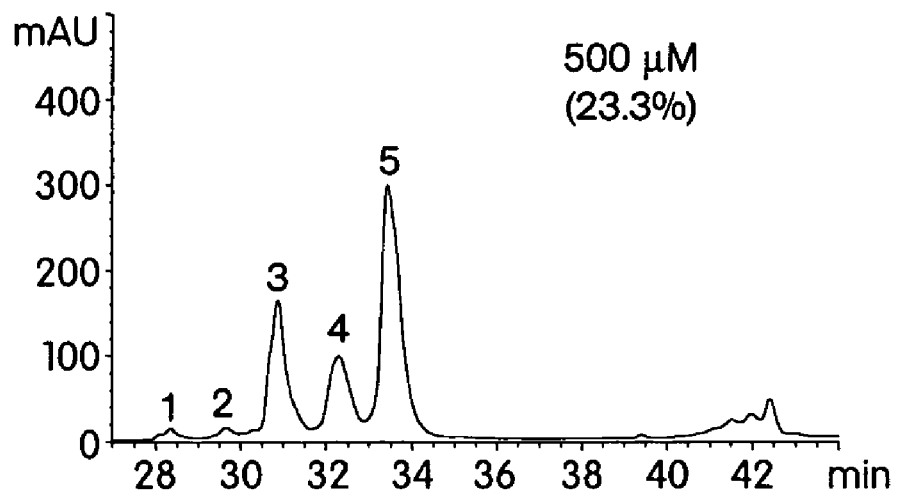
Figure 8F:
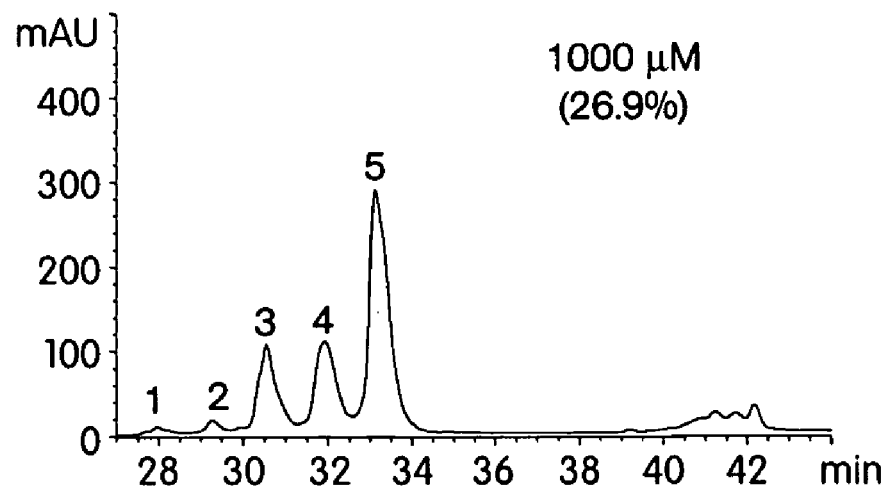
Figure 9A:
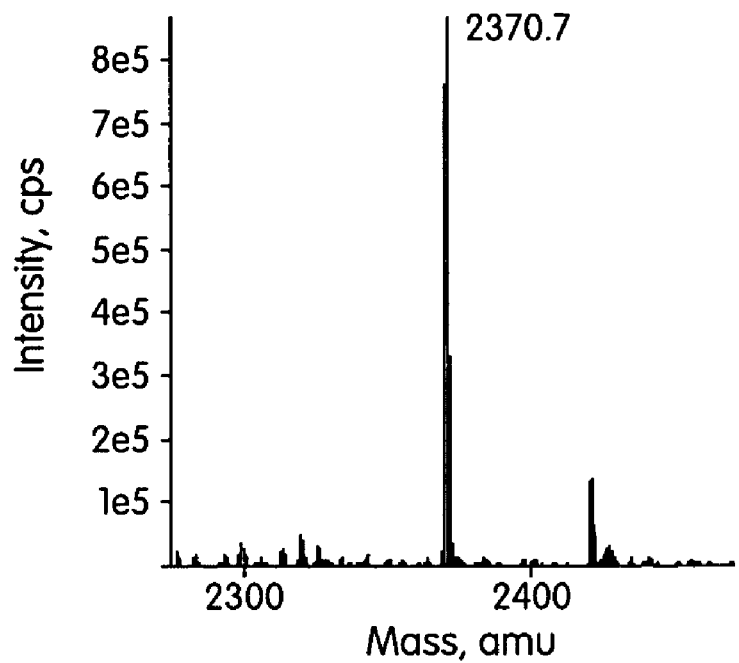
FIGS. 9a, 9b, 9c and 9d are electron-spray mass spectroscopy of peaks 3-5 of HPLC chromatogram.

As shown in FIG. 8b, the histone peptide reacted in the absence of NAD gave rise to two peaks (3 and 5) which were analyzed by electron-spray mass spectroscopy (FIGS. 9a and 9d) and correspond to monomer (MW2370) and dimer (MW4740) peptide, the latter likely due to oxidation of the peptide at the carboxyl cysteine residue. The same species were observed in reactions with a control bacterial preparation ("pET" in FIG. 8a) in the presence of NAD (not shown).

Figure 8G:
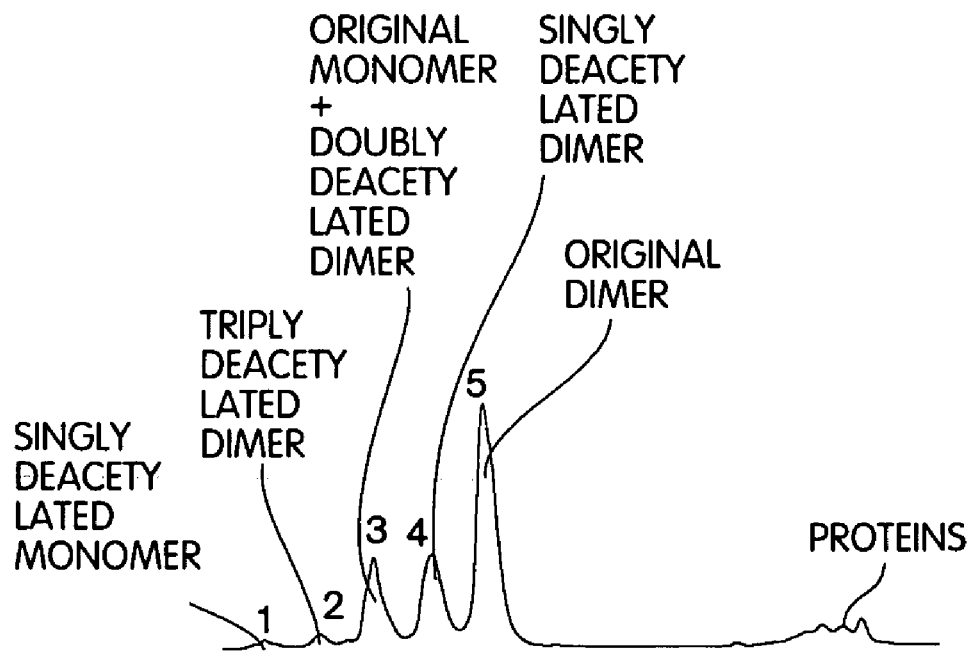
Figure 9B:
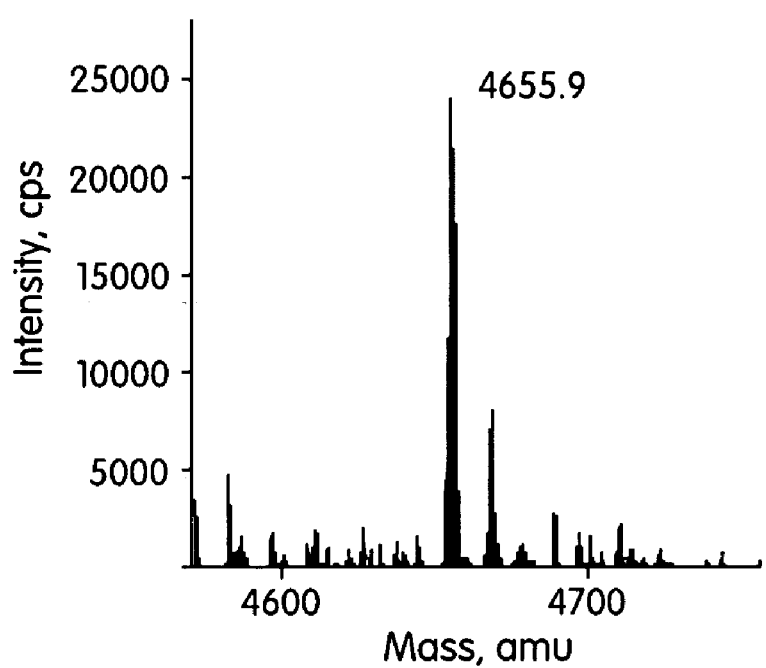
Figure 9C:
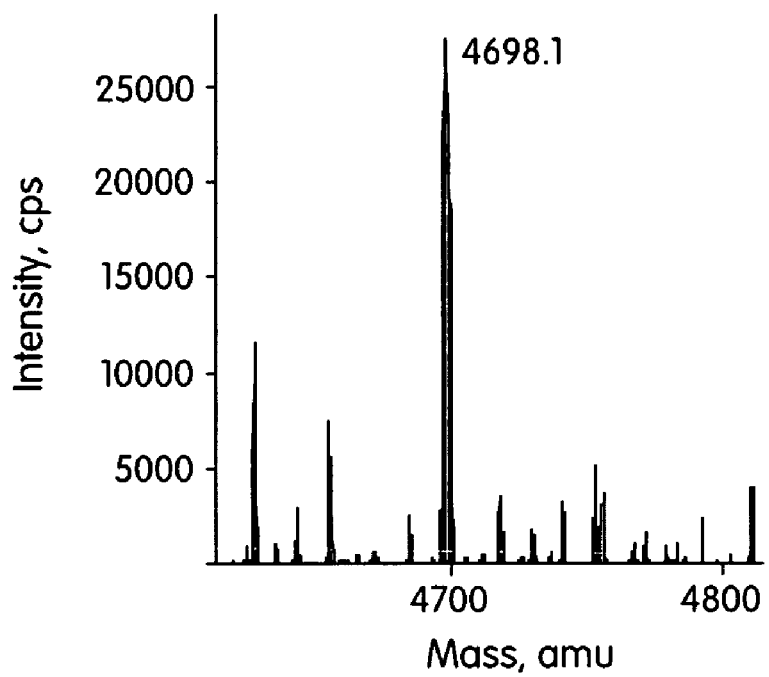
Figure 9D:
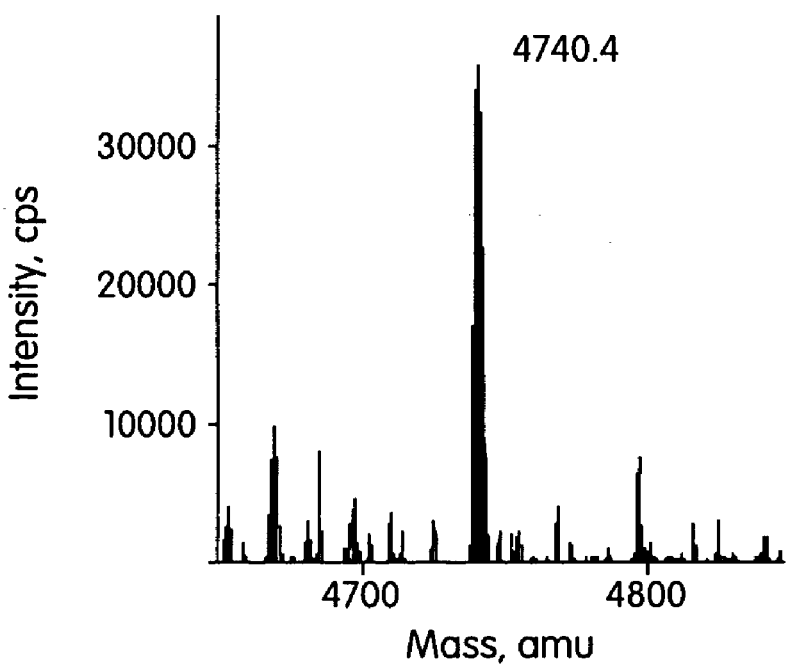
Figure 10A:
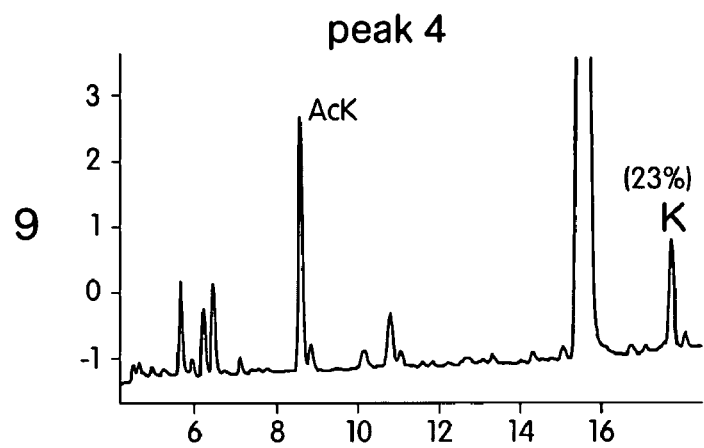
FIGS. 10a, 10b, 10c, 10d, 10e and 10f are the amino-terminal sequencing of peaks 4 and 5 of the deacetylase reaction at 1 mM NAD. Peaks 4 and 5 were subjected to sequencing by Edmann degradation. Chromatograms at positions 9, 14, and 18 are shown. In peak 4, about 23% of Lys9 (FIG. 10a) and 27% of Lys 14 (FIG. 10b) were deacetylated. In peak 5, both Lys 9 and 14 are essentially all acetylated (FIG. 10d and FIG. 10e). The unacetylated Lys18 of both peaks 4 and 5 are shown for comparison (FIG. 10c and FIG. 10f). The peak to the right of the acetylated lysine at position 14 corresponds to alanine, which is a preview of Ala 15.
Figure 10B:
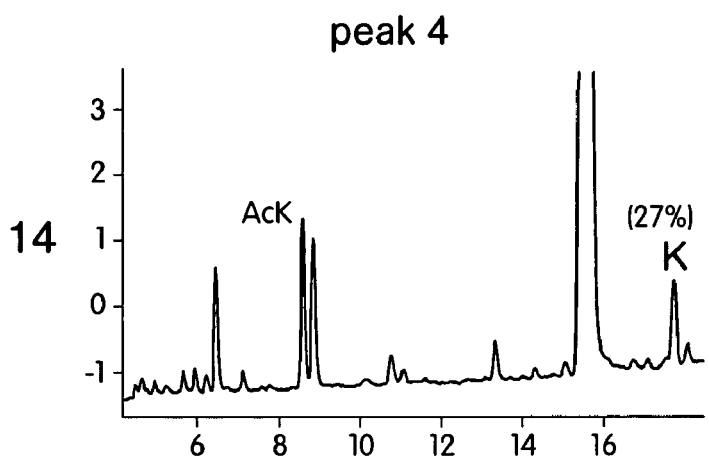
Figure 10C:
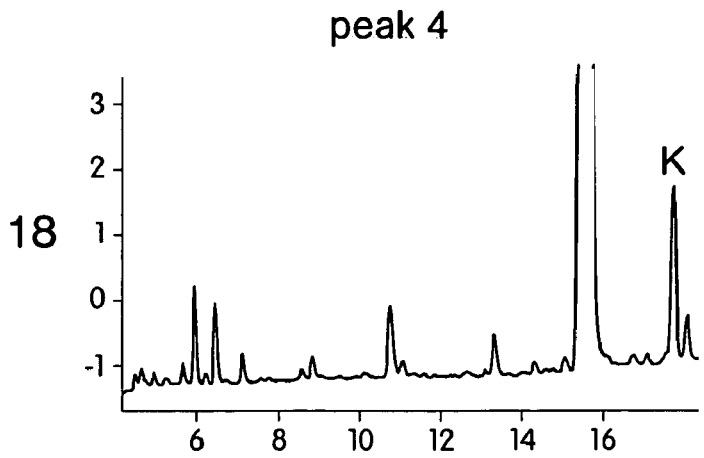
Figure 10D:
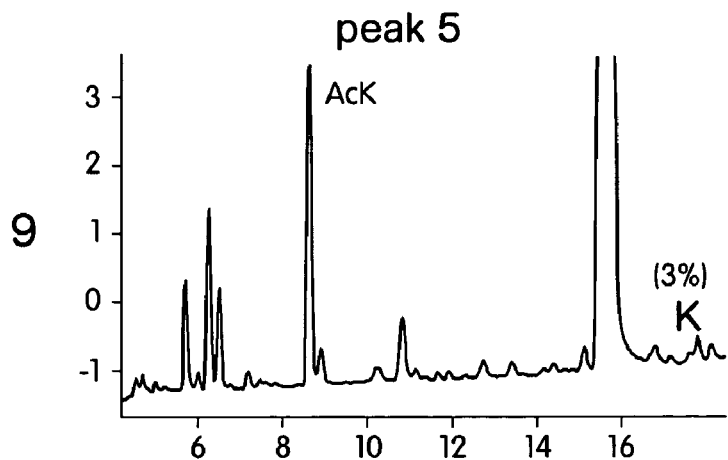
Figure 10E:
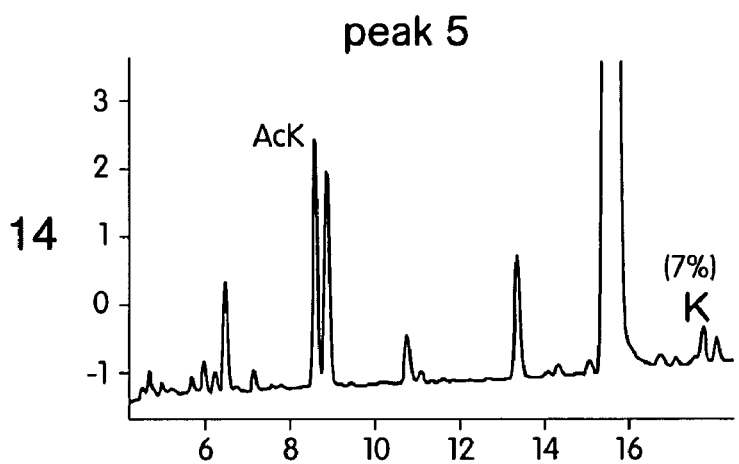
Figure 10F:
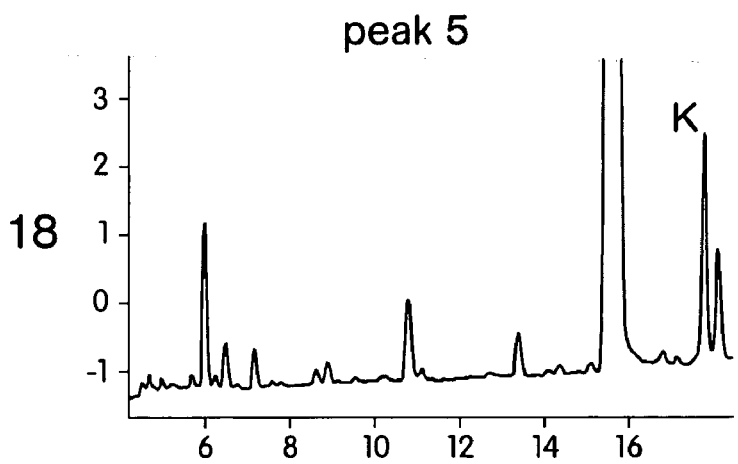

The addition of NAD to the reaction containing Sir2p gave rise to three additional peaks (1, 2, and 4), as well as an alteration in peak 3 (FIGS. 8c, 8d, 8e and 8f), which were also analyzed by electron-spray mass spectroscopy. Strikingly, these peaks did not correspond to ADP-ribosylated species, but rather to deacetylated species of peptide (see FIG. 8g). Peak 4 corresponded to the singly-deacetylated dimer (MW 4698) (FIG. 9c), peak 3 now also contained the doubly-deacetylated dimer (MW4656) (FIG. 9b). Because of their lower abundance, peak 1 and peak 2 were analyzed separately by matrix assisted laser desorption/ionization (MALDI) mass spectroscopy and peak 2 was found to correspond to the triply deacetylated dimer (MW4614) and peak 1 to the singly-deacetylated monomer (MW2328) (not shown). The relative areas under peaks 1, 2, and 4 was quantitated and at least 27% of the input peptide was deacetylated by Sir2p. The approximate Km of this deacetylation reaction for NAD was about 100 μM, at which the reaction proceeded to about 50% of the maximal level observed at higher concentrations of the cofactor.

To analyze these reaction products further, peak 4, the singly deacetylated dimer, along with the input peak 5 were subjected to N-terminal protein sequencing by Edmann degradation (FIG. 10). The only differences between the input and reacted peaks occurred at lysines 9 and 14. Approximately 23-27% of the acetyl lysines at each position were deacetylated by Sir2p in the presence of NAD, in agreement with the calculated efficiency of the reaction and the mass spectroscopy data above. The unacetylated lysine 18 of peaks 4 and 5 is also shown for comparison. Thus, Sir2p is an NAD-dependent histone deacetylase which can deacetylate either lysine 9 or 14 of the H3 N-terminus.

Effects of Inhibitors on Deacetylation and Putative ADP-Ribosylation

Figure 11A:
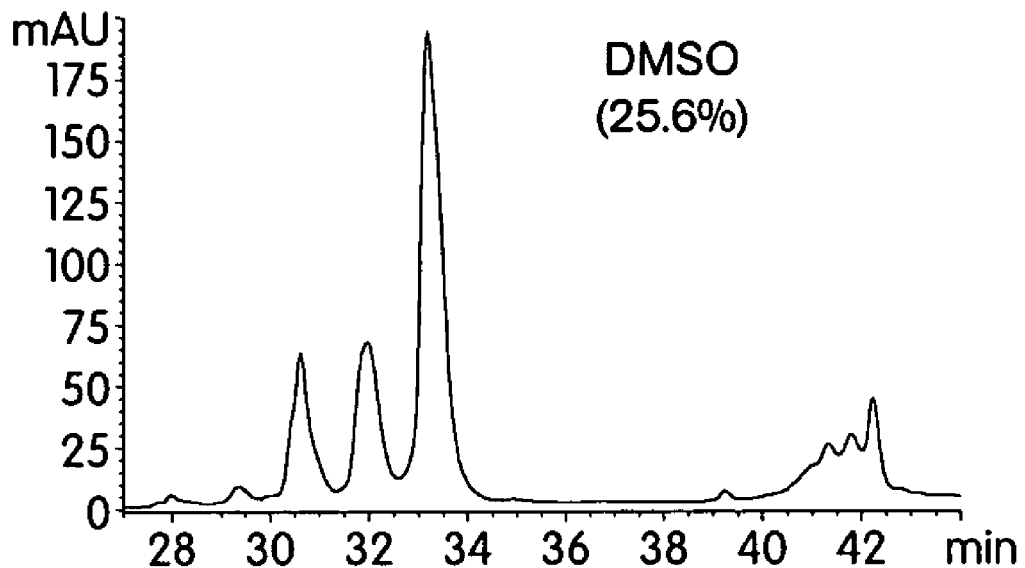
FIGS. 11a, 11b, 11c, 11d and 11e illustrate the effects of inhibitors on the deacetylase and putative ADP-ribosyltransferase activities of recombinant Sir2p (rSir2p). The HPLC chromatograms of the reactions in the presence of solvent only (FIG. 11a), 400 nM TSA (FIG. 11b) and 200 μM coumermycin A1 (Coumer) (FIG. 11e) are shown. The calculated efficiencies of the reactions are indicated. The effect of 200M coumermycin A1 on ADP-ribosylation of the intact histone H3 (FIG. 11c) and the H3 peptide (FIG. 11d) are examined on SDS-PAGE and TLC, respectively. pET corresponds to the vector control.
Figure 11B:
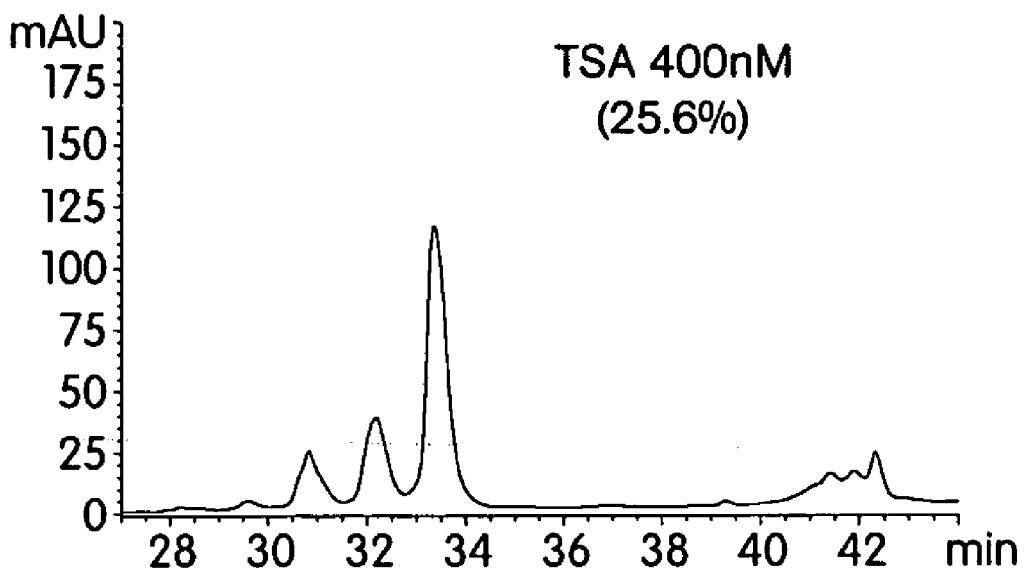

The effects of a potent inhibitor of histone deacetylases, trichostatin A (TSA) (Yoshida, M., et al., A. J. Biol. Chem. 265: 17174-17179 (1990)) was evaluated. TSA has been shown to act on constitutive heterochromatin in vivo, since it disrupts centromeric heterochromatin in S. pombe (Ekwall, K., et al., Cell 91: 1021-1032 (1997)). As shown in FIGS. 11a and 11b, TSA was totally incapable of inhibiting deacetylation, indicating that Sir2p is fundamentally different from the class of TSA-sensitive histone deacetylases, including Rpd3 (Taunton, J., et al., Science 272: 408-411 (1996)).

Figure 11C:
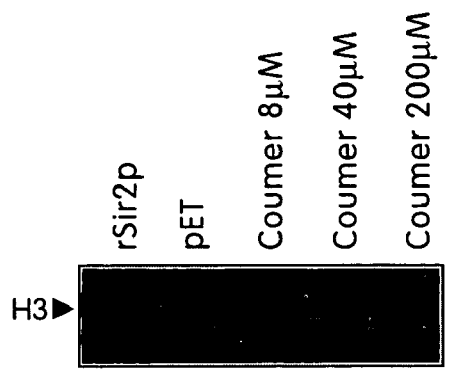
Figure 11D:
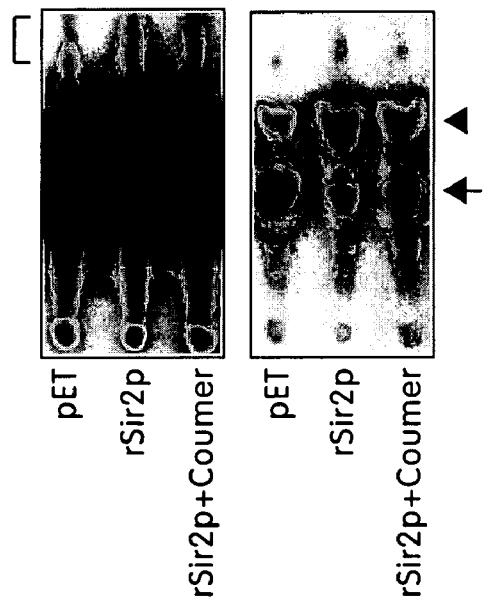

Sir2 proteins have been proposed to transfer a single ADP-ribose from NAD to protein (Frye, R. A., Biochem. Biophys. Res. Commun. 260: 273-279 (1999)). Consistent with this, we found that $^{32}$P was transferred from NAD to intact histone H3 (FIG. 11c) or to the H3 peptide (FIG. 11d). Transfer of label to the peptide was assayed using thin layer chromatography (TLC), which revealed not only this transfer but a substantial amount of NAD hydrolysis.

Figure 11E:
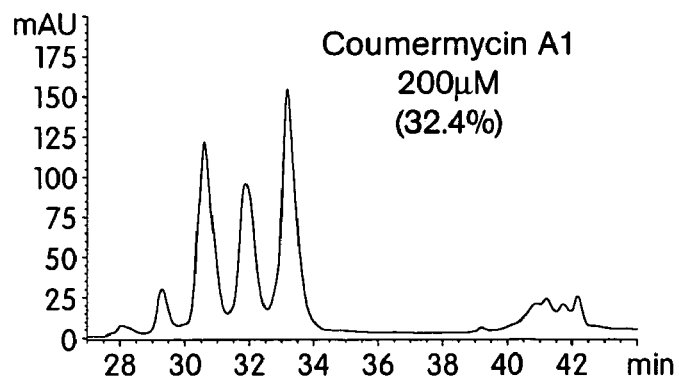

The effects of a known inhibitor of mono-ADP-ribosyltransferases, coumermycin A1 (Banasik, M., et al., Mol. Cell. Biochem. 138: 185-187 (1994)) was evaluated. Both ADP-ribosylation (FIGS. 11c and 11d) and NAD hydrolysis (FIG. 11d) were inhibited by this drug at concentrations known to inhibit other mono-ADP-ribosyltransferases. Strikingly, coumermycin A1 was not capable of inhibiting deacetylation of the H3 tail by Sir2p (FIG. 11e). Thus, the ADP-ribosyltransferase and NAD hydrolase reactions are fundamentally distinct from this NAD-dependent deacetylation reaction. These two separable enzymatic activities of Sir2p may play distinct roles in vivo.

Mouse Sir2p Also Catalyzes the Deacetylation of the Histone H3 Tail

Figure 12B:
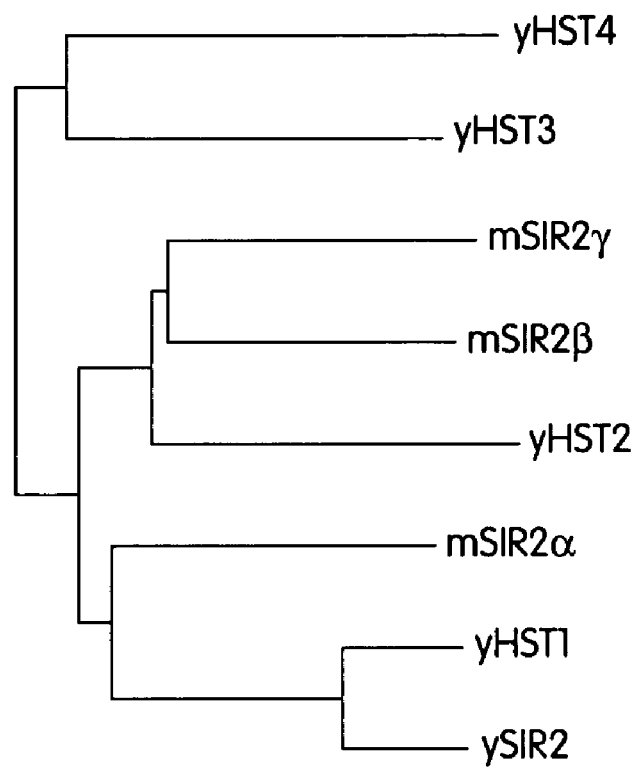
Figure 12C:
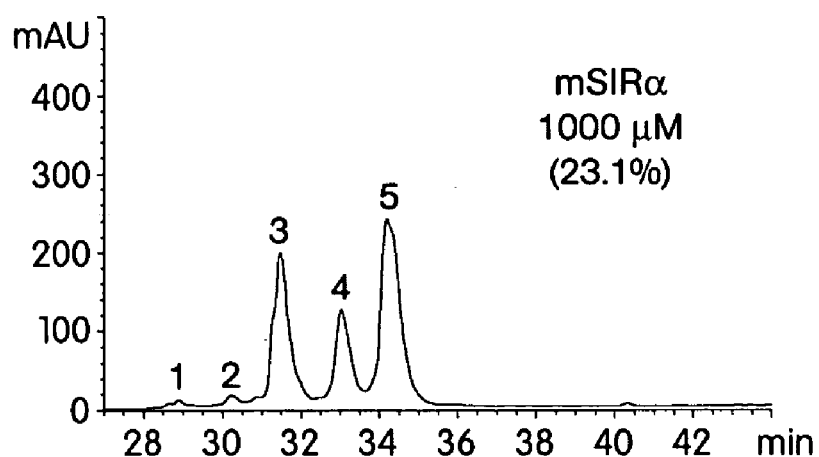
Figure 13A:
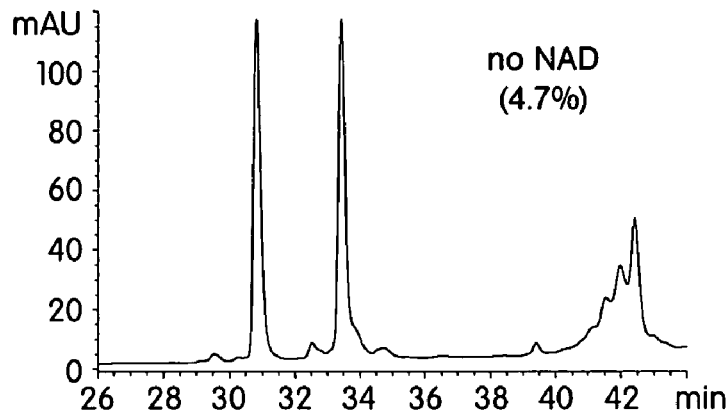
FIGS. 13a, 13b, 13c, 13d and 13e illustrate the effects of NAD derivatives on the Sir2p deacetylation activity of the H3 peptide. The HPLC chromatograms of the reactions with no NAD derivatives (FIG. 13a) and 1 mM concentration of NAD (FIG. 13b), NADH (FIG. 13c), NADP (FIG. 13d), and NADPH (FIG. 13e) are shown. The calculated efficiencies of the reactions are also indicated.
Figure 13B:
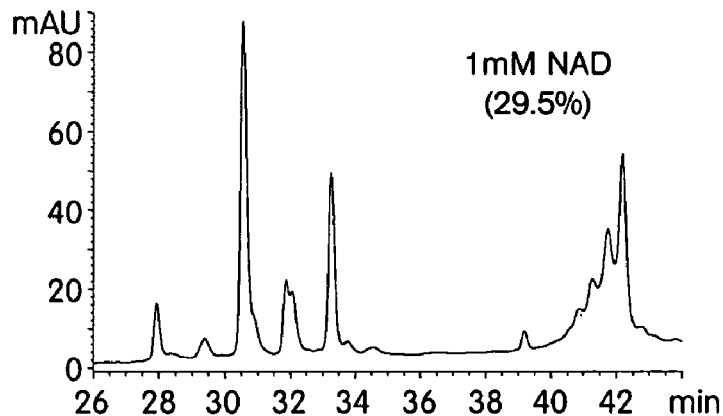
Figure 13C:
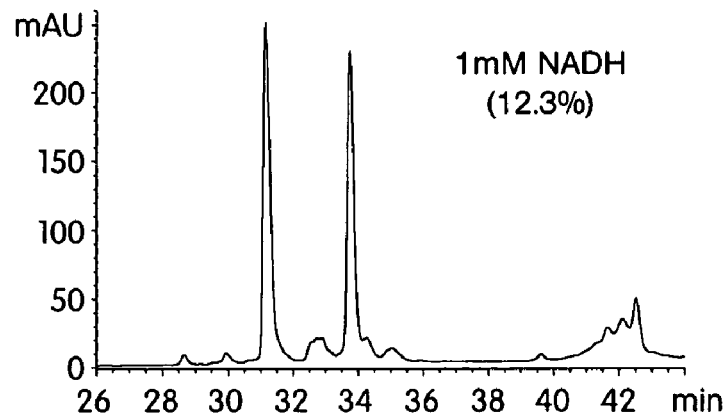
Figure 13D:
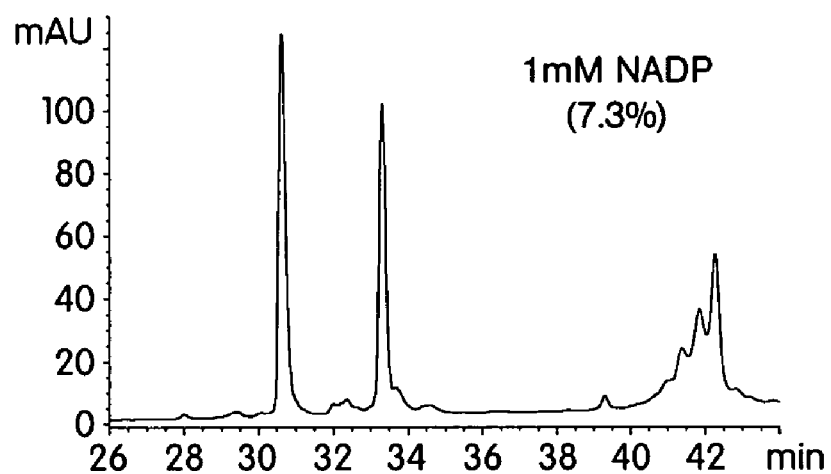
Figure 13E:
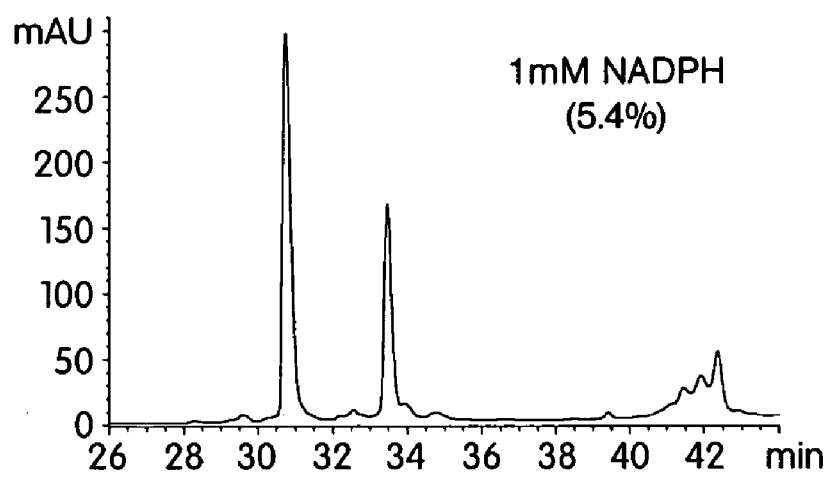
Figure 14B:
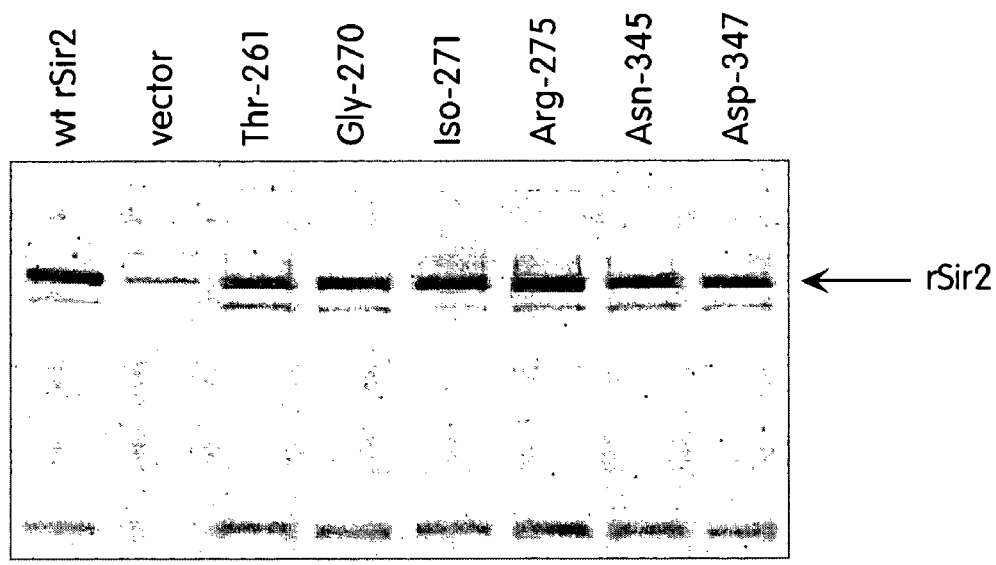
Figure 14C:
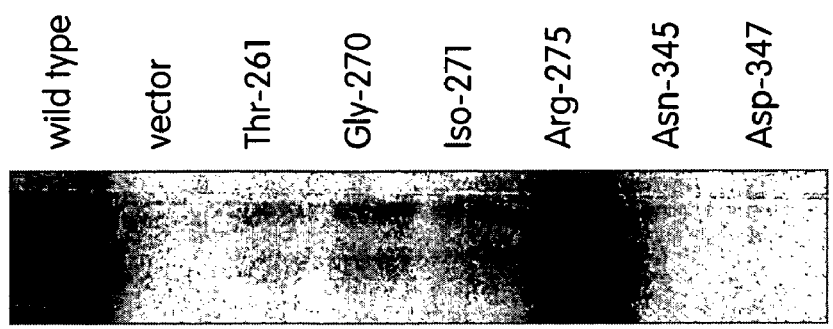
Figure 15A:
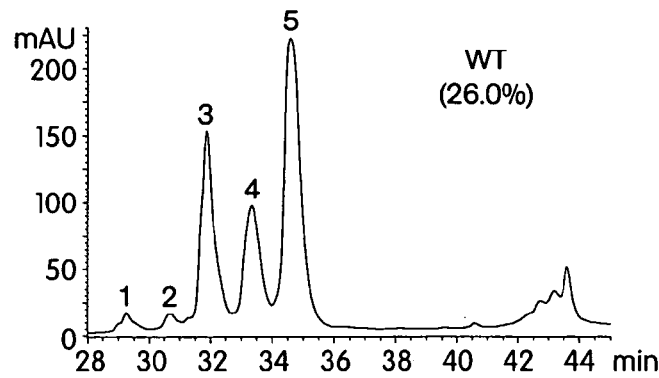
FIGS. 15a, 15b, 15c, 15d, 15e, 15f, 15g and 15h illustrate the effects of mutations in ySir2p on NAD dependent deacetylation of H3. The peptides were run on HPLC and the chromatograms based on the absorption at 220 nm recorded. The efficiency of reactions were determined by summing the area under the appropriate peaks.
Figure 15B:
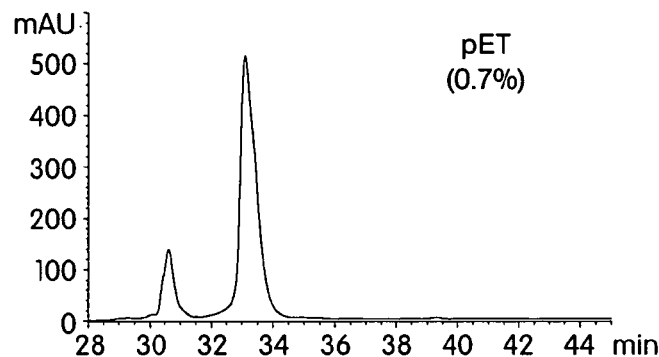
Figure 15C:
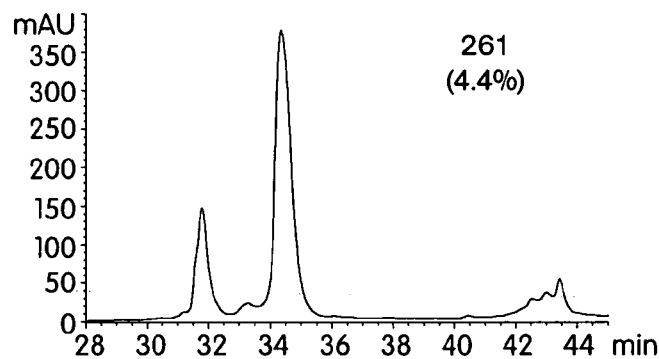
Figure 15D:
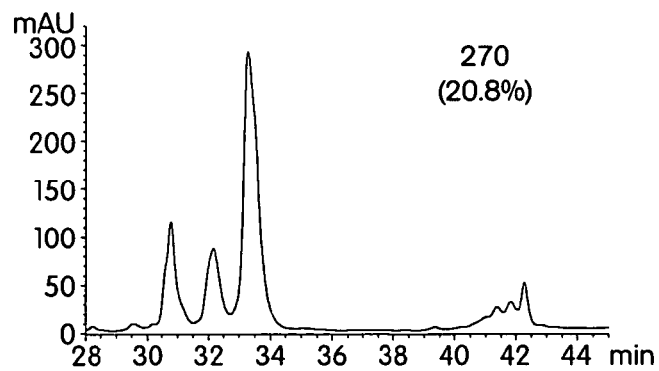
Figure 15E:
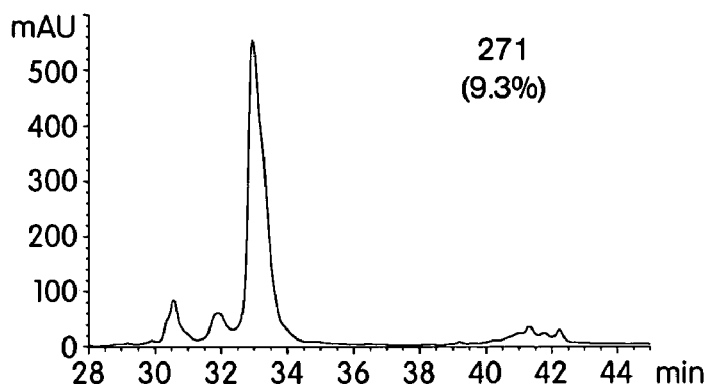
Figure 15F:
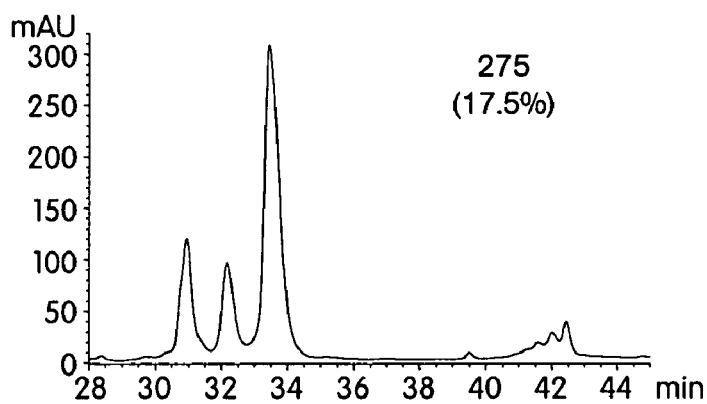
Figure 15G:
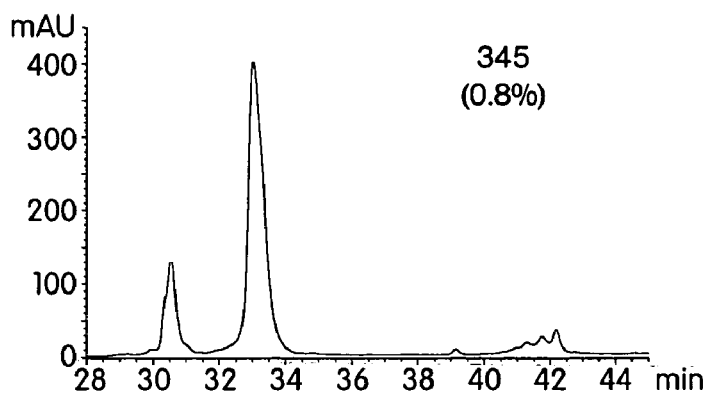
Figure 15H:
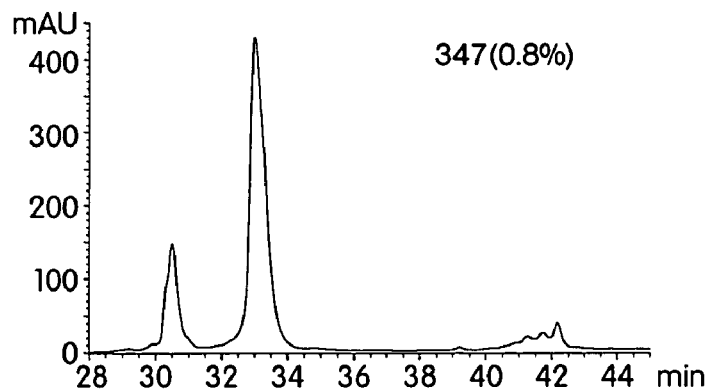

A mouse Sir2 homolog was identified in the EST database and cloned the full length cDNA, termed mSir2α (FIG. 12a). The conserved region of this protein resembles yeast Sir2p more closely than do other mouse Sir2 proteins (FIG. 12b). To determine whether the mouse Sir2p homolog mSir2α would catalyze this deacetylation reaction, we incubated purified recombinant mSir2α with the di-acetylated H3 peptide and analyzed the reaction products by HPLC (FIG. 12c). The murine protein gave rise to the same array of products with a similar yield as the yeast enzyme, indicating that this deacetylation reaction is conserved from yeast to mammals.

NADH, NADP, and NADPH do not Activate Deacetylation by Sir2p

While there are literally hundreds of NAD-linked dehydrogenases that use NAD and NADH in oxidation/reduction reactions in cells, for example, glyceraldehyde-3-phosphate dehydrogenase, the requirement for NAD to drive any other enzymatic reaction is novel. This suggested that Sir2 proteins might be sensors of the energy or oxidation state of cells that transduces this status to the organization of chromatin structure. Catabolic reactions in cells, such as substrate level and oxidative phosphorylation in the utilization of glucose, are oxidative and use NAD to produce NADH. Biosynthetic reactions typically are reductive and use NADPH to produce NADP. It was thus of interest to determine whether NADH, NADP, and NADPH would function in the deacetylation reaction.

As shown in FIG. 13, NADP and NADPH did not function significantly, while NADH functioned weakly in the deacetylation of the H3 peptide by Sir2p. In fact, the small amount of deacetylated products in the NADH reaction can reasonably be attributed to a low level of oxidation of the NADH preparation. Also, neither NADH nor NADP significantly inhibited the deacetylase activity in a reaction with NAD (not shown). This remarkable specificity of Sir2p for NAD but not the other dinucleotides may allow Sir2 proteins to sense the energy or oxidation status of cells to link histone deacetylation and chromatin silencing to the metabolic rate.

Histone Deacetylase Defective Sir2p Mutants Show Defects in Silencing, Recombination Suppression and Life Span The present invention shows that mutations in Sir2 proteins reduce or eliminate the enzymatic activity of the protein affect these various functions, indicating that the histone deacetylase activity of Sir2p is important in vivo.

A set of mutations in highly conserved residues of the core domain of SIR2 were constructed by site-directed mutagenesis (FIG. 17a) and cloned into vectors, along with the wild type, to allow expression of the recombinant proteins in E. coli or expression of single-copy genes from the native SIR2 promoter in S. cerevisiae. These 6xhis tagged proteins were purified from E. coli by a Ni-NTA column (FIG. 17b) and analyzed for the NAD-dependent histone H3 deacetylase activity in an assay with a di-acetylated H3 peptide (residues 1-20 acetylated on Lys9 and Lys14) and 1 mM NAD. HPLC separation of the reaction products yields five peaks of which 1, 2, a portion of 3 and 4 are deacetylated species of peptide (FIG. 15). In this deacetylase assay, mutants 345 and 347 were inactive, mutant 261 showed 17% of wild type activity, mutants 270 and 271 showed 80% and 36% wild type activity, respectively, and mutant 275 showed 67% wild type activity.

Figure 17A:
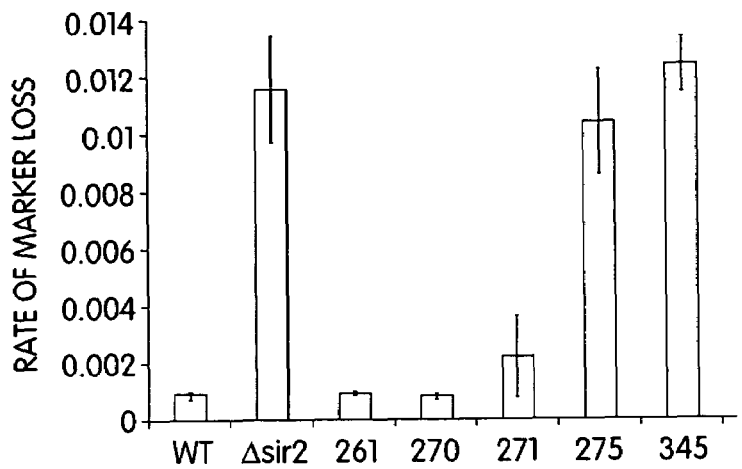
FIGS. 17a, 17b and 17c illustrate the effect of mutations in Sir2 on rDNA recombination and yeast life span.
Figure 17B:
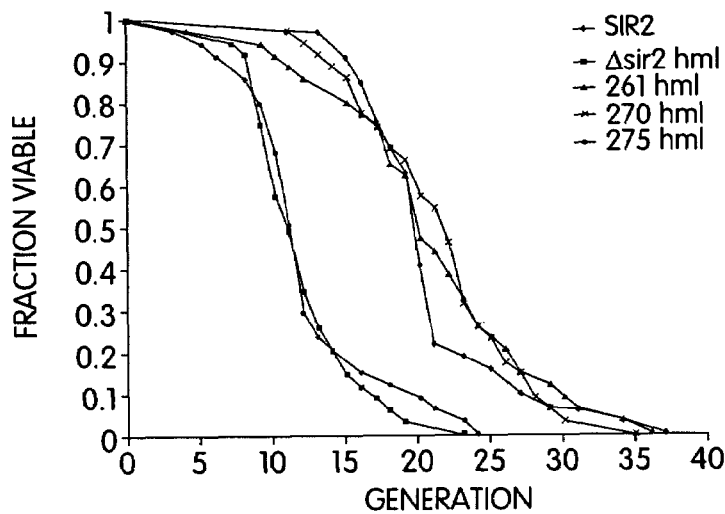
Figure 17C:
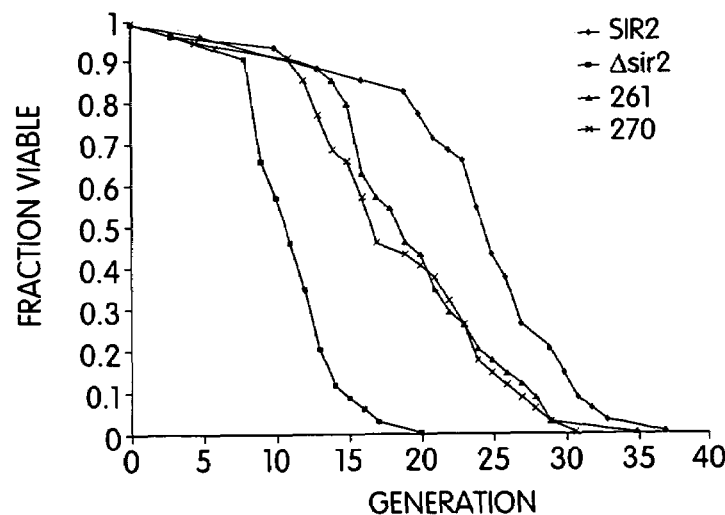

The Sir 2 mutant proteins were also analyzed for ADP-ribosyltransferase activity using the histone H3 substrate, (FIG. 17c). Mutants 345 and 347 were completely inactive, mutants 261, 270, and 271 displayed very weak activity, 4%, 7%, and 8%, respectively, and mutant 275 was about as active as wild type. The same pattern of activities was observed using a peptide of the N-terminal tail of histone H3 (not shown).

Figure 16A:
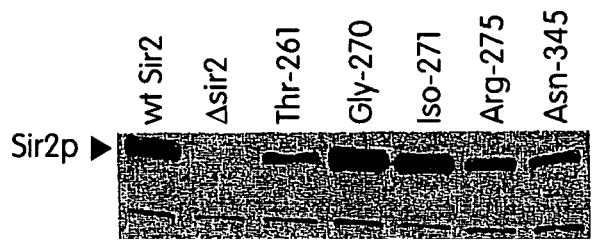
FIGS. 16a, 16b, 16c and 16d illustrate the effect of mutations on deacetylation in vitro and silencing in vivo. Wildtype (wt) and mutant Sir2 (Thr-261, Gly-270, Iso-271, Arg-275, Asn-345) were integrated into sir2Δ W303R strains.

To examine the functions of these mutants in vivo, we studied yeast indicator strains in which the endogenous SIR2 had been deleted and the wild type and mutant SIR2 genes integrated back into the genome. All strains used are isogenic derivatives of W303R (Kaeberlein, M., et al., Genes Dev. 13: 2570-2580 (1999)) and all results are summarized in FIG. 18. The mutant proteins were visualized by Western blot and found to be expressed at approximately the same level as wild type, with a small reduction in the level of mutant 261 and perhaps 275, and 345 (FIG. 16*a*).

Figure 16B:
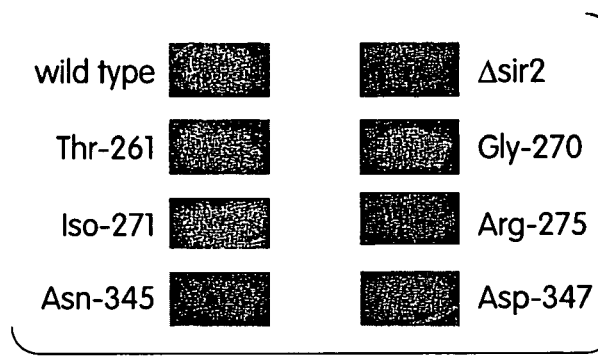
Figure 16C:
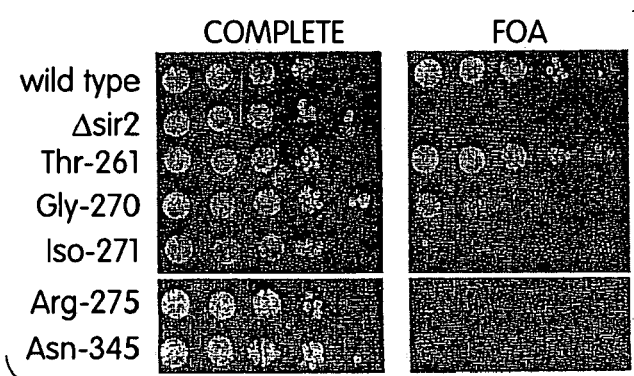
Figure 16D:
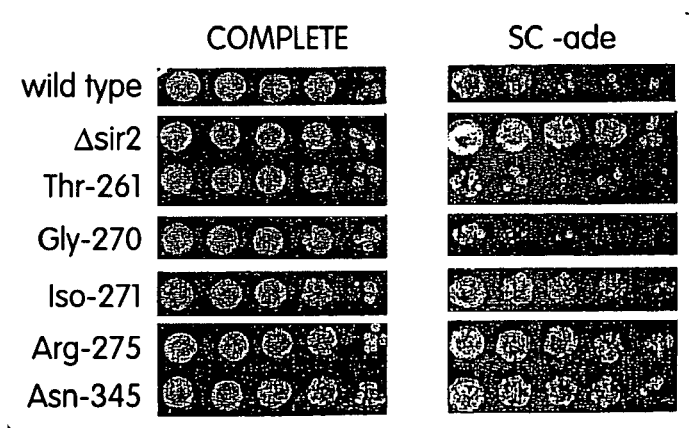

Silencing of the HMLα and HMRa mating loci was assayed by mating with a haploid strain of opposite mating type and monitoring the appearance of diploids on selective media. In this assay (FIG. 16*b*), mutants 261, 270, and 271 were mating proficient, indicating that silencing was essentially intact, and mutants 345, 347, and, surprisingly, 275 were defective. Telomere silencing was determined by repression of the telomere-positioned URA3 gene, which gives rise to growth on media containing 5-fluoro-orotic acid (FOA). Serial dilution of wild type and mutant strains on FOA plates indicated that mutant 261 silenced about as well as wild type, 270 showed partial silencing, and 271, 275, and 345 were defective (FIG. 16*c*). Silencing in the rDNA was determined by a serial dilution onto adenine-lacking media of strains with ADE2 inserted into the rDNA (Kaeberlein, M., et al., *Genes Dev.* 13: 2570-2580 (1999)). To facilitate detectable of differences in rDNA silencing, a rpd3AE strain was used which displays enhanced silencing (Smith, J. S., et al., *Mol. Cell Biol.* 19: 3184-3197 (1999)). By this assay mutants 261 and 270 silenced about as well as the wild type, mutant 271 showed weak silencing, and mutants 275, and 345 were totally defective (FIG. 16*d*).

The data indicate a general, although not strictly quantitative, correlation between deacetylase activity in vitro and silencing in vivo (except for 275, see below). Mutant 345 is inactive for deacetylase activity in vitro and silencing in vivo. Mutants 261, 270, and 271, have intermediate levels of deacetylase activities in vitro and intermediate effects on silencing in vivo. Mutant 261 is proficient in all silencing assays, but does show a defect in a more sensitive silencing assay of life span, below. Mutant 270 is proficient in HM and rDNA silencing but intermediate in silencing at telomeres, and 271 is proficient in HM silencing, but intermediate to weak in silencing at telomeres and rDNA. An intermediate levels of deacetylase activity can are sufficient to mediate silencing, but the specific level of silencing may be modulated by other variables affected by these mutations, such as the interaction of Sir2p with partner proteins. The lack of silencing activity in mutant 275 was unexpected and may reflect an inability of that mutant protein to localize properly in the nucleus or to interact with important partners in vivo.

Replicative life span of mother cells is due in part to the accumulation of extrachromosomal rDNA circles (Sinclair, D. A., et al., *Science* 277: 1313-1316 (1997); (Sinclair, D. A., et al., *Cell* 91: 1-20 (1997)) that arise by homologous recombination (Park, P. U., et al., *Mol. Cell. Biol.* 19: 3848-3856 (1999)) in the tandem array of rDNA repeats on chromosome XII. This recombination is suppressed 5-10 fold by SIR2 (Gottlieb, S., et al., *Cell* 56: 771-776 (1989)), allowing cells to enjoy their normal life span. To measure recombination frequencies, wild type and Sir2 mutant strains containing the ADE2 gene inserted into the rDNA were plated on YPD media. This media is limiting in adenine, causing ade2-colonies to accumulate a red pigment. Half-red/white sectored colonies indicate ADE2 loss in the first generation after plating, and the frequency of these colonies compared to Ade+ colonies is a direct measure of the recombination rate in the rDNA. By this assay, SIR2 suppressed recombination about 12-fold compared to the SIR2 deletion strain (FIG. 17*a*). Mutants 261 and 270, showed a high degree of suppression in the range of wild type, mutant 271 showed partial suppression, and mutants 275, and 345 were as defective as the SIR2 deletion. Thus, the activities of these mutants in this recombination assay are similar to their activities in the rDNA silencing assay, above.

Previous findings show that the short life span of SIR2 deletion mutants in strain W303R is a composite of a failure to suppress rDNA recombination and also a failure to repress transcription of the copies of mating type information at HM loci yielding the a/α cell type (Kaeberlein, M., et al., *Genes Dev.* 13: 2570-2580 (1999)). Expression of a/α leads to a higher rate of recombination in the rDNA. The life spans of representative mutants were first determined in strains in which HMLα was deleted to avoid any contribution of the a/α cell type if weak derepression occurred at those loci. The sir2 deletion shortened life span about 50% compared to wild type, as expected (FIG. 17*b*). Mutants 261 and 270 complemented the sir2 deletion to give a wild type life span and mutant 275 was completely defective in complementing the life span defect, consistent with the activities of these mutants in the recombination assay.

Life span determination in wild type HM strains is a very sensitive known assay for Sir2 activity in vivo, i.e. in this assay even SIR21SIR2 heterozygous diploids show a pronounced defect (Kaeberlein, M., et al., *Genes Dev.* 13: 2570-2580 (1999)). Thus, the life spans of SIR2 mutants were also determined in otherwise wild type haploid strains (FIG. 17*c*). Now a partial defect was observed in the 261 and 270 mutants, which can be attributed to a slight defect in the maintenance of repression at HM loci. Mutant 275 was again defective. Thus, with this sensitive assay, the 261 and 270 SIR2 mutants show defects, which parallel their enzymatic defects in vitro. Mutant 275 is exceptional, as in the above assays.

Previous studies indicate that the acetylation state of lysines in the amino-terminal tails of histones H3 and H4 is crucial for silencing in vivo (Braunstein, M., et al., *Genes Dev* 7: 592-604 (1993); (Braunstein, M., et al., *Mol. Cell. Biol.* 16: 4349-4356 (1996); (Turner, B. M., et al., *Cell* 69: 408-411 (1992)). Lysines 9 and 14 of H3 and lysines 5, 8, and 16 of H4 are hypoacetylated in silenced chromatin and return to their acetylated state in SIR mutants (Braunstein, M., et al., *Genes Dev* 7: 592-604 (1993); (Braunstein, M., et al., *Mol. Cell. Biol.* 16: 4349-4356 (1996)). Moreover, mutations in the lysines of the H3 tail, especially to uncharged residues, cause a loss of silencing (Thompson, J. S., et al., *Nature* 369: 245-247 (1994)). These data show that Sir2 mutations which eliminate deacetylase activity show silencing defects in vivo.

Taken together these findings suggest that the NAD-dependent histone deacetylase activity of Sir2p sufficiently explains the SIR2 functions of silencing, suppression of rDNA recombination, and life span extension in vivo. H3 and H4 are acetylated as a prerequisite to their recognition by chromatin assembly factors (Ma, X. J., et al., *Proc. Nat. Acad. Sci.* 95: 6693-6698 (1998)). Sir2p can be a target to specific genomic sites and initiates silencing by deacetylating H3 and, most likely, H4. It is possible that the putative ADP-ribosyltransferase activity of Sir2p also plays some role in these in vivo functions.

These data show that histone deacetylation by Sir2p has an absolute requirement for NAD. These data are striking and can couple chromatin silencing to the energy status of cells. Caloric restriction (Weindruch, R. H., et al., *J. Nutrit.* 116: 641-654 (1986)) increases life span in a wide variety of eukaryotic species. This regimen may increase available NAD and trigger the activity of Sir2 proteins, leading to greater silencing and a longer life span. Similarly normal aging can be caused, in part, by a decrease in the activity of Sir2 proteins, perhaps owing to a reduction in available NAD, causing a loss of silencing and the deleterious alteration in the pattern of gene expression.

Mouse Sir2p homolog mSir2α has histone deacetylase activity that closely resembles yeast Sir2p. The Sir2 proteins described herein and related mammalian Sir2 proteins (Brachmann, C. B., et al., *Genes Dev.* 9: 2888-2902 (1995); (Frye, R. A., *Biochem. Biophys. Res. Commun.* 260: 273-279 (1999)) could play regulated roles in chromatin structure, which might include changes in genome organization during cellular differentiation and in response to physiological stimuli, including caloric restriction. If aging were due, at least in part, to a loss of silencing, then interventions to increase the activity of Sir2 proteins can slow aging in mammals.

What is claimed is:

1. A method of evaluating the deacetylation of a histone protein in the presence of: (i) a Sir2 protein, (ii) NAD or an NAD-like compound, and (iii) an agent, the method comprising:
   a) combining:
      (i) a histone protein that comprises an acetylated amino acid side chain,
      (ii) an isolated or recombinantly produced Sir2 protein,
      (iii) NAD or an NAD-like compound, and
      (iv) an agent to be tested,
   thereby producing a combination; and
   b) determining if the histone protein is deacetylated.

2. A method of evaluating the deacetylation of a histone protein or an N-terminal fragment of an H3 or an H4 histone protein in the presence of a human Sir2 protein, NAD, and an agent, the method comprising:
   a) providing a mixture comprising
      (i) a histone protein or an N-terminal fragment of an H3 or an H4 histone protein that comprises an acetylated amino acid side chain, wherein the N-terminal fragment comprises amino acids 1-20 of SEQ ID NO:6; SEQ ID NO:7; or SEQ ID NO:8,
      (ii) an isolated or recombinantly produced human Sir2 protein,
      (iii) NAD, and
      (iv) an agent to be tested; and
   b) determining if the histone protein or the N-terminal fragment of an H3 or an H4 histone protein is deacetylated.

3. The method of claim 1 wherein step (b) comprises electron-spray mass spectroscopy.

4. The method of claim 1 further comprising comparing deacetylation of the histone protein in the presence of the agent to deacetylation of the histone protein in the absence of the agent, wherein a difference in histone protein deacetylation indicates that the agent alters Sir2 protein deacetylase activity.

5. The method of claim 1 wherein the Sir2 protein is a human Sir2 protein.

6. The method of claim 1 wherein the Sir2 protein is a murine Sir2 protein.

7. The method of claim 1 wherein the Sir2 protein is a fusion protein.

8. The method of claim 1 wherein the histone protein is histone H3.

9. The method of claim 1 wherein the histone protein is selected from the group consisting of an H2B, H3 and H4 histone protein.

10. The method of claim 1 wherein the histone protein is acetylated on a lysine amino acid residue.

11. The method of claim 1 wherein the Sir2 protein is an isolated Sir2 protein.

12. The method of claim 1 wherein the Sir2 protein is a recombinantly produced Sir2 protein.

13. The method of claim 1 wherein the combination comprises $MgCl_2$.

14. The method of claim 1 wherein the combination comprises dithiothreitol (DTT).

15. The method of claim 1 further comprising formulating the agent with a pharmaceutically acceptable carrier to provide a pharmaceutical composition.

16. The method of claim 15 wherein the pharmaceutically acceptable carrier comprises a carbohydrate.

17. The method of claim 1 wherein the combination comprises NAD.

18. The method of claim 1 wherein the Sir2 protein is a Sir2α protein.

19. The method of claim 18 wherein the Sir2α protein comprises SEQ ID NO:12.

20. The method of claim 2 wherein the mixture comprises $MgCl_2$.

21. The method of claim 2 wherein the mixture comprises dithiothreitol (DTT).

22. The method of claim 2 wherein the Sir2 protein is an isolated Sir2 protein.

23. The method of claim 2 wherein the Sir2 protein is a recombinantly produced Sir2 protein.

24. The method of claim 2, wherein the N-terminal fragment comprises SEQ ID NO:6.

25. The method of claim 2, wherein the N-terminal fragment comprises amino acids 1-20 of SEQ ID NO:6.

26. The method of claim 2, wherein the N-terminal fragment comprises SEQ ID NO:7 or SEQ ID NO:8.

27. The method of claim 2, wherein the N-terminal fragment consists of SEQ ID NO:6.

28. The method of claim 2, wherein the N-terminal fragment consists of amino acids 1-20 of SEQ ID NO:6.

29. The method of claim 2, wherein the N-terminal fragment consists of SEQ ID NO:7 or SEQ ID NO:8.

30. The method of claim 1 or 2 wherein the Sir2 protein is produced in *E. coli*.

31. The method of claim 1 or 2 wherein the agent is a protein.

32. The method of claim 31 wherein the agent is an antibody.

33. The method of claim 1 or 2 wherein the agent is a peptide.

34. The method of claim 1 or 2 wherein the agent is naturally occurring.

35. The method of claim 1 or 2 wherein the agent is non-naturally occurring.

36. The method of claim 1 or 2 wherein the agent is chemically synthesized.

37. The method of claim 1 or 2 wherein the agent is a carbohydrate.

38. The method of claim 1 or 2 wherein the agent is a steroid.

39. The method of claim 1 or 2 wherein the agent is a lipid.

40. The method of claim 1 or 2 wherein the agent is an anion.

41. The method of claim 1 or 2 wherein the agent is a cation.

42. The method of claim 1 or 2 wherein the agent is an oligonucleotide.

43. A method of evaluating the deacetylation of an N-terminal fragment of an H3 or an H4 histone protein in the presence of: (i) a Sir2 protein, (ii) NAD or an NAD-like compound, and (iii) an agent, the method comprising:
   a) combining:
      (i) an N-terminal tail of an H3 or an H4 histone protein that comprises an acetylated amino acid side chain, wherein the N-terminal tail comprises amino acids 1-20 of SEQ ID NO:6; SEQ ID NO:7; or SEQ ID NO:8,
      (ii) an isolated or recombinantly produced Sir2 protein,
      (iii) NAD or an NAD-like compound, and
      (iv) an agent to be tested,
      thereby producing a combination; and
   b) determining if the N-terminal tail of an H3 or H4 histone protein is deacetylated.

44. The method of claim 43, wherein the N-terminal tail comprises a SEQ ID NO:6.

45. The method of claim 43, wherein the N-terminal tail comprises amino acids 1-20 of SEQ ID NO:6.

46. The method of claim 43, wherein the N-terminal tail comprises SEQ ID NO:7 or SEQ ID NO:8.

47. The method of claim 43, wherein the N-terminal tail consists of SEQ ID NO:6.

48. The method of claim 43, wherein the N-terminal tail consists of amino acids 1-20 of SEQ ID NO:6.

49. The method of claim 43, wherein the N-terminal tail consists of SEQ ID NO:7 or SEQ ID NO:8.

* * * * *

UNITED STATES PATENT AND TRADEMARK OFFICE
CERTIFICATE OF CORRECTION

| | | |
|---|---|---|
| PATENT NO. | : 7,452,664 B2 | Page 1 of 1 |
| APPLICATION NO. | : 09/461580 | |
| DATED | : November 18, 2008 | |
| INVENTOR(S) | : Leonard Guarente et al. | |

It is certified that error appears in the above-identified patent and that said Letters Patent is hereby corrected as shown below:

Column 1, delete lines 7-9, and replace with --This invention was made with government support under grant number R01 AG011119 awarded by the NIH. The government has certain rights in this invention.--

Signed and Sealed this

Fourteenth Day of June, 2011

David J. Kappos
*Director of the United States Patent and Trademark Office*

SEQUENCE LISTING

```
<160> NUMBER OF SEQ ID NOS: 38

<210> SEQ ID NO 1
<211> LENGTH: 737
<212> TYPE: PRT
<213> ORGANISM: Mus musculus

<400> SEQUENCE: 1

Met Ala Asp Glu Val Ala Leu Ala Leu Gln Ala Ala Gly Ser Pro Ser
1               5                   10                  15

Ala Ala Ala Ala Met Glu Ala Ala Ser Gln Pro Ala Asp Glu Pro Leu
            20                  25                  30

Arg Lys Arg Pro Arg Arg Asp Gly Pro Gly Leu Gly Arg Ser Pro Gly
        35                  40                  45

Glu Pro Ser Ala Ala Val Ala Pro Ala Ala Gly Cys Glu Ala Ala
    50                  55                  60

Ser Ala Ala Pro Ala Ala Leu Trp Arg Glu Ala Ala Gly Ala Ala
65                  70                  75                  80

Ala Ser Ala Glu Arg Glu Ala Pro Ala Thr Ala Val Ala Gly Asp Gly
                85                  90                  95

Asp Asn Gly Ser Gly Leu Arg Arg Glu Pro Arg Ala Ala Asp Asp Phe
            100                 105                 110

Asp Asp Asp Glu Gly Glu Glu Glu Asp Glu Ala Ala Ala Ala Ala Ala
        115                 120                 125

Ala Ala Ala Ile Gly Tyr Arg Asp Asn Leu Leu Leu Thr Asp Gly Leu
    130                 135                 140

Leu Thr Asn Gly Phe His Ser Cys Glu Ser Asp Asp Asp Asp Arg Thr
145                 150                 155                 160

Ser His Ala Ser Ser Ser Asp Trp Thr Pro Arg Pro Arg Ile Gly Pro
                165                 170                 175

Tyr Thr Phe Val Gln Gln His Leu Met Ile Gly Thr Asp Pro Arg Thr
            180                 185                 190

Ile Leu Lys Asp Leu Leu Pro Glu Thr Ile Pro Pro Pro Glu Leu Asp
        195                 200                 205

Asp Met Thr Leu Trp Gln Ile Val Ile Asn Ile Leu Ser Glu Pro Pro
    210                 215                 220

Lys Arg Lys Lys Arg Lys Asp Ile Asn Thr Ile Glu Asp Ala Val Lys
225                 230                 235                 240

Leu Leu Gln Glu Cys Lys Lys Ile Ile Val Leu Thr Gly Ala Gly Val
                245                 250                 255

Ser Val Ser Cys Gly Ile Pro Asp Phe Arg Ser Arg Asp Gly Ile Tyr
            260                 265                 270

Ala Arg Leu Ala Val Asp Phe Pro Asp Leu Pro Asp Pro Gln Ala Met
        275                 280                 285

Phe Asp Ile Glu Tyr Phe Arg Lys Asp Pro Arg Pro Phe Phe Lys Phe
    290                 295                 300

Ala Lys Glu Ile Tyr Pro Gly Gln Phe Gln Pro Ser Leu Cys His Lys
```

-continued

```
305                 310                 315                 320

Phe Ile Ala Leu Ser Asp Lys Glu Gly Lys Leu Leu Arg Asn Tyr Thr
                325                 330                 335

Gln Asn Ile Asp Thr Leu Glu Gln Val Ala Gly Ile Gln Arg Ile Leu
                340                 345                 350

Gln Cys His Gly Ser Phe Ala Thr Ala Ser Cys Leu Ile Cys Lys Tyr
                355                 360                 365

Lys Val Asp Cys Glu Ala Val Arg Gly Asp Ile Phe Asn Gln Val Val
                370                 375                 380

Pro Arg Cys Pro Arg Cys Pro Ala Asp Glu Pro Leu Ala Ile Met Lys
385                 390                 395                 400

Pro Glu Ile Val Phe Phe Gly Glu Asn Leu Pro Glu Gln Phe His Arg
                405                 410                 415

Ala Met Lys Tyr Asp Lys Asp Glu Val Asp Leu Leu Ile Val Ile Gly
                420                 425                 430

Ser Ser Leu Lys Val Arg Pro Val Ala Leu Ile Pro Ser Ser Ile Pro
                435                 440                 445

His Glu Val Pro Gln Ile Leu Ile Asn Arg Glu Pro Leu Pro His Leu
                450                 455                 460

His Phe Asp Val Glu Leu Leu Gly Asp Cys Asp Val Ile Ile Asn Glu
465                 470                 475                 480

Leu Cys His Arg Leu Gly Gly Glu Tyr Ala Lys Leu Cys Cys Asn Pro
                485                 490                 495

Val Lys Leu Ser Glu Ile Thr Glu Lys Pro Pro Arg Pro Gln Lys Glu
                500                 505                 510

Leu Val His Leu Ser Glu Leu Pro Pro Thr Pro Leu His Ile Ser Glu
                515                 520                 525

Asp Ser Ser Pro Glu Arg Thr Val Pro Gln Asp Ser Ser Val Ile
                530                 535                 540

Ala Thr Leu Val Asp Gln Ala Thr Asn Asn Asn Val Asn Asp Leu Glu
545                 550                 555                 560

Val Ser Glu Ser Ser Cys Val Glu Glu Lys Pro Gln Glu Val Gln Thr
                565                 570                 575

Ser Arg Asn Val Glu Asn Ile Asn Val Glu Asn Pro Asp Phe Lys Ala
                580                 585                 590

Val Gly Ser Ser Thr Ala Asp Lys Asn Glu Arg Thr Ser Val Ala Glu
                595                 600                 605

Thr Val Arg Lys Cys Trp Pro Asn Arg Leu Ala Lys Glu Gln Ile Ser
                610                 615                 620

Lys Arg Leu Glu Gly Asn Gln Tyr Leu Phe Val Pro Pro Asn Arg Tyr
625                 630                 635                 640

Ile Phe His Gly Ala Glu Val Tyr Ser Asp Ser Glu Asp Asp Val Leu
                645                 650                 655

Ser Ser Ser Ser Cys Gly Ser Asn Ser Asp Ser Gly Thr Cys Gln Ser
                660                 665                 670

Pro Ser Leu Glu Glu Pro Leu Glu Asp Glu Ser Glu Ile Glu Glu Phe
                675                 680                 685

Tyr Asn Gly Leu Glu Asp Asp Thr Glu Arg Pro Glu Cys Ala Gly Gly
                690                 695                 700

Ser Gly Phe Gly Ala Asp Gly Asp Gln Glu Val Val Asn Glu Ala
705                 710                 715                 720

Ile Ala Thr Arg Gln Glu Leu Thr Asp Val Asn Tyr Pro Ser Asp Lys
                725                 730                 735
```

Ser

<210> SEQ ID NO 2
<211> LENGTH: 272
<212> TYPE: PRT
<213> ORGANISM: Saccharomyces cerevisiae

<400> SEQUENCE: 2

```
Ile Asn Lys Val Leu Cys Thr Arg Leu Arg Leu Ser Asn Phe Phe Thr
  1               5                  10                  15

Ile Asp His Phe Ile Gln Lys Leu His Thr Ala Arg Lys Ile Leu Val
             20                  25                  30

Leu Thr Gly Ala Gly Val Ser Thr Ser Leu Gly Ile Pro Asp Phe Arg
         35                  40                  45

Ser Ser Glu Gly Phe Tyr Ser Lys Ile Lys His Leu Gly Leu Asp Asp
     50                  55                  60

Pro Gln Asp Val Phe Asn Tyr Asn Ile Phe Met His Asp Pro Ser Val
 65                  70                  75                  80

Phe Tyr Asn Ile Ala Asn Met Val Leu Pro Pro Glu Lys Ile Tyr Ser
                 85                  90                  95

Pro Leu His Ser Phe Ile Lys Met Leu Gln Met Lys Gly Lys Leu Leu
            100                 105                 110

Arg Asn Tyr Thr Gln Asn Ile Asp Asn Leu Glu Ser Tyr Ala Gly Ile
        115                 120                 125

Ser Thr Asp Lys Leu Val Gln Cys His Gly Ser Phe Ala Thr Ala Thr
    130                 135                 140

Cys Val Thr Cys His Trp Asn Leu Pro Gly Glu Arg Ile Phe Asn Lys
145                 150                 155                 160

Ile Arg Asn Leu Glu Leu Pro Leu Cys Pro Tyr Cys Tyr Lys Lys Arg
                165                 170                 175

Arg Glu Tyr Phe Pro Glu Gly Tyr Asn Asn Lys Val Gly Val Ala Ala
            180                 185                 190

Ser Gln Gly Ser Met Ser Glu Arg Pro Pro Tyr Ile Leu Asn Ser Tyr
        195                 200                 205

Gly Val Leu Lys Pro Asp Ile Thr Phe Phe Gly Glu Ala Leu Pro Asn
    210                 215                 220

Lys Phe His Lys Ser Ile Arg Glu Asp Ile Leu Glu Cys Asp Leu Leu
225                 230                 235                 240

Ile Cys Ile Gly Thr Ser Leu Lys Val Ala Pro Val Ser Glu Ile Val
                245                 250                 255

Asn Met Val Pro Ser His Val Pro Gln Val Leu Ile Asn Arg Asp Pro
            260                 265                 270
```

<210> SEQ ID NO 3
<211> LENGTH: 267
<212> TYPE: PRT
<213> ORGANISM: Saccharomyces cerevisiae

<400> SEQUENCE: 3

```
Ile Asn Lys Val Leu Ser Thr Arg Leu Arg Leu Pro Asn Phe Asn Thr
  1               5                  10                  15

Ile Asp His Phe Thr Ala Thr Leu Arg Asn Ala Lys Lys Ile Leu Val
             20                  25                  30

Leu Thr Gly Ala Gly Val Ser Thr Ser Leu Gly Ile Pro Asp Phe Arg
         35                  40                  45
```

Ser Ser Glu Gly Phe Tyr Ser Lys Ile Arg His Leu Gly Leu Glu Asp
 50                  55                  60

Pro Gln Asp Val Phe Asn Leu Asp Ile Phe Leu Gln Asp Pro Ser Val
 65                  70                  75                  80

Phe Tyr Asn Ile Ala His Met Val Leu Pro Pro Glu Asn Met Tyr Ser
                     85                  90                  95

Pro Leu His Ser Phe Ile Lys Met Leu Gln Asp Lys Gly Lys Leu Leu
                    100                 105                 110

Arg Asn Tyr Thr Gln Asn Ile Asp Asn Leu Glu Ser Tyr Ala Gly Ile
                115                 120                 125

Asp Pro Asp Lys Leu Val Gln Cys His Gly Ser Phe Ala Thr Ala Ser
    130                 135                 140

Cys Val Thr Cys His Trp Gln Ile Pro Gly Glu Lys Ile Phe Glu Asn
145                 150                 155                 160

Ile Arg Asn Leu Glu Leu Pro Leu Cys Pro Tyr Cys Tyr Gln Lys Arg
                165                 170                 175

Lys Gln Tyr Phe Pro Met Ser Asn Gly Asn Asn Thr Val Gln Thr Asn
                180                 185                 190

Ile Asn Phe Asn Ser Pro Ile Leu Lys Ser Tyr Gly Val Leu Lys Pro
            195                 200                 205

Asp Met Thr Phe Phe Gly Glu Ala Leu Pro Ser Arg Phe His Lys Thr
    210                 215                 220

Ile Arg Lys Asp Ile Leu Glu Cys Asp Leu Leu Ile Cys Ile Gly Thr
225                 230                 235                 240

Ser Leu Lys Val Ala Pro Val Ser Glu Ile Val Asn Met Val Pro Ser
                245                 250                 255

His Val Pro Gln Ile Leu Ile Asn Arg Asp Met
                260                 265

<210> SEQ ID NO 4
<211> LENGTH: 245
<212> TYPE: PRT
<213> ORGANISM: Mus musculus

<400> SEQUENCE: 4

Val Ile Asn Ile Leu Ser Glu Pro Pro Lys Arg Lys Lys Arg Lys Asp
 1               5                  10                  15

Ile Asn Thr Ile Glu Asp Ala Val Lys Leu Leu Gln Glu Cys Lys Lys
                20                  25                  30

Ile Ile Val Leu Thr Gly Ala Gly Val Ser Val Ser Cys Gly Ile Pro
            35                  40                  45

Asp Phe Arg Ser Arg Asp Gly Ile Tyr Ala Arg Leu Ala Val Asp Phe
    50                  55                  60

Pro Asp Leu Pro Asp Pro Gln Ala Met Phe Asp Ile Glu Tyr Phe Arg
 65                 70                  75                  80

Lys Asp Pro Arg Pro Phe Phe Lys Phe Ala Lys Glu Ile Tyr Pro Gly
                85                  90                  95

Gln Phe Gln Pro Ser Leu Cys His Lys Phe Ile Ala Leu Ser Asp Lys
                100                 105                 110

Glu Gly Lys Leu Leu Arg Asn Tyr Thr Gln Asn Ile Asp Thr Leu Glu
            115                 120                 125

Gln Val Ala Gly Ile Gln Arg Ile Leu Gln Cys His Gly Ser Phe Ala
    130                 135                 140

Thr Ala Ser Cys Leu Ile Cys Lys Tyr Lys Val Asp Cys Glu Ala Val
145                 150                 155                 160

```
Arg Gly Asp Ile Phe Asn Gln Val Val Pro Arg Cys Pro Arg Cys Pro
                165                 170                 175

Ala Asp Glu Pro Leu Ala Ile Met Lys Pro Glu Ile Val Phe Phe Gly
            180                 185                 190

Glu Asn Leu Pro Glu Gln Phe His Arg Ala Met Lys Tyr Asp Lys Asp
        195                 200                 205

Glu Val Asp Leu Leu Ile Val Ile Gly Ser Ser Leu Lys Val Arg Pro
    210                 215                 220

Val Ala Leu Ile Pro Ser Ser Ile Pro His Glu Val Pro Gln Ile Leu
225                 230                 235                 240

Ile Asn Arg Glu Pro
                245

<210> SEQ ID NO 5
<211> LENGTH: 237
<212> TYPE: PRT
<213> ORGANISM: Salmonella typhimurium

<400> SEQUENCE: 5

Met Met Glu Asn Pro Arg Val Leu Val Leu Thr Gly Ala Gly Ile Ser
 1               5                  10                  15

Ala Glu Ser Gly Ile Arg Thr Phe Arg Ala Ala Asp Gly Leu Trp Glu
            20                  25                  30

Glu His Arg Val Glu Asp Val Ala Thr Pro Glu Gly Phe Ala Arg Asn
        35                  40                  45

Pro Gly Leu Val Gln Thr Phe Tyr Asn Ala Arg Arg Gln Gln Leu Gln
    50                  55                  60

Gln Pro Glu Ile Gln Pro Asn Ala Ala His Leu Ala Leu Ala Asn Leu
65                  70                  75                  80

Lys Lys Arg Leu Ala Ile Ala Phe Leu Leu Val Thr Gln Asn Ile Asp
                85                  90                  95

Asn Leu His Glu Arg Ala Gly Asn Arg Asn Ile Ile Gln Met His Gly
            100                 105                 110

Glu Leu Leu Lys Val Arg Cys Ser Gln Ser Gly Gln Ile Leu Glu Trp
        115                 120                 125

Asn Gly Asp Val Met Pro Glu Asp Lys Cys His Cys Cys Gln Phe Pro
    130                 135                 140

Ala Pro Leu Arg Pro His Val Val Trp Phe Gly Glu Met Pro Leu Gly
145                 150                 155                 160

Met Asp Glu Ile Tyr Met Ala Leu Ser Met Ala Asp Ile Phe Ile Ala
                165                 170                 175

Ile Gly Thr Ser Gly His Val Tyr Pro Ala Ala Gly Phe Val His Glu
            180                 185                 190

Ala Lys Leu His Gly Ala His Thr Val Glu Leu Asn Leu Glu Pro Ser
        195                 200                 205

Gln Val Gly Asn Glu Phe Glu Glu Lys His Tyr Gly Pro Ala Ser Gln
    210                 215                 220

Val Val Pro Glu Phe Val Asp Lys Phe Leu Lys Gly Leu
225                 230                 235

<210> SEQ ID NO 6
<211> LENGTH: 21
<212> TYPE: PRT
<213> ORGANISM: Homo sapiens

<400> SEQUENCE: 6
```

```
Ala Arg Thr Lys Gln Thr Ala Arg Lys Ser Thr Gly Gly Lys Ala Pro
 1               5                  10                  15

Arg Lys Gln Leu Cys
            20

<210> SEQ ID NO 7
<211> LENGTH: 20
<212> TYPE: PRT
<213> ORGANISM: Homo sapiens

<400> SEQUENCE: 7

Ser Gly Arg Gly Lys Gly Gly Lys Gly Leu Gly Lys Gly Gly Ala Lys
 1               5                  10                  15

Arg His Arg Cys
            20

<210> SEQ ID NO 8
<211> LENGTH: 19
<212> TYPE: PRT
<213> ORGANISM: Homo sapiens

<400> SEQUENCE: 8

Ala Gly Gly Lys Gly Gly Lys Gly Met Gly Lys Val Gly Ala Lys Arg
 1               5                  10                  15

His Ser Cys

<210> SEQ ID NO 9
<211> LENGTH: 128
<212> TYPE: PRT
<213> ORGANISM: Mus musculus

<400> SEQUENCE: 9

Ile Val Leu Thr Gly Ala Gly Val Ser Val Ser Cys Gly Ile Pro Asp
 1               5                  10                  15

Phe Arg Ser Arg Asp Gly Ile Tyr Ala Arg Leu Ala Val Asp Phe Pro
                20                  25                  30

Asp Leu Pro Asp Pro Gln Ala Met Phe Asp Ile Glu Tyr Phe Arg Lys
            35                  40                  45

Asp Pro Arg Pro Phe Phe Lys Phe Ala Lys Glu Ile Tyr Pro Gly Gln
        50                  55                  60

Phe Gln Pro Ser Leu Cys His Lys Phe Ile Ala Leu Ser Asp Lys Glu
65                  70                  75                  80

Gly Lys Leu Leu Arg Asn Tyr Thr Gln Asn Ile Asp Thr Leu Glu Gln
                85                  90                  95

Val Ala Gly Ile Gln Arg Ile Leu Gln Cys His Gly Ser Phe Ala Thr
                100                 105                 110

Ala Ser Cys Leu Ile Cys Lys Tyr Lys Val Asp Cys Glu Ala Val Arg
            115                 120                 125

<210> SEQ ID NO 10
<211> LENGTH: 128
<212> TYPE: PRT
<213> ORGANISM: Saccharomyces cerevisiae

<400> SEQUENCE: 10

Leu Val Leu Thr Gly Ala Gly Val Ser Thr Ser Leu Gly Ile Pro Asp
 1               5                  10                  15

Phe Arg Ser Ser Glu Gly Phe Tyr Ser Lys Ile Lys His Leu Gly Leu
                20                  25                  30
```

-continued

Asp Asp Pro Gln Asp Val Phe Asn Tyr Asn Ile Phe Met His Asp Pro
            35                  40                  45

Ser Val Phe Tyr Asn Ile Ala Asn Met Val Leu Pro Pro Glu Lys Ile
 50                  55                  60

Tyr Ser Pro Leu His Ser Phe Ile Lys Met Leu Gln Met Lys Gly Lys
 65                  70                  75                  80

Leu Leu Arg Asn Tyr Thr Gln Asn Ile Asp Asn Leu Glu Ser Tyr Ala
                85                  90                  95

Gly Ile Ser Thr Asp Lys Leu Val Gln Cys His Gly Ser Phe Ala Thr
                100                 105                 110

Ala Thr Cys Val Thr Cys His Trp Asn Leu Pro Gly Glu Arg Ile Phe
            115                 120                 125

<210> SEQ ID NO 11
<211> LENGTH: 336
<212> TYPE: PRT
<213> ORGANISM: Saccharomyces cerevisiae

<400> SEQUENCE: 11

Ala Ile Asn Lys Val Leu Cys Thr Arg Leu Arg Leu Ser Asn Phe Phe
 1               5                  10                  15

Thr Ile Asp His Phe Ile Gln Lys Leu His Thr Ala Arg Lys Ile Leu
            20                  25                  30

Val Leu Thr Gly Ala Gly Val Ser Thr Ser Leu Gly Ile Pro Asp Phe
        35                  40                  45

Arg Ser Ser Glu Gly Phe Tyr Ser Lys Ile Lys His Leu Gly Leu Asp
 50                  55                  60

Asp Pro Gln Asp Val Phe Asn Tyr Asn Ile Phe Met His Asp Pro Ser
 65                  70                  75                  80

Val Phe Tyr Asn Ile Ala Asn Met Val Leu Pro Pro Glu Lys Ile Tyr
                85                  90                  95

Ser Pro Leu His Ser Phe Ile Lys Met Leu Gln Met Lys Gly Lys Leu
            100                 105                 110

Leu Arg Asn Tyr Thr Gln Asn Ile Asp Asn Leu Glu Ser Tyr Ala Gly
        115                 120                 125

Ile Ser Thr Asp Lys Leu Val Gln Cys His Gly Ser Phe Ala Thr Ala
130                 135                 140

Thr Cys Val Thr Cys His Trp Asn Leu Pro Gly Glu Arg Ile Phe Asn
145                 150                 155                 160

Lys Ile Arg Asn Leu Glu Leu Pro Leu Cys Pro Tyr Cys Tyr Lys Lys
                165                 170                 175

Arg Arg Glu Tyr Phe Pro Glu Gly Tyr Asn Asn Lys Val Gly Val Ala
            180                 185                 190

Ala Ser Gln Gly Ser Met Ser Glu Arg Pro Pro Tyr Ile Leu Asn Ser
        195                 200                 205

Tyr Gly Val Leu Lys Pro Asp Ile Thr Phe Phe Gly Glu Ala Leu Pro
210                 215                 220

Asn Lys Phe His Lys Ser Ile Arg Glu Asp Ile Leu Glu Cys Asp Leu
225                 230                 235                 240

Leu Ile Cys Ile Gly Thr Ser Leu Lys Val Ala Pro Val Ser Glu Ile
                245                 250                 255

Val Asn Met Val Pro Ser His Val Pro Gln Val Leu Ile Asn Arg Asp
            260                 265                 270

Pro Val Lys His Ala Glu Phe Asp Leu Ser Leu Leu Gly Tyr Cys Asp

```
                275                 280                 285
Asp Ile Ala Ala Met Val Ala Gln Lys Cys Gly Trp Thr Ile Pro His
    290                 295                 300

Lys Lys Trp Asn Asp Leu Lys Asn Lys Asn Phe Lys Cys Gln Glu Lys
305                 310                 315                 320

Asp Lys Gly Val Tyr Val Val Thr Ser Asp Glu His Pro Lys Thr Leu
                325                 330                 335

<210> SEQ ID NO 12
<211> LENGTH: 327
<212> TYPE: PRT
<213> ORGANISM: Mus musculus

<400> SEQUENCE: 12

Val Ile Asn Ile Leu Ser Glu Pro Pro Lys Arg Lys Arg Lys Asp
  1               5                  10                  15

Ile Asn Thr Ile Glu Asp Ala Val Lys Leu Leu Gln Glu Cys Lys Lys
             20                  25                  30

Ile Ile Val Leu Thr Gly Ala Gly Val Ser Val Ser Cys Gly Ile Pro
         35                  40                  45

Asp Phe Arg Ser Arg Asp Gly Ile Tyr Ala Arg Leu Ala Val Asp Phe
     50                  55                  60

Pro Asp Leu Pro Asp Pro Gln Ala Met Phe Asp Ile Glu Tyr Phe Arg
 65                  70                  75                  80

Lys Asp Pro Arg Pro Phe Phe Lys Phe Ala Lys Glu Ile Tyr Pro Gly
                 85                  90                  95

Gln Phe Gln Pro Ser Leu Cys His Lys Phe Ile Ala Leu Ser Asp Lys
            100                 105                 110

Glu Gly Lys Leu Leu Arg Asn Tyr Thr Gln Asn Ile Asp Thr Leu Glu
        115                 120                 125

Gln Val Ala Gly Ile Gln Arg Ile Leu Gln Cys His Gly Ser Phe Ala
    130                 135                 140

Thr Ala Ser Cys Leu Ile Cys Lys Tyr Lys Val Asp Cys Glu Ala Val
145                 150                 155                 160

Arg Gly Asp Ile Phe Asn Gln Val Val Pro Arg Cys Pro Arg Cys Pro
                165                 170                 175

Ala Asp Glu Pro Leu Ala Ile Met Lys Pro Glu Ile Val Phe Phe Gly
            180                 185                 190

Glu Asn Leu Pro Glu Gln Phe His Arg Ala Met Lys Tyr Asp Lys Asp
        195                 200                 205

Glu Val Asp Leu Leu Ile Val Ile Gly Ser Ser Leu Lys Val Arg Pro
    210                 215                 220

Val Ala Leu Ile Pro Ser Ser Ile Pro His Glu Val Pro Gln Ile Leu
225                 230                 235                 240

Ile Asn Arg Glu Pro Leu Pro His Leu His Phe Asp Val Glu Leu Leu
                245                 250                 255

Gly Asp Cys Asp Val Ile Ile Asn Glu Leu Cys His Arg Leu Gly Gly
            260                 265                 270

Glu Tyr Ala Lys Leu Cys Cys Asn Pro Val Lys Leu Ser Glu Ile Thr
        275                 280                 285

Glu Lys Pro Pro Arg Pro Gln Lys Glu Leu Val His Leu Ser Glu Leu
    290                 295                 300

Pro Pro Thr Pro Leu His Ile Ser Glu Asp Ser Ser Ser Pro Glu Arg
305                 310                 315                 320
```

Thr Val Pro Gln Asp Ser Ser
            325

<210> SEQ ID NO 13
<211> LENGTH: 237
<212> TYPE: PRT
<213> ORGANISM: Salmonella typhimurium

<400> SEQUENCE: 13

Met Met Glu Asn Pro Arg Val Leu Val Leu Thr Gly Ala Gly Ile Ser
1               5                   10                  15

Ala Glu Ser Gly Ile Arg Thr Phe Arg Ala Ala Asp Gly Leu Trp Glu
            20                  25                  30

Glu His Arg Val Glu Asp Val Ala Thr Pro Glu Gly Pro Ala Arg Asn
        35                  40                  45

Pro Gly Leu Val Gln Thr Phe Tyr Asn Ala Arg Arg Gln Gln Leu Gln
    50                  55                  60

Gln Pro Glu Ile Gln Pro Asn Ala Ala His Leu Ala Leu Ala Asn Leu
65                  70                  75                  80

Lys Lys Arg Leu Ala Ile Ala Phe Leu Leu Val Thr Gln Asn Ile Asp
                85                  90                  95

Asn Leu His Glu Arg Ala Gly Asn Arg Asn Ile Ile Gln Met His Gly
            100                 105                 110

Glu Leu Leu Lys Val Arg Cys Ser Gln Ser Gly Gln Ile Leu Glu Trp
        115                 120                 125

Asn Gly Asp Val Met Pro Glu Asp Lys Cys His Cys Cys Gln Phe Pro
    130                 135                 140

Ala Pro Leu Arg Pro His Val Val Trp Phe Gly Glu Met Pro Leu Gly
145                 150                 155                 160

Met Asp Glu Ile Tyr Met Ala Leu Ser Met Ala Asp Ile Phe Ile Ala
                165                 170                 175

Ile Gly Thr Ser Gly His Val Tyr Pro Ala Ala Gly Phe Val His Glu
            180                 185                 190

Ala Lys Leu His Gly Ala His Thr Val Glu Leu Asn Leu Glu Pro Ser
        195                 200                 205

Gln Val Gly Asn Glu Phe Glu Glu Lys His Tyr Gly Pro Ala Ser Gln
    210                 215                 220

Val Val Pro Glu Phe Val Asp Lys Phe Leu Lys Gly Leu
225                 230                 235

<210> SEQ ID NO 14
<211> LENGTH: 106
<212> TYPE: PRT
<213> ORGANISM: Saccharomyces cerevisiae

<400> SEQUENCE: 14

Ile Leu Val Leu Thr Gly Ala Gly Val Ser Thr Ser Leu Gly Ile Pro
1               5                   10                  15

Asp Phe Arg Ser Ser Glu Gly Phe Tyr Ser Lys Ile Lys His Leu Gly
            20                  25                  30

Leu Asp Asp Pro Gln Asp Val Phe Asn Tyr Asn Ile Phe Met His Asp
        35                  40                  45

Pro Ser Val Phe Tyr Asn Ile Ala Asn Met Val Leu Pro Pro Glu Lys
    50                  55                  60

Ile Tyr Ser Pro Leu His Ser Phe Ile Lys Met Leu Gln Met Lys Gly
65                  70                  75                  80

```
Lys Leu Leu Arg Asn Tyr Thr Gln Asn Ile Asp Asn Leu Glu Ser Tyr
             85                  90                  95

Ala Gly Ile Ser Thr Asp Lys Leu Val Gln
            100                 105

<210> SEQ ID NO 15
<211> LENGTH: 106
<212> TYPE: PRT
<213> ORGANISM: Saccharomyces cerevisiae

<400> SEQUENCE: 15

Ile Leu Val Leu Thr Gly Ala Gly Val Ser Thr Ser Leu Gly Ile Pro
 1               5                  10                  15

Asp Phe Arg Ser Ser Glu Gly Phe Tyr Ser Lys Ile Arg His Leu Gly
            20                  25                  30

Leu Glu Asp Pro Gln Asp Val Phe Asn Leu Asp Ile Phe Leu Gln Asp
        35                  40                  45

Pro Ser Val Phe Tyr Asn Ile Ala His Met Val Leu Pro Pro Glu Asn
    50                  55                  60

Met Tyr Ser Pro Leu His Ser Phe Ile Lys Met Leu Gln Asp Lys Gly
65                  70                  75                  80

Lys Leu Leu Arg Asn Tyr Thr Gln Asn Ile Asp Asn Leu Glu Ser Tyr
             85                  90                  95

Ala Gly Ile Asp Pro Asp Lys Leu Val Gln
            100                 105

<210> SEQ ID NO 16
<211> LENGTH: 107
<212> TYPE: PRT
<213> ORGANISM: Saccharomyces cerevisiae

<400> SEQUENCE: 16

Val Ile Phe Met Val Gly Ala Gly Ile Ser Thr Ser Cys Gly Ile Pro
 1               5                  10                  15

Asp Phe Arg Ser Pro Gly Thr Gly Leu Tyr His Asn Leu Ala Arg Leu
            20                  25                  30

Lys Leu Pro Tyr Pro Glu Ala Val Phe Asp Val Asp Phe Phe Gln Ser
        35                  40                  45

Asp Pro Leu Pro Phe Tyr Thr Leu Ala Lys Glu Leu Tyr Pro Gly Asn
    50                  55                  60

Phe Arg Pro Ser Lys Phe His Tyr Leu Leu Lys Leu Phe Gln Asp Lys
65                  70                  75                  80

Asp Val Leu Lys Arg Val Tyr Thr Gln Asn Ile Asp Thr Leu Glu Arg
             85                  90                  95

Gln Ala Gly Val Lys Asp Asp Leu Ile Ile Glu
            100                 105

<210> SEQ ID NO 17
<211> LENGTH: 131
<212> TYPE: PRT
<213> ORGANISM: Saccharomyces cerevisiae

<400> SEQUENCE: 17

Ile Ala Cys Leu Thr Gly Ala Gly Ile Ser Cys Asn Ala Gly Ile Pro
 1               5                  10                  15

Asp Phe Arg Ser Ser Asp Gly Leu Tyr Asp Leu Val Lys Lys Asp Cys
            20                  25                  30

Ser Gln Tyr Trp Ser Ile Lys Ser Gly Arg Glu Met Phe Asp Ile Ser
```

```
                 35                  40                  45
Leu Phe Arg Asp Asp Phe Lys Ile Ser Ile Phe Ala Lys Phe Met Glu
 50                  55                  60

Arg Leu Tyr Ser Asn Val Gln Leu Ala Lys Pro Thr Lys Thr His Lys
 65                  70                  75                  80

Phe Ile Ala His Leu Lys Asp Arg Asn Lys Leu Leu Arg Cys Tyr Thr
                 85                  90                  95

Gln Asn Ile Asp Gly Leu Glu Glu Ser Ile Gly Leu Thr Leu Ser Asn
                100                 105                 110

Arg Lys Leu Pro Leu Thr Ser Phe Ser Ser His Trp Lys Asn Leu Asp
                115                 120                 125

Val Val Gln
        130

<210> SEQ ID NO 18
<211> LENGTH: 117
<212> TYPE: PRT
<213> ORGANISM: Saccharomyces cerevisiae

<400> SEQUENCE: 18

Met Val Val Val Ser Gly Ala Gly Ile Ser Val Ala Ala Gly Ile Pro
  1               5                  10                  15

Asp Phe Arg Ser Ser Glu Gly Ile Phe Ser Thr Val Asn Gly Gly Ser
                 20                  25                  30

Gly Lys Asp Leu Phe Asp Tyr Asn Arg Val Tyr Gly Asp Glu Ser Met
                 35                  40                  45

Ser Leu Lys Phe Asn Gln Leu Met Val Ser Leu Phe Arg Leu Ser Lys
 50                  55                  60

Asn Cys Gln Pro Thr Lys Phe His Glu Met Leu Asn Glu Phe Ala Arg
 65                  70                  75                  80

Asp Gly Arg Leu Leu Arg Leu Tyr Thr Gln Asn Ile Asp Gly Leu Asp
                 85                  90                  95

Thr Gln Leu Pro His Leu Ser Thr Asn Val Pro Leu Ala Lys Pro Ile
                100                 105                 110

Pro Ser Thr Val Gln
            115

<210> SEQ ID NO 19
<211> LENGTH: 106
<212> TYPE: PRT
<213> ORGANISM: Mus musculus

<400> SEQUENCE: 19

Ile Ile Val Leu Thr Gly Ala Gly Val Ser Val Ser Cys Gly Ile Pro
  1               5                  10                  15

Asp Phe Arg Ser Arg Asp Gly Ile Tyr Ala Arg Leu Ala Val Asp Phe
                 20                  25                  30

Pro Asp Leu Pro Asp Pro Gln Ala Met Phe Asp Ile Glu Tyr Phe Arg
                 35                  40                  45

Lys Asp Pro Arg Pro Phe Phe Lys Phe Ala Lys Glu Ile Tyr Pro Gly
 50                  55                  60

Gln Phe Gln Pro Ser Leu Cys His Lys Phe Ile Ala Leu Ser Asp Lys
 65                  70                  75                  80

Glu Gly Lys Leu Leu Arg Asn Tyr Thr Gln Asn Ile Asp Thr Leu Glu
                 85                  90                  95

Gln Val Ala Gly Ile Gln Arg Ile Leu Gln
```

-continued

```
                100                 105

<210> SEQ ID NO 20
<211> LENGTH: 107
<212> TYPE: PRT
<213> ORGANISM: Mus musculus

<400> SEQUENCE: 20

Val Ile Cys Leu Val Gly Ala Gly Ile Ser Thr Ser Ala Gly Ile Pro
1               5                   10                  15

Asp Phe Arg Ser Pro Ser Thr Gly Leu Tyr Ala Asn Leu Glu Lys Tyr
                20                  25                  30

His Leu Pro Tyr Pro Glu Ala Ile Phe Glu Ile Ser Tyr Phe Lys Lys
            35                  40                  45

His Pro Glu Pro Phe Phe Ala Leu Ala Lys Glu Leu Tyr Pro Gly Gln
        50                  55                  60

Phe Lys Pro Thr Ile Cys His Tyr Phe Ile Arg Leu Leu Lys Glu Lys
65                  70                  75                  80

Gly Leu Leu Arg Cys Tyr Thr Gln Asn Ile Asp Thr Leu Glu Arg
                85                  90                  95

Val Ala Gly Leu Glu Pro Gln Asp Leu Val Glu
                100                 105

<210> SEQ ID NO 21
<211> LENGTH: 86
<212> TYPE: PRT
<213> ORGANISM: Mus musculus

<400> SEQUENCE: 21

Gly Thr Arg Leu Tyr Ser Asn Leu Gln Gln Tyr Asp Ile Pro Tyr Pro
1               5                   10                  15

Glu Ala Ile Phe Glu Leu Gly Phe Phe Phe His Asn Pro Lys Pro Phe
                20                  25                  30

Phe Met Leu Ala Lys Glu Leu Tyr Pro Gly His Tyr Arg Pro Asn Val
            35                  40                  45

Thr His Tyr Phe Leu Arg Leu His Asp Lys Glu Leu Leu Leu Arg
        50                  55                  60

Leu Tyr Thr Gln Asn Ile Asp Gly Leu Glu Arg Ala Ser Gly Ile Pro
65                  70                  75                  80

Ala Ser Lys Leu Val Glu
                85

<210> SEQ ID NO 22
<211> LENGTH: 85
<212> TYPE: PRT
<213> ORGANISM: Unknown
<220> FEATURE:
<223> OTHER INFORMATION: Unknown Protein

<400> SEQUENCE: 22

Val Val Phe His Thr Gly Ala Gly Ile Ser Thr Ala Ser Gly Ile Pro
1               5                   10                  15

Asp Phe Arg Gly Pro His Gly Val Trp Thr Met Glu Glu Arg Gly Leu
                20                  25                  30

Ala Pro Lys Phe Asp Thr Thr Phe Glu Asn Ala Arg Pro Ser Lys Thr
            35                  40                  45

His Met Ala Leu Val Gln Leu Glu Arg Met Gly Phe Leu Ser Phe Leu
        50                  55                  60
```

Val Ser Gln Asn Val Asp Gly Leu Asp Val Arg Ser Gly Phe Pro Arg
65                  70                  75                  80

Asp Lys Leu Ala Glu
                85

<210> SEQ ID NO 23
<211> LENGTH: 71
<212> TYPE: PRT
<213> ORGANISM: Unknown
<220> FEATURE:
<223> OTHER INFORMATION: Unknown Protein

<400> SEQUENCE: 23

Leu Leu Val Met Thr Gly Ala Gly Ile Ser Thr Glu Ser Gly Ile Pro
1               5                   10                  15

Asp Tyr Arg Ser Glu Lys Val Gly Leu Tyr Ala Arg Thr Asp Arg Arg
            20                  25                  30

Pro Ile Gln His Ile Asp Phe Val Pro Val Leu Arg Ser Ala Ser Gly
        35                  40                  45

Thr Trp Pro Glu Asn Leu Trp Ala Gly Leu Asn Ser Pro Leu Thr Asn
    50                  55                  60

Pro Thr Gln His Thr Trp Leu
65                  70

<210> SEQ ID NO 24
<211> LENGTH: 75
<212> TYPE: PRT
<213> ORGANISM: Unknown
<220> FEATURE:
<223> OTHER INFORMATION: Unknown Protein

<400> SEQUENCE: 24

Ile Ala Ile Ile Ser Gly Ala Gly Val Ser Ala Glu Ser Gly Val Pro
1               5                   10                  15

Thr Phe Arg Gly Ala Gly Gly Tyr Trp Arg Lys Trp Gln Ala Gln Asp
            20                  25                  30

Leu Ala Thr Pro Gln Ala Phe Ala Arg Asn Pro Ser Gln Val Trp Glu
        35                  40                  45

Phe Tyr His Tyr Arg Arg Glu Val Met Arg Ser Lys Glu Pro Asn Pro
    50                  55                  60

Gly His Leu Ala Ile Ala Gln Cys Glu Ala Arg
65                  70                  75

<210> SEQ ID NO 25
<211> LENGTH: 3869
<212> TYPE: DNA
<213> ORGANISM: Mus musculus
<220> FEATURE:
<221> NAME/KEY: CDS
<222> LOCATION: (48)...(2258)

<400> SEQUENCE: 25
gcggagcaga ggaggcgagg gcggagggcc agagaggcag ttggaag atg gcg gac         56
                                                    Met Ala Asp
                                                    1 gag gtg gcg ctc gcc ctt cag gcc gcc ggc tcc cct tcc gcg gcg gcc        104
Glu Val Ala Leu Ala Leu Gln Ala Ala Gly Ser Pro Ser Ala Ala Ala
    5                   10                  15 gcc atg gag gcc gcg tcg cag ccg gcg gac gag ccg ctc cgc aag agg        152
Ala Met Glu Ala Ala Ser Gln Pro Ala Asp Glu Pro Leu Arg Lys Arg
    20                  25                  30                  35

| | | |
|---|---|---|
| ccc cgc cga gac ggg cct ggc ctc ggg cgc agc ccg ggc gag ccg agc<br>Pro Arg Arg Asp Gly Pro Gly Leu Gly Arg Ser Pro Gly Glu Pro Ser<br>                40                          45                    50 | 200 |
| gca gca gtg gcg ccg gcg gcc gcg ggg tgt gag gcg gcg agc gcc gcg<br>Ala Ala Val Ala Pro Ala Ala Ala Gly Cys Glu Ala Ala Ser Ala Ala<br>         55                       60                       65 | 248 |
| gcc ccg gcg gcg ctg tgg cgg gag gcg gca ggg gcg gcg agc gcg<br>Ala Pro Ala Ala Leu Trp Arg Glu Ala Ala Gly Ala Ala Ala Ser Ala<br>        70                     75                     80 | 296 |
| gag cgg gag gcc ccg gcg acg gcc gtg gcc ggg gac gga gac aat ggg<br>Glu Arg Glu Ala Pro Ala Thr Ala Val Ala Gly Asp Gly Asp Asn Gly<br>85                       90                     95 | 344 |
| tcc ggc ctg cgg cgg gag ccg agg gcg gct gac gac ttc gac gac gac<br>Ser Gly Leu Arg Arg Glu Pro Arg Ala Ala Asp Asp Phe Asp Asp Asp<br>100                   105                 110              115 | 392 |
| gag ggc gag gag gag gac gag gcg gcg gcg gca gcg gcg gcg gca gcg<br>Glu Gly Glu Glu Glu Asp Glu Ala Ala Ala Ala Ala Ala Ala Ala Ala<br>                120                 125                130 | 440 |
| atc ggc tac cga gac aac ctc ctg ttg acc gat gga ctc ctc act aat<br>Ile Gly Tyr Arg Asp Asn Leu Leu Leu Thr Asp Gly Leu Leu Thr Asn<br>                135                 140                145 | 488 |
| ggc ttt cat tcc tgt gaa agt gat gac gat gac aga acg tca cac gcc<br>Gly Phe His Ser Cys Glu Ser Asp Asp Asp Asp Arg Thr Ser His Ala<br>                150                 155                160 | 536 |
| agc tct agt gac tgg act ccg cgg ccg cgg ata ggt cca tat act ttt<br>Ser Ser Ser Asp Trp Thr Pro Arg Pro Arg Ile Gly Pro Tyr Thr Phe<br>             165                 170                175 | 584 |
| gtt cag caa cat ctc atg att ggc acc gat cct cga aca att ctt aaa<br>Val Gln Gln His Leu Met Ile Gly Thr Asp Pro Arg Thr Ile Leu Lys<br>180                   185                 190              195 | 632 |
| gat tta tta cca gaa aca att cct cca cct gag ctg gat gat atg acg<br>Asp Leu Leu Pro Glu Thr Ile Pro Pro Pro Glu Leu Asp Asp Met Thr<br>                      200                 205                210 | 680 |
| ctg tgg cag att gtt att aat atc ctt tca gaa cca cca aag cgg aaa<br>Leu Trp Gln Ile Val Ile Asn Ile Leu Ser Glu Pro Pro Lys Arg Lys<br>                215                 220                225 | 728 |
| aaa aga aaa gat atc aat aca att gaa gat gct gtg aag tta ctg cag<br>Lys Arg Lys Asp Ile Asn Thr Ile Glu Asp Ala Val Lys Leu Leu Gln<br>             230                 235                240 | 776 |
| gag tgt aaa aag ata ata gtt ctg act gga gct ggg gtt tct gtc tcc<br>Glu Cys Lys Lys Ile Ile Val Leu Thr Gly Ala Gly Val Ser Val Ser<br>245                   250                 255 | 824 |
| tgt ggg att cct gac ttc aga tca aga gac ggt atc tat gct cgc ctt<br>Cys Gly Ile Pro Asp Phe Arg Ser Arg Asp Gly Ile Tyr Ala Arg Leu<br>260                   265                 270              275 | 872 |
| gcg gtg gac ttc cca gac ctc cca gac cct caa gcc atg ttt gat att<br>Ala Val Asp Phe Pro Asp Leu Pro Asp Pro Gln Ala Met Phe Asp Ile<br>                      280                 285                290 | 920 |
| gag tat ttt aga aaa gac cca aga cca ttc ttc aag ttt gca aag gaa<br>Glu Tyr Phe Arg Lys Asp Pro Arg Pro Phe Phe Lys Phe Ala Lys Glu<br>                295                 300                305 | 968 |
| ata tat ccc gga cag ttc cag ccg tct ctg tgt cac aaa ttc ata gct<br>Ile Tyr Pro Gly Gln Phe Gln Pro Ser Leu Cys His Lys Phe Ile Ala<br>             310                 315                320 | 1016 |
| ttg tca gat aag gaa gga aaa cta ctt cga aat tat act caa aat ata<br>Leu Ser Asp Lys Glu Gly Lys Leu Leu Arg Asn Tyr Thr Gln Asn Ile<br>325                   330                 335 | 1064 |
| gat acc ttg gag cag gtt gca gga atc caa agg atc ctt cag tgt cat<br>Asp Thr Leu Glu Gln Val Ala Gly Ile Gln Arg Ile Leu Gln Cys His<br>340                   345                 350              355 | 1112 |

| | | |
|---|---|---|
| ggt tcc ttt gca aca gca tct tgc ctg att tgt aaa tac aaa gtt gat<br>Gly Ser Phe Ala Thr Ala Ser Cys Leu Ile Cys Lys Tyr Lys Val Asp<br>                360                       365                      370 | 1160 |
| tgt gaa gct gtt cgt gga gac att ttt aat cag gta gtt cct cgg tgc<br>Cys Glu Ala Val Arg Gly Asp Ile Phe Asn Gln Val Val Pro Arg Cys<br>      375                      380                       385 | 1208 |
| cct agg tgc cca gct gat gag cca ctt gcc atc atg aag cca gag att<br>Pro Arg Cys Pro Ala Asp Glu Pro Leu Ala Ile Met Lys Pro Glu Ile<br>                390                       395                      400 | 1256 |
| gtc ttc ttt ggt gaa aac tta cca gaa cag ttt cat aga gcc atg aag<br>Val Phe Phe Gly Glu Asn Leu Pro Glu Gln Phe His Arg Ala Met Lys<br>405                      410                       415 | 1304 |
| tat gac aaa gat gaa gtt gac ctc ctc att gtt att gga tct tct ctg<br>Tyr Asp Lys Asp Glu Val Asp Leu Leu Ile Val Ile Gly Ser Ser Leu<br>420                      425                       430                      435 | 1352 |
| aaa gtg aga cca gta gca cta att cca agt tct ata ccc cat gaa gtg<br>Lys Val Arg Pro Val Ala Leu Ile Pro Ser Ser Ile Pro His Glu Val<br>                440                       445                      450 | 1400 |
| cct caa ata tta ata aat agg gaa cct ttg cct cat cta cat ttt gat<br>Pro Gln Ile Leu Ile Asn Arg Glu Pro Leu Pro His Leu His Phe Asp<br>                    455                      460                     465 | 1448 |
| gta gag ctc ctt gga gac tgc gat gtt ata att aat gag ttg tgt cat<br>Val Glu Leu Leu Gly Asp Cys Asp Val Ile Ile Asn Glu Leu Cys His<br>470                      475                       480 | 1496 |
| agg cta ggt ggt gaa tat gcc aaa ctt tgt tgt aac cct gta aag ctt<br>Arg Leu Gly Gly Glu Tyr Ala Lys Leu Cys Cys Asn Pro Val Lys Leu<br>                485                       490                     495 | 1544 |
| tca gaa att act gaa aaa cct cca cgc cca caa aag gaa ttg gtt cat<br>Ser Glu Ile Thr Glu Lys Pro Pro Arg Pro Gln Lys Glu Leu Val His<br>500                      505                       510                     515 | 1592 |
| tta tca gag ttg cca cca aca cct ctt cat att tcg gaa gac tca agt<br>Leu Ser Glu Leu Pro Pro Thr Pro Leu His Ile Ser Glu Asp Ser Ser<br>                520                       525                     530 | 1640 |
| tca cct gaa aga act gta cca caa gac tct tct gtg att gct aca ctt<br>Ser Pro Glu Arg Thr Val Pro Gln Asp Ser Ser Val Ile Ala Thr Leu<br>                    535                      540                     545 | 1688 |
| gta gac caa gca aca aac aac aat gtt aat gat tta gaa gta tct gaa<br>Val Asp Gln Ala Thr Asn Asn Asn Val Asn Asp Leu Glu Val Ser Glu<br>550                      555                       560 | 1736 |
| tca agt tgt gtg gaa gaa aaa cca caa gaa gta cag act agt agg aat<br>Ser Ser Cys Val Glu Glu Lys Pro Gln Glu Val Gln Thr Ser Arg Asn<br>      565                      570                       575 | 1784 |
| gtt gag aac att aat gtg gaa aat cca gat ttt aag gct gtt ggt tcc<br>Val Glu Asn Ile Asn Val Glu Asn Pro Asp Phe Lys Ala Val Gly Ser<br>580                      585                       590                   595 | 1832 |
| agt act gca gac aaa aat gaa aga act tca gtt gca gaa aca gtg aga<br>Ser Thr Ala Asp Lys Asn Glu Arg Thr Ser Val Ala Glu Thr Val Arg<br>                600                       605                     610 | 1880 |
| aaa tgc tgg cct aat aga ctt gca aag gag cag att agt aag cgg ctt<br>Lys Cys Trp Pro Asn Arg Leu Ala Lys Glu Gln Ile Ser Lys Arg Leu<br>                    615                      620                     625 | 1928 |
| gag ggt aat caa tac ctg ttt gta cca cca aat cgt tac ata ttc cac<br>Glu Gly Asn Gln Tyr Leu Phe Val Pro Pro Asn Arg Tyr Ile Phe His<br>630                      635                       640 | 1976 |
| ggt gct gag gta tac tca gac tct gaa gat gac gtc ttg tcc tct agt<br>Gly Ala Glu Val Tyr Ser Asp Ser Glu Asp Asp Val Leu Ser Ser Ser<br>645                      650                       655 | 2024 |
| tcc tgt ggc agt aac agt gac agt ggc aca tgc cag agt cca agt tta<br>Ser Cys Gly Ser Asn Ser Asp Ser Gly Thr Cys Gln Ser Pro Ser Leu | 2072 |

|   |   |   |   |   |   |   |   |   |   |   |   |   |   |   |   |   |
|---|---|---|---|---|---|---|---|---|---|---|---|---|---|---|---|---|
|   |   |   |   | 660 |   |   |   |   | 665 |   |   |   |   | 670 |   |   |   |   | 675 |

```
gaa gaa ccc ttg gaa gat gaa agt gaa att gaa gaa ttc tac aat ggc       2120
Glu Glu Pro Leu Glu Asp Glu Ser Glu Ile Glu Glu Phe Tyr Asn Gly
                    680                 685                 690 ttg gaa gat gat acg gag agg ccc gaa tgt gct gga gga tct gga ttt       2168
Leu Glu Asp Asp Thr Glu Arg Pro Glu Cys Ala Gly Gly Ser Gly Phe
                695                 700                 705 gga gct gat gga ggg gat caa gag gtt gtt aat gaa gct ata gct aca       2216
Gly Ala Asp Gly Gly Asp Gln Glu Val Val Asn Glu Ala Ile Ala Thr
            710                 715                 720 aga cag gaa ttg aca gat gta aac tat cca tca gac aaa tca               2258
Arg Gln Glu Leu Thr Asp Val Asn Tyr Pro Ser Asp Lys Ser
        725                 730                 735 taacactatt gaagctgtcc ggattcagga attgctccac cagcattggg aactttagca    2318
tgtcaaaaaa atgaatgttt acttgtgaac ttgaacaagg aaatctgaaa gatgtattat    2378
ttatagactg gaaatagat tgtcttcttg gataatttct aaagttccat catttctgtt     2438
tgtacttgta cattcaacac tgttggttga cttcatcttc ctttcaaggt tcatttgtat    2498
gatacattcg tatgtatgta aattttgtt ttttgcctaa tgagtttcaa cctttttaaag    2558
ttttcaaaag ccattggaat gttaatgtaa agggaacagc ttatctagac caagaatgg     2618
tatttcacac ttttttgttt gtaacattga atagtttaaa gccctcaatt tctgttctgc    2678
tgaactttta ttttaggac agttaacttt ttaaacactg cattttcca aaacttgtgg      2738
cagctaactt tttaaaatca cagatgactt gtaatgtgag gagtcagcac cgtgtctgga   2798
gcactcaaaa cttgggctca gtgtgtgaag cgtacttact gcatcgtttt tgtacttgct   2858
gcagacgtgg taatgtccaa acaggcccct gagactaatc tgataaatga tttggaaatg   2918
tgtttcagtt gttctagaaa caatagtgcc tgtctatata ggtcccctta gtttgaatat   2978
ttgccattgt ttaattaaat acctatcact gtggtagagc ctgcatagat cttcaccaca   3038
aatactgcca agatgtgaat atgcaaagcc tttctgaatc taataatggt acttctactg   3098
gggagagtgt aatattttgg actgctgttt ttccattaat gaggaaagca ataggcctct   3158
taattaaagt cccaaagtca taagataaat tgtagctcaa ccagaaagta cactgttgcc   3218
tgttgaggat ttggtgtaat gtatcccaag gtgttagcct tgtattatgg agatgaatac   3278
agatccaata gtcaaatgaa actagttctt agttatttaa aagcttagct tgccttaaaa   3338
ctagggatca attttctcaa ctgcagaaac ttttagcctt tcaaacagtt cacacctcag   3398
aaagtcagta tttattttac agacttcttt ggaacattgc ccccaaattt aaatattcat   3458
gtgggtttag tatttattac aaaaaaatga tttgaaatat agctgttctt tatgcataaa   3518
atacccagtt aggaccatta ctgccagagg agaaagtat taagtagctc atttccctac    3578
ctaaaagata actgaattta tttggctaca ctaaagaatg cagtatattt agttttccat   3638
ttgcatgatg tgtttgtgct atagacaata ttttaaattg aaaaatttgt tttaaattat   3698
ttttacagtg aagactgttt tcagctcttt ttatattgta catagacttt tatgtaatct   3758
ggcatatgtt ttgtagaccg tttaatgact ggattatctt cctccaactt ttgaaataca   3818
aaaacagtgt tttatactaa aaaaaaaaaa agtcgacgcg ccgcgaatt c              3869
```

<210> SEQ ID NO 26
<211> LENGTH: 737
<212> TYPE: PRT
<213> ORGANISM: Mus musculus

<400> SEQUENCE: 26

-continued

```
Met Ala Asp Glu Val Ala Leu Ala Leu Gln Ala Ala Gly Ser Pro Ser
 1               5                  10                  15

Ala Ala Ala Ala Met Glu Ala Ala Ser Gln Pro Ala Asp Glu Pro Leu
             20                  25                  30

Arg Lys Arg Pro Arg Arg Asp Gly Pro Gly Leu Gly Arg Ser Pro Gly
         35                  40                  45

Glu Pro Ser Ala Ala Val Ala Pro Ala Ala Gly Cys Glu Ala Ala
     50                  55                  60

Ser Ala Ala Pro Ala Ala Leu Trp Arg Glu Ala Ala Gly Ala Ala
 65                  70                  75                  80

Ala Ser Ala Glu Arg Glu Ala Pro Ala Thr Ala Val Ala Gly Asp Gly
                 85                  90                  95

Asp Asn Gly Ser Gly Leu Arg Arg Glu Pro Arg Ala Ala Asp Asp Phe
             100                 105                 110

Asp Asp Asp Glu Gly Glu Glu Asp Glu Ala Ala Ala Ala Ala
             115                 120                 125

Ala Ala Ala Ile Gly Tyr Arg Asp Asn Leu Leu Leu Thr Asp Gly Leu
 130                 135                 140

Leu Thr Asn Gly Phe His Ser Cys Glu Ser Asp Asp Asp Arg Thr
145                 150                 155                 160

Ser His Ala Ser Ser Ser Asp Trp Thr Pro Arg Pro Arg Ile Gly Pro
                 165                 170                 175

Tyr Thr Phe Val Gln Gln His Leu Met Ile Gly Thr Asp Pro Arg Thr
             180                 185                 190

Ile Leu Lys Asp Leu Leu Pro Glu Thr Ile Pro Pro Glu Leu Asp
         195                 200                 205

Asp Met Thr Leu Trp Gln Ile Val Ile Asn Ile Leu Ser Glu Pro Pro
 210                 215                 220

Lys Arg Lys Lys Arg Lys Asp Ile Asn Thr Ile Glu Asp Ala Val Lys
225                 230                 235                 240

Leu Leu Gln Glu Cys Lys Lys Ile Ile Val Leu Thr Gly Ala Gly Val
                 245                 250                 255

Ser Val Ser Cys Gly Ile Pro Asp Phe Arg Ser Arg Asp Gly Ile Tyr
             260                 265                 270

Ala Arg Leu Ala Val Asp Phe Pro Asp Leu Pro Asp Pro Gln Ala Met
         275                 280                 285

Phe Asp Ile Glu Tyr Phe Arg Lys Asp Pro Arg Pro Phe Phe Lys Phe
 290                 295                 300

Ala Lys Glu Ile Tyr Pro Gly Gln Phe Gln Pro Ser Leu Cys His Lys
305                 310                 315                 320

Phe Ile Ala Leu Ser Asp Lys Glu Gly Lys Leu Leu Arg Asn Tyr Thr
                 325                 330                 335

Gln Asn Ile Asp Thr Leu Glu Gln Val Ala Gly Ile Gln Arg Ile Leu
             340                 345                 350

Gln Cys His Gly Ser Phe Ala Thr Ala Ser Cys Leu Ile Cys Lys Tyr
         355                 360                 365

Lys Val Asp Cys Glu Ala Val Arg Gly Asp Ile Phe Asn Gln Val Val
     370                 375                 380

Pro Arg Cys Pro Arg Cys Pro Ala Asp Glu Pro Leu Ala Ile Met Lys
385                 390                 395                 400

Pro Glu Ile Val Phe Phe Gly Glu Asn Leu Pro Glu Gln Phe His Arg
                 405                 410                 415
```

```
Ala Met Lys Tyr Asp Lys Asp Glu Val Asp Leu Leu Ile Val Ile Gly
            420                 425                 430

Ser Ser Leu Lys Val Arg Pro Val Ala Leu Ile Pro Ser Ser Ile Pro
        435                 440                 445

His Glu Val Pro Gln Ile Leu Ile Asn Arg Pro Leu Pro His Leu
    450                 455                 460

His Phe Asp Val Glu Leu Leu Gly Asp Cys Asp Val Ile Ile Asn Glu
465                 470                 475                 480

Leu Cys His Arg Leu Gly Gly Glu Tyr Ala Lys Leu Cys Cys Asn Pro
            485                 490                 495

Val Lys Leu Ser Glu Ile Thr Glu Lys Pro Pro Arg Pro Gln Lys Glu
        500                 505                 510

Leu Val His Leu Ser Glu Leu Pro Pro Thr Pro Leu His Ile Ser Glu
    515                 520                 525

Asp Ser Ser Ser Pro Glu Arg Thr Val Pro Gln Asp Ser Ser Val Ile
530                 535                 540

Ala Thr Leu Val Asp Gln Ala Thr Asn Asn Asn Val Asn Asp Leu Glu
545                 550                 555                 560

Val Ser Glu Ser Ser Cys Val Glu Glu Lys Pro Gln Glu Val Gln Thr
            565                 570                 575

Ser Arg Asn Val Glu Asn Ile Asn Val Glu Asn Pro Asp Phe Lys Ala
        580                 585                 590

Val Gly Ser Ser Thr Ala Asp Lys Asn Glu Arg Thr Ser Val Ala Glu
            595                 600                 605

Thr Val Arg Lys Cys Trp Pro Asn Arg Leu Ala Lys Glu Gln Ile Ser
    610                 615                 620

Lys Arg Leu Glu Gly Asn Gln Tyr Leu Phe Val Pro Pro Asn Arg Tyr
625                 630                 635                 640

Ile Phe His Gly Ala Glu Val Tyr Ser Asp Ser Glu Asp Asp Val Leu
            645                 650                 655

Ser Ser Ser Ser Cys Gly Ser Asn Ser Asp Ser Gly Thr Cys Gln Ser
                660                 665                 670

Pro Ser Leu Glu Glu Pro Leu Glu Asp Glu Ser Glu Ile Glu Glu Phe
            675                 680                 685

Tyr Asn Gly Leu Glu Asp Asp Thr Glu Arg Pro Glu Cys Ala Gly Gly
        690                 695                 700

Ser Gly Phe Gly Ala Asp Gly Gly Asp Gln Glu Val Val Asn Glu Ala
705                 710                 715                 720

Ile Ala Thr Arg Gln Glu Leu Thr Asp Val Asn Tyr Pro Ser Asp Lys
                725                 730                 735

Ser

<210> SEQ ID NO 27
<211> LENGTH: 14
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 8
<223> OTHER INFORMATION: Xaa = Leu or Ala

<400> SEQUENCE: 27

Gly Ala Gly Ile Ser Thr Ser Xaa Gly Ile Pro Asp Phe Arg
 1               5                  10
```

<210> SEQ ID NO 28
<211> LENGTH: 6
<212> TYPE: PRT
<213> ORGANISM: Artificial Sequence
<220> FEATURE:
<223> OTHER INFORMATION: Consensus sequence

<400> SEQUENCE: 28

Tyr Thr Gln Asn Ile Asp
1               5

<210> SEQ ID NO 29
<211> LENGTH: 6
<212> TYPE: PRT
<213> ORGANISM: Artificial Sequence
<220> FEATURE:
<223> OTHER INFORMATION: Consensus sequence

<400> SEQUENCE: 29

Lys Arg Lys Lys Arg Lys
1               5

<210> SEQ ID NO 30
<211> LENGTH: 5
<212> TYPE: PRT
<213> ORGANISM: Saccharomyces cerevisiae

<400> SEQUENCE: 30

Val Ser Thr Ser Leu
1               5

<210> SEQ ID NO 31
<211> LENGTH: 5
<212> TYPE: PRT
<213> ORGANISM: Mus musculus

<400> SEQUENCE: 31

Val Ser Val Ser Cys
1               5

<210> SEQ ID NO 32
<211> LENGTH: 6
<212> TYPE: PRT
<213> ORGANISM: Mus musculus

<400> SEQUENCE: 32

Leu Ile Asn Lys Glu Lys
1               5

<210> SEQ ID NO 33
<211> LENGTH: 6
<212> TYPE: PRT
<213> ORGANISM: Mus musculus

<400> SEQUENCE: 33

Leu Ile Asn Arg Asp Leu
1               5

<210> SEQ ID NO 34
<211> LENGTH: 699
<212> TYPE: DNA
<213> ORGANISM: Unknown
<220> FEATURE:
<223> OTHER INFORMATION: EST cDNA clone 557657
<220> FEATURE:
<221> NAME/KEY: CDS

<222> LOCATION: (3)...(698)

<400> SEQUENCE: 34

```
cc acg cgt ccg cgg acg cgt ggg cac ggg aca gag cag tcg gtg aca      47
   Thr Arg Pro Arg Thr Arg Gly His Gly Thr Glu Gln Ser Val Thr
   1               5                   10                  15 gtc ccg agg gcc ccc acc ccg ttc cca tgg ccg agc cgg acc gat tca      95
Val Pro Arg Ala Pro Thr Pro Phe Pro Trp Pro Ser Arg Thr Asp Ser
                20                  25                  30 gac tcg gac act gag gga gga gcc act ggt gga gag gca gag atg gac     143
Asp Ser Asp Thr Glu Gly Gly Ala Thr Gly Gly Glu Ala Glu Met Asp
            35                  40                  45 ttc ctg agg aat tta ttc acc cag acc ctg ggc ctg ggt tcc caa aag     191
Phe Leu Arg Asn Leu Phe Thr Gln Thr Leu Gly Leu Gly Ser Gln Lys
        50                  55                  60 gag cgt ctt cta gac gag ctg acc ctc gaa gga gtg aca cgc tac atg     239
Glu Arg Leu Leu Asp Glu Leu Thr Leu Glu Gly Val Thr Arg Tyr Met
65                  70                  75                  80 cag agc gag cgc tgc cgc aag gtc atc tgt ttg gtg gga gcc gga atc     287
Gln Ser Glu Arg Cys Arg Lys Val Ile Cys Leu Val Gly Ala Gly Ile
                85                  90                  95 tcc acg tcc gcg ggt atc cct gac ttc cgc tcc ccg tcc act ggc ctc     335
Ser Thr Ser Ala Gly Ile Pro Asp Phe Arg Ser Pro Ser Thr Gly Leu
            100                 105                 110 tat gca aac ctg gag aag tac cac ctt cct tac cca gag gcc atc ttt     383
Tyr Ala Asn Leu Glu Lys Tyr His Leu Pro Tyr Pro Glu Ala Ile Phe
        115                 120                 125 gag atc agc tac ttc aag aaa cat ccg gaa ccc ttc ttt gcc ctt gcc     431
Glu Ile Ser Tyr Phe Lys Lys His Pro Glu Pro Phe Phe Ala Leu Ala
    130                 135                 140 aag gag ctc tat ccc ggg cag ttc aag cca acc atc tgc cac tac ttc     479
Lys Glu Leu Tyr Pro Gly Gln Phe Lys Pro Thr Ile Cys His Tyr Phe
145                 150                 155                 160 atc cgc ctg ctg aag gag aag ggg ctg ctg ctg cgc tgc tac acg cag     527
Ile Arg Leu Leu Lys Glu Lys Gly Leu Leu Leu Arg Cys Tyr Thr Gln
                165                 170                 175 aac ata gac acg ctg gaa cga gtg gcg ggg ctg gag ccc cag gac ctg     575
Asn Ile Asp Thr Leu Glu Arg Val Ala Gly Leu Glu Pro Gln Asp Leu
            180                 185                 190 gtg gag gcc cac ggc acc ttc tac aca tca cac tgt gtc aac acc tcc     623
Val Glu Ala His Gly Thr Phe Tyr Thr Ser His Cys Val Asn Thr Ser
        195                 200                 205 tgc aga aaa gaa tac acg atg ggc tgg atg aaa gag aag att tct cag     671
Cys Arg Lys Glu Tyr Thr Met Gly Trp Met Lys Glu Lys Ile Ser Gln
    210                 215                 220 aag caa ctc cca ggt gtg agc agt gtc a                               699
Lys Gln Leu Pro Gly Val Ser Ser Val
        225                 230
```

<210> SEQ ID NO 35
<211> LENGTH: 232
<212> TYPE: PRT
<213> ORGANISM: Unknown
<220> FEATURE:
<223> OTHER INFORMATION: EST cDNA clone 557657

<400> SEQUENCE: 35

```
Thr Arg Pro Arg Thr Arg Gly His Gly Thr Glu Gln Ser Val Thr Val
1               5                   10                  15

Pro Arg Ala Pro Thr Pro Phe Pro Trp Pro Ser Arg Thr Asp Ser Asp
            20                  25                  30
```

```
Ser Asp Thr Glu Gly Gly Ala Thr Gly Gly Glu Ala Glu Met Asp Phe
        35                  40                  45

Leu Arg Asn Leu Phe Thr Gln Thr Leu Gly Leu Gly Ser Gln Lys Glu
 50                  55                  60

Arg Leu Leu Asp Glu Leu Thr Leu Glu Gly Val Thr Arg Tyr Met Gln
 65                  70                  75                  80

Ser Glu Arg Cys Arg Lys Val Ile Cys Leu Val Gly Ala Gly Ile Ser
                 85                  90                  95

Thr Ser Ala Gly Ile Pro Asp Phe Arg Ser Pro Ser Thr Gly Leu Tyr
                100                 105                 110

Ala Asn Leu Glu Lys Tyr His Leu Pro Tyr Pro Glu Ala Ile Phe Glu
                115                 120                 125

Ile Ser Tyr Phe Lys Lys His Pro Glu Pro Phe Phe Ala Leu Ala Lys
                130                 135                 140

Glu Leu Tyr Pro Gly Gln Phe Lys Pro Thr Ile Cys His Tyr Phe Ile
145                 150                 155                 160

Arg Leu Leu Lys Glu Lys Gly Leu Leu Leu Arg Cys Tyr Thr Gln Asn
                165                 170                 175

Ile Asp Thr Leu Glu Arg Val Ala Gly Leu Glu Pro Gln Asp Leu Val
                180                 185                 190

Glu Ala His Gly Thr Phe Tyr Thr Ser His Cys Val Asn Thr Ser Cys
                195                 200                 205

Arg Lys Glu Tyr Thr Met Gly Trp Met Lys Lys Ile Ser Gln Lys
210                 215                 220

Gln Leu Pro Gly Val Ser Ser Val
225                 230

<210> SEQ ID NO 36
<211> LENGTH: 4
<212> TYPE: PRT
<213> ORGANISM: Mus musculus

<400> SEQUENCE: 36

Thr Leu Gly Leu
  1

<210> SEQ ID NO 37
<211> LENGTH: 4
<212> TYPE: PRT
<213> ORGANISM: Mus musculus

<400> SEQUENCE: 37

Phe Gly Gly Gly
  1

<210> SEQ ID NO 38
<211> LENGTH: 15
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 4
<223> OTHER INFORMATION: Xaa = Val or Ile
<220> FEATURE:
<221> NAME/KEY: VARIANT
<222> LOCATION: 6
<223> OTHER INFORMATION: Xaa = Thr or Val
<220> FEATURE:
<221> NAME/KEY: VARIANT
```

```
-continued

<222> LOCATION: 8
<223> OTHER INFORMATION: Xaa = Leu, Cys, or Ala

<400> SEQUENCE: 38

Gly Ala Gly Xaa Ser Xaa Ser Xaa Gly Ile Pro Asp Phe Arg Ser
1               5                   10                  15
```